United States Patent
Eggers et al.

(10) Patent No.: US 6,514,248 B1
(45) Date of Patent: Feb. 4, 2003

(54) ACCURATE CUTTING ABOUT AND INTO TISSUE VOLUMES WITH ELECTROSURGICALLY DEPLOYED ELECTRODES

(75) Inventors: Philip E. Eggers, Dublin, OH (US); Eric A. Eggers, Columbus, OH (US); Andrew R. Eggers, Ostrander, OH (US)

(73) Assignee: Neothermia Corporation, Natick, MA (US)

( * ) Notice: Subject to any disclaimer, the term of this patent is extended or adjusted under 35 U.S.C. 154(b) by 0 days.

(21) Appl. No.: 09/418,923

(22) Filed: Oct. 15, 1999

(51) Int. Cl.[7] ............................................... A61B 18/18
(52) U.S. Cl. ............................ 606/41; 606/45; 606/48; 606/47
(58) Field of Search ............................. 606/41, 45, 46, 606/47, 48, 49

(56) References Cited

U.S. PATENT DOCUMENTS

| | | | |
|---|---|---|---|
| 1,813,902 A | 7/1931 | Bovie | |
| 3,910,279 A | 10/1975 | Okada et al. | |
| 3,955,578 A | * 5/1976 | Chamness | 606/47 |

(List continued on next page.)

FOREIGN PATENT DOCUMENTS

| | | |
|---|---|---|
| DE | 195 28 440 A1 | 6/1997 |
| EP | 0 472 368 B1 | 6/1995 |
| EP | 0 829 232 A3 | 3/1998 |
| EP | 0 908 156 A1 | 4/1999 |
| FR | 2275226 | 1/1976 |
| GB | 1 331 468 | 1/1997 |
| NL | 1.004723 | 8/1998 |
| SU | 1235497 | 4/1984 |
| SU | 1355266 | 12/1985 |
| WO | WO92/20291 | 11/1992 |
| WO | WO 95/02370 | 1/1995 |
| WO | WO 95/02371 | 1/1995 |
| WO | WO 96/29946 | 10/1996 |
| WO | WO98/08441 | 3/1998 |
| WO | WO99/04704 | 2/1999 |
| WO | WO99/43262 | 9/1999 |
| WO | WO 99/44506 | 9/1999 |
| WO | WO99/53851 | 10/1999 |

OTHER PUBLICATIONS

Kalman, Johnatan M., et al. "Radiofrequency Catheter Ablation For Atrial Fibrillation." *Cardiology Clinics* 1997; 15: 721–737.

Cosio, Francisco G., et al. "Atrial Flutter Mapping and Ablation II." *Pace* 1996; 19: 965–975.

Lorentzen, Torben. "The Loop Electrode: In Vitro Evaluation of a Device for Ultrasound–Guided Interstitial Tissue Ablation Using Radiofrequency Electrosurgery." *Acad. Radiol.* 1996; 3: 219–224.

Lorentzen, T., et al. "The Loop Electrode: a New Device for US–Guided Interstitial Tissue Ablation Using Ablation Using Radiofrequency Electrosurgery—An Animal Study." *Min. Invas. Ther. & Allied Technol.* 1996; 5: 511–516.

(List continued on next page.)

Primary Examiner—Rosiland Kearney
(74) Attorney, Agent, or Firm—Mueller and Smith, LPA

(57) ABSTRACT

Method, system and apparatus for carrying out accurate electrosurgical cutting. A thin resilient electrode is utilized at the forward end region of an instrument which is deployable from a longitudinally disposed slot positioned rearwardly of the tip of the instrument. Lateral sides of the slot extend between a forward location adjacent the tip and a rearward location. The electrode is deployed by urging it forwardly in compression to form an arch profile supported by the abutting slot sides adjacent the forward and rearward locations. Electrosurgically excitable with a cutting output, the electrode may carry out a cutting action both during its deployment and retraction into the noted slot. This permits a pivoting maneuver effective for circumscribing a volume of targeted tissue.

18 Claims, 26 Drawing Sheets

U.S. PATENT DOCUMENTS

| | | |
|---|---|---|
| 4,016,886 A | 4/1977 | Doss et al. |
| 4,116,198 A | 9/1978 | Roos |
| 4,121,592 A | 10/1978 | Whalley |
| 4,140,109 A | 2/1979 | Savic et al. |
| 4,520,249 A | 5/1985 | Czerlinski |
| 4,638,802 A | 1/1987 | Okada |
| 4,658,836 A | 4/1987 | Turner |
| 4,679,561 A | 7/1987 | Doss |
| 4,737,628 A | 4/1988 | Lovoi |
| 4,776,334 A | 10/1988 | Prionas |
| 4,821,725 A | 4/1989 | Azam et al. |
| 4,846,196 A | 7/1989 | Wiksell et al. |
| 4,860,744 A | 8/1989 | Johnson et al. |
| 4,872,458 A | 10/1989 | Kanehira et al. |
| 4,919,138 A | 4/1990 | Nordenstroom |
| 4,920,978 A | 5/1990 | Colvin |
| 4,979,518 A | 12/1990 | Itoh et al. |
| 5,069,223 A | 12/1991 | McRae |
| 5,080,660 A | 1/1992 | Buelna |
| 5,122,137 A | 6/1992 | Lennox |
| 5,163,938 A | 11/1992 | Kambara et al. |
| 5,192,280 A | 3/1993 | Parins |
| 5,224,488 A | 7/1993 | Neuffer |
| 5,251,645 A | 10/1993 | Fenn |
| 5,282,799 A | 2/1994 | Rydell |
| 5,284,144 A | 2/1994 | Delannoy et al. |
| 5,324,288 A | 6/1994 | Billings et al. |
| 5,336,227 A | 8/1994 | Nakao et al. |
| 5,370,675 A | 12/1994 | Edwards et al. |
| 5,403,311 A | 4/1995 | Abele et al. |
| 5,415,656 A | 5/1995 | Tihon et al. |
| 5,421,819 A | 6/1995 | Edwards et al. |
| 5,423,809 A | 6/1995 | Klicek |
| 5,454,790 A | 10/1995 | Dubrul |
| 5,458,597 A | 10/1995 | Edwards et al. |
| 5,470,308 A | 11/1995 | Edwards et al. |
| 5,470,309 A | 11/1995 | Edwards et al. |
| 5,472,441 A | 12/1995 | Edwards et al. |
| 5,486,161 A | 1/1996 | Lax et al. |
| 5,486,182 A | 1/1996 | Nakao et al. |
| 5,487,385 A * | 1/1996 | Avitall ........................ 128/642 |
| 5,500,012 A | 3/1996 | Brucker et al. |
| 5,507,743 A | 4/1996 | Edwards et al. |
| 5,514,131 A | 5/1996 | Edwards et al. |
| 5,536,267 A | 7/1996 | Edwards et al. |
| 5,554,159 A * | 9/1996 | Fischer ........................ 606/45 |
| 5,599,345 A | 2/1997 | Edwards et al. |
| 5,599,346 A | 2/1997 | Edwards et al. |
| 5,607,389 A | 3/1997 | Edwards et al. |
| 5,626,577 A | 5/1997 | Harris |
| 5,651,780 A | 7/1997 | Jackson et al. |
| 5,672,173 A | 9/1997 | Gough et al. |
| 5,672,174 A | 9/1997 | Gough et al. |
| 5,683,384 A | 11/1997 | Gough et al. |
| 5,720,744 A | 2/1998 | Eggleston et al. |
| 5,728,143 A | 3/1998 | Gough et al. |
| 5,730,127 A | 3/1998 | Avitall |
| 5,741,271 A | 4/1998 | Nakao et al. |
| 5,749,870 A | 5/1998 | Gloth et al. |
| 5,759,187 A | 6/1998 | Nakao et al. |
| 5,766,215 A | 6/1998 | Muri et al. |
| 5,782,840 A | 7/1998 | Nakao |
| 5,810,806 A | 9/1998 | Ritchart et al. |
| 5,857,982 A | 1/1999 | Milliman et al. |
| 5,868,740 A | 2/1999 | LaVeen et al. |
| 5,882,316 A | 3/1999 | Chu et al. |
| 5,925,044 A | 7/1999 | Hofmann et al. |
| 5,928,229 A * | 7/1999 | Gough et al. .................. 606/41 |
| 5,957,923 A | 9/1999 | Hahnen et al. |
| 6,013,086 A | 1/2000 | Ouchi et al. |
| 6,016,809 A * | 1/2000 | Mulier et al. ................ 128/898 |
| 6,022,362 A | 2/2000 | Lee et al. |
| 6,063,077 A * | 5/2000 | Schaer ........................ 606/41 |
| 6,068,653 A * | 5/2000 | LaFontaine .................. 607/116 |
| 6,071,282 A * | 6/2000 | Fleischman ................... 606/41 |
| 6,086,532 A * | 7/2000 | Panescu et al. ................ 66/437 |
| 6,331,166 B1 * | 12/2001 | Burbank et al. ............. 600/567 |

OTHER PUBLICATIONS

Kay, G. Neal, et al. "The Present Role of Radiofrequency Catheter Ablation in the Management of Cardiac Arrhythmias." *The American Journal of Medicine* 1996; 100: 344–356.

Steinberg, Jonathan S., et al. Radiofrequency Catheter Ablation of Atrial Flutter: Procedural Success and Long–Term Outcome.

Akiyoshi, T., et al. "Impaired Production of Interlukin–2 after Surgery." *Clin. Exp. Immunology* 1985; 59: 45–49.

Lennard, T., et al. "The Influence of Surgical Operations on Components of the Human Immune System." *British J. of Surgery* 72 1985; 72: 771–776.

Neel, H., et al. "Requisites for Successful Cryogenic Surgery of Cancer." *Arch. Surg.* 1971; 102: 45–48.

Denekamp, et al. "Vascular Occulation and Tumor Cell Death." *Eur. J. Cancer and Clinical Oncology* 1983; 19: 271–275.

Wood, et al. "Radiofrequency Catheter Ablation for the Management of Cardiac Tachyarrhythmias." *Am. J. Med. Sci.* 1993; 306(4): 241–247.

Ferris IDG, Hainer BL, Pfenninger JL, Zubert TJ, Dewitt DE, Line RL. "Electrosurgical loop excision of the cervical transformation zone: the experience of family physicians." *Journal of Family Practice* 1995; 41 (4): 337–344.

Mor–Yosef S, Lopes A, Pearson S, Monaghan JM. "Loop diathermy cone biopsy." *Obstetrics and Gynecology* 1990P 75 (5): 884–886.

\* cited by examiner

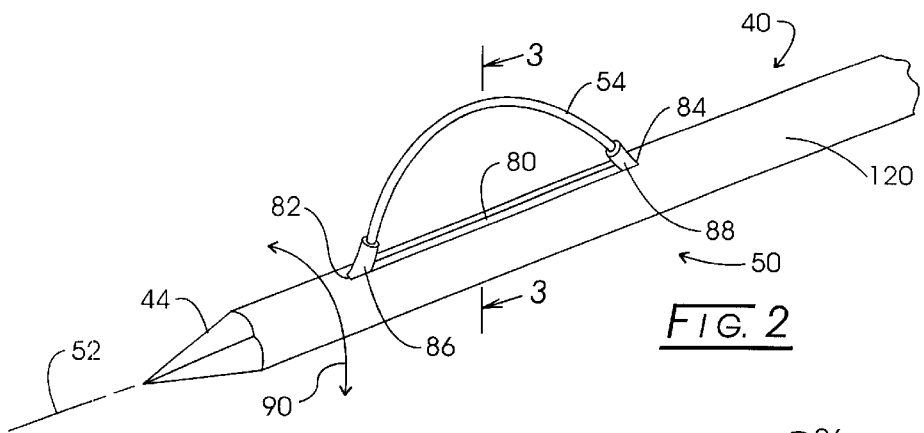
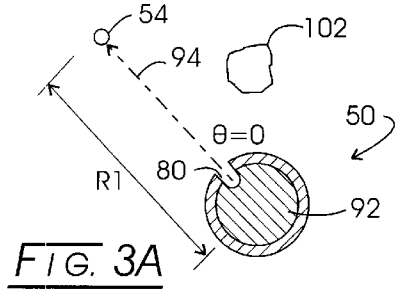
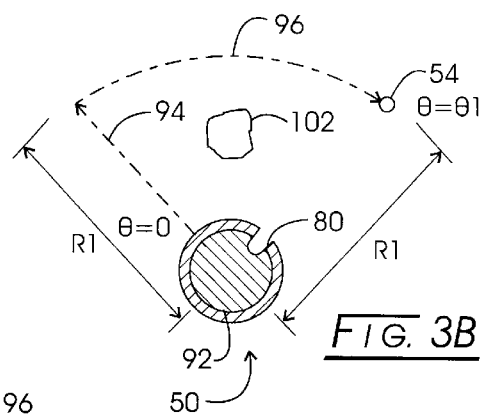
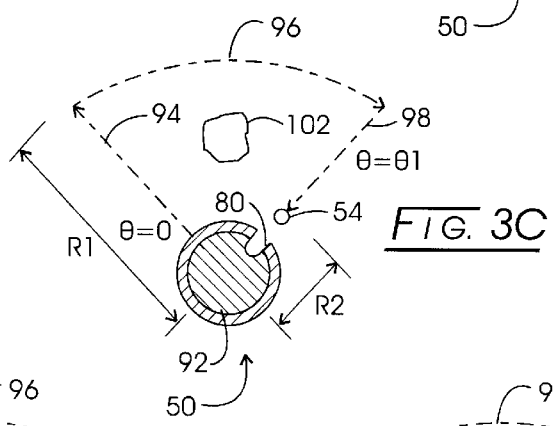
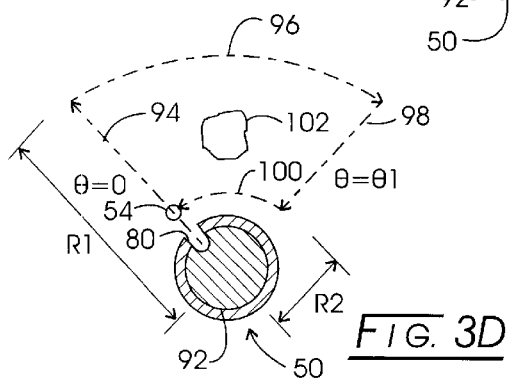
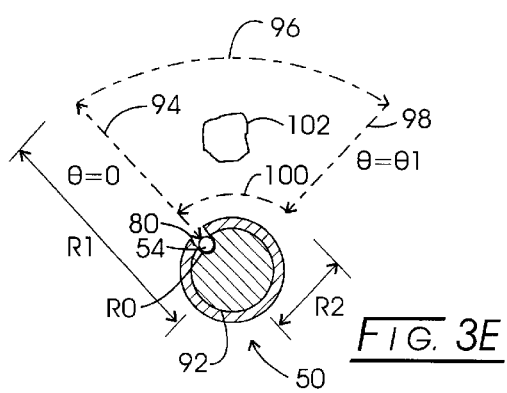

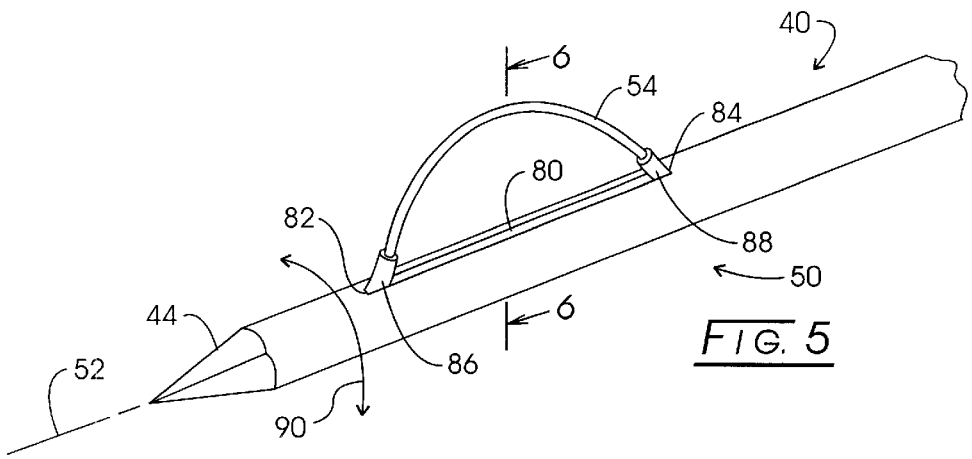
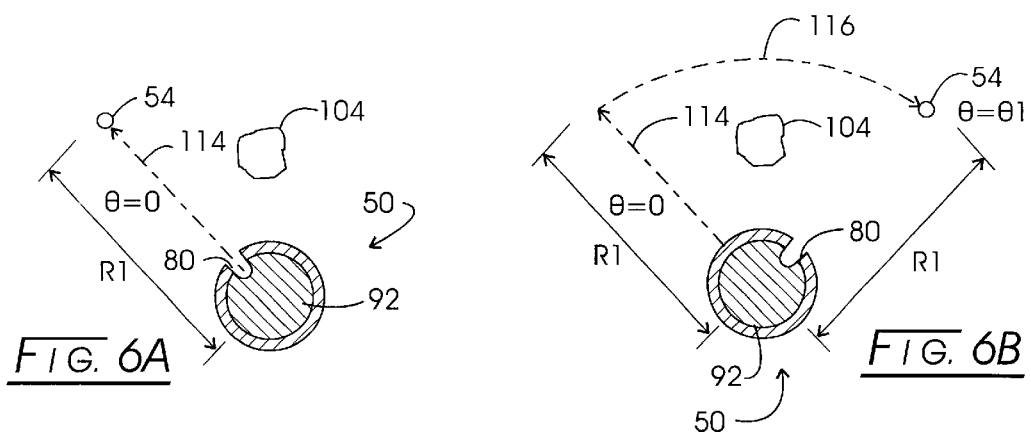
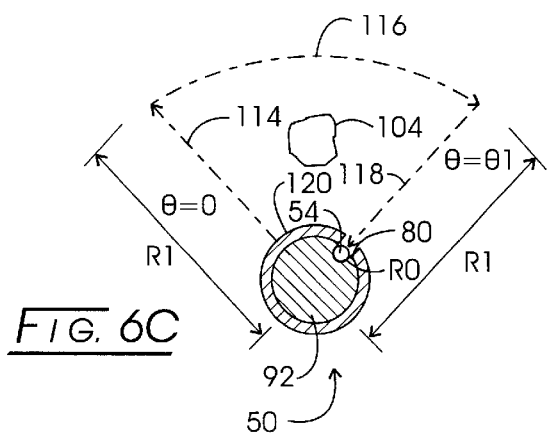

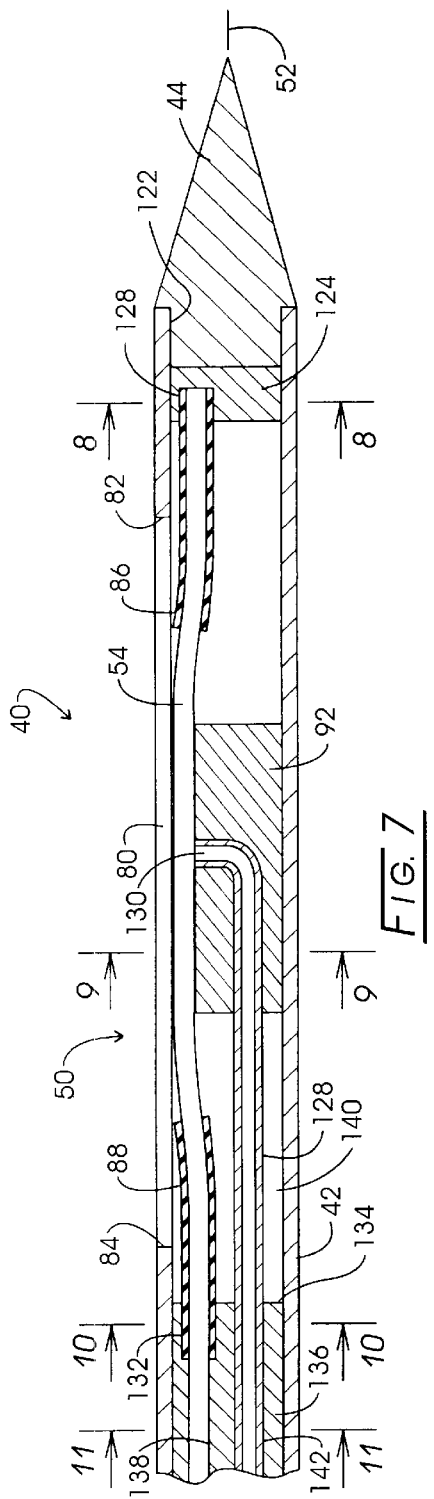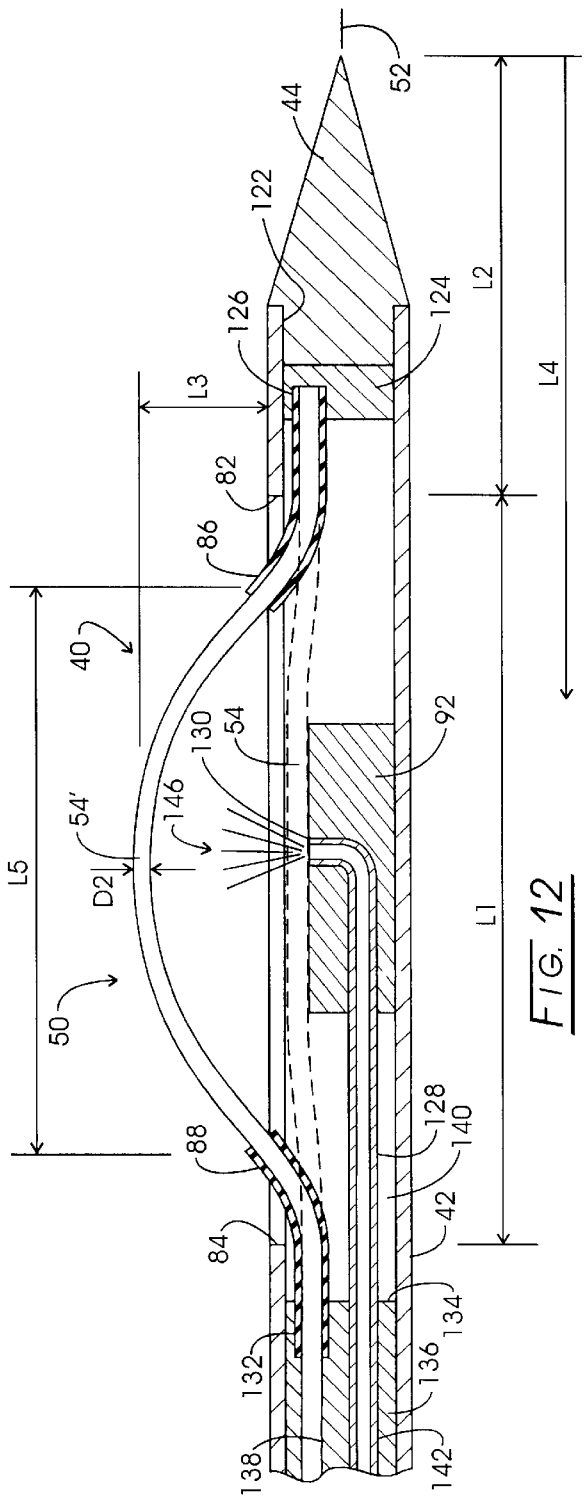

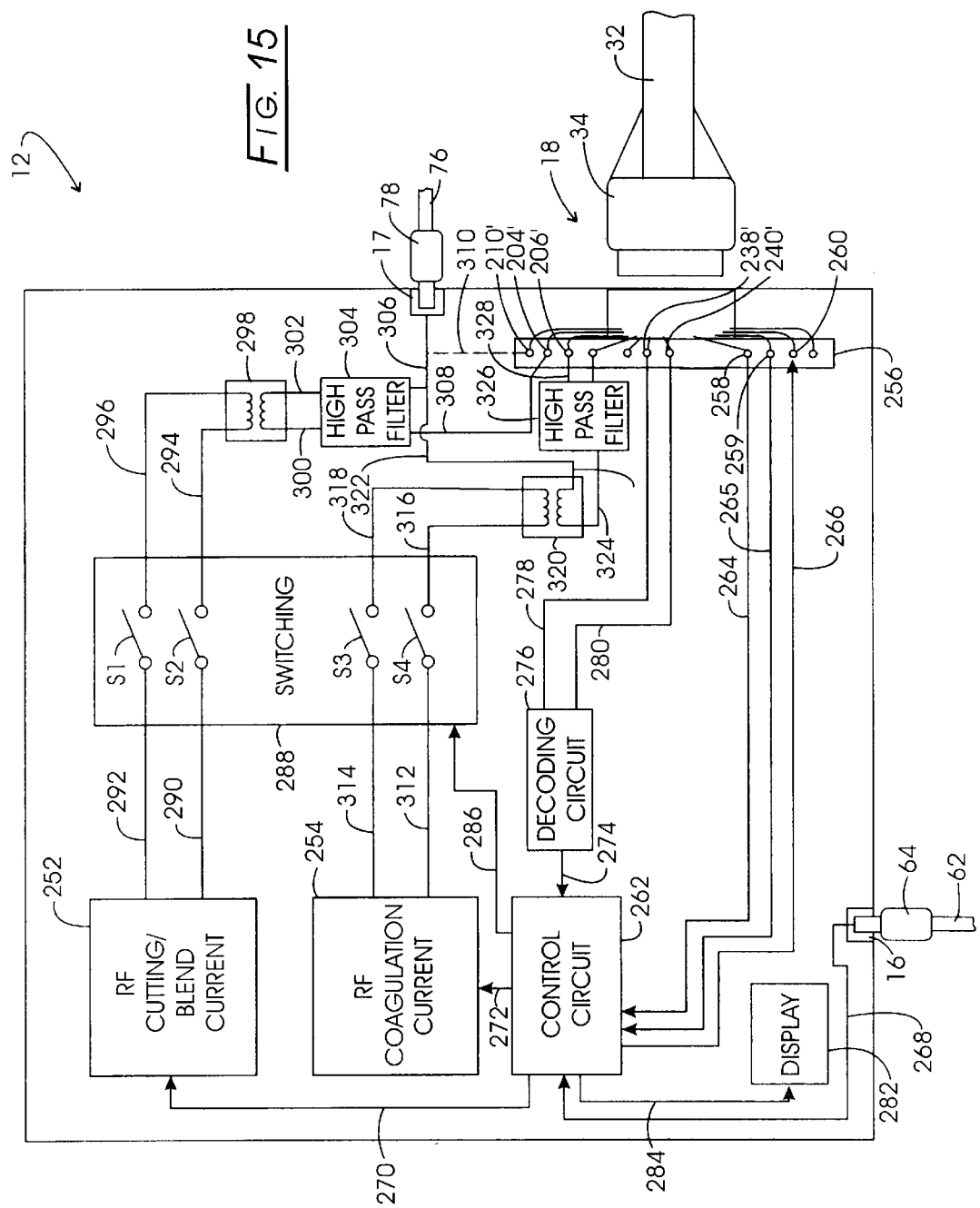

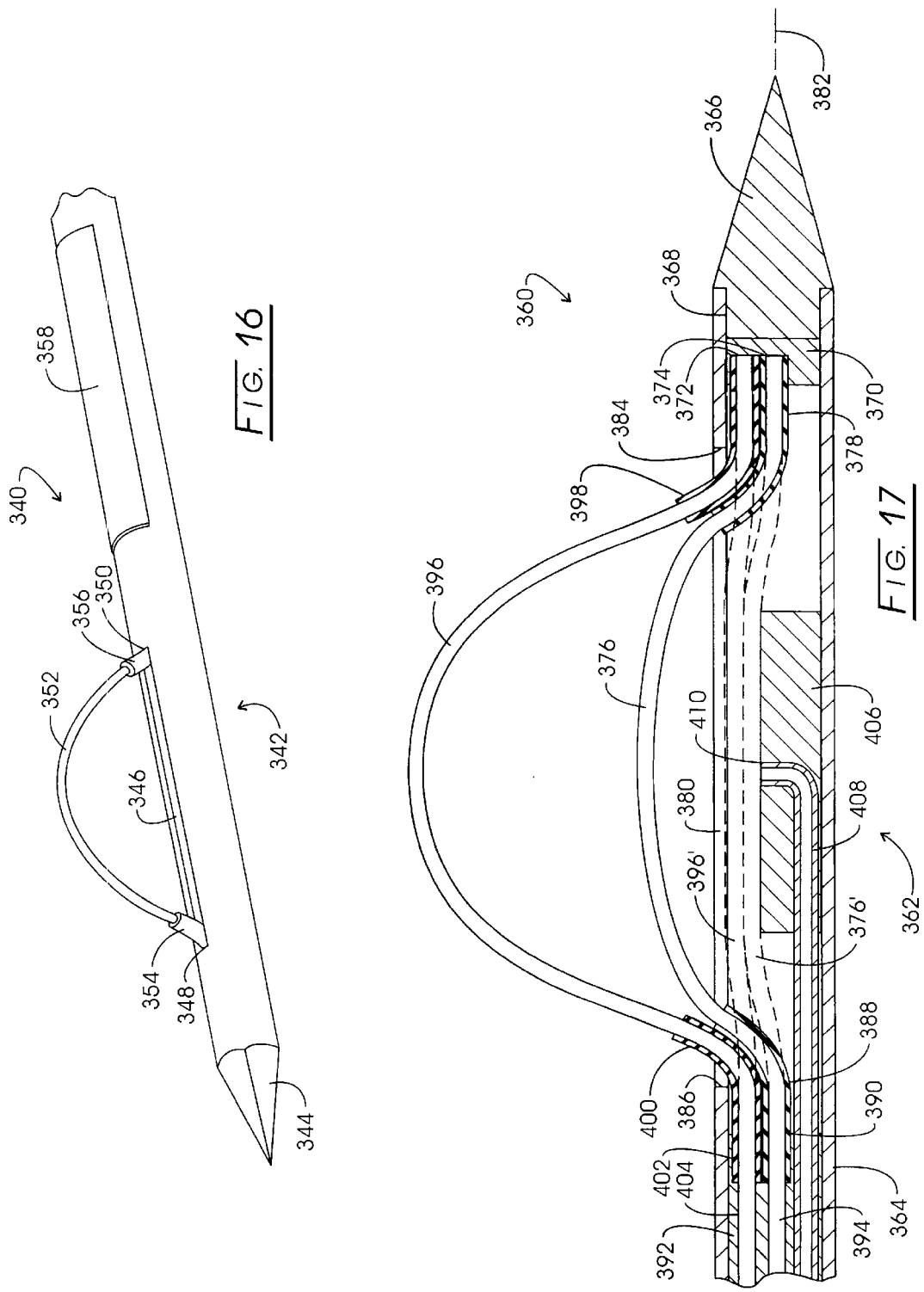

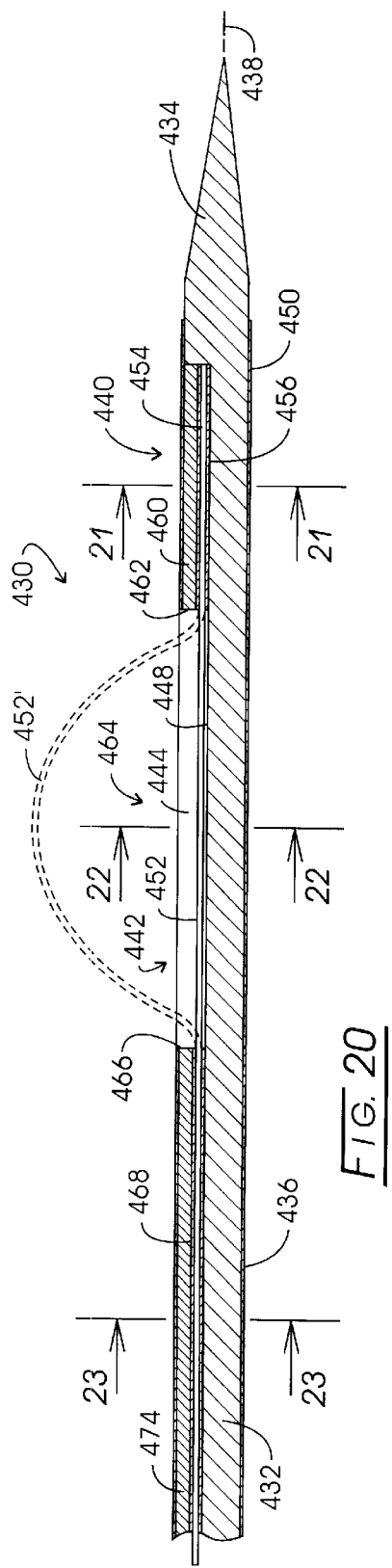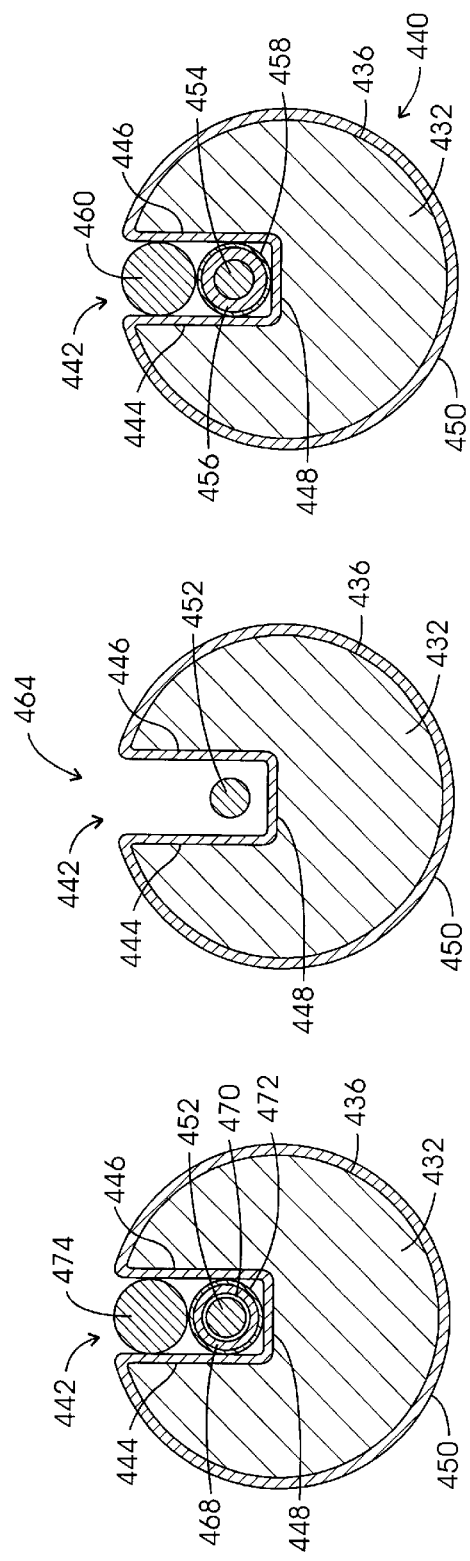

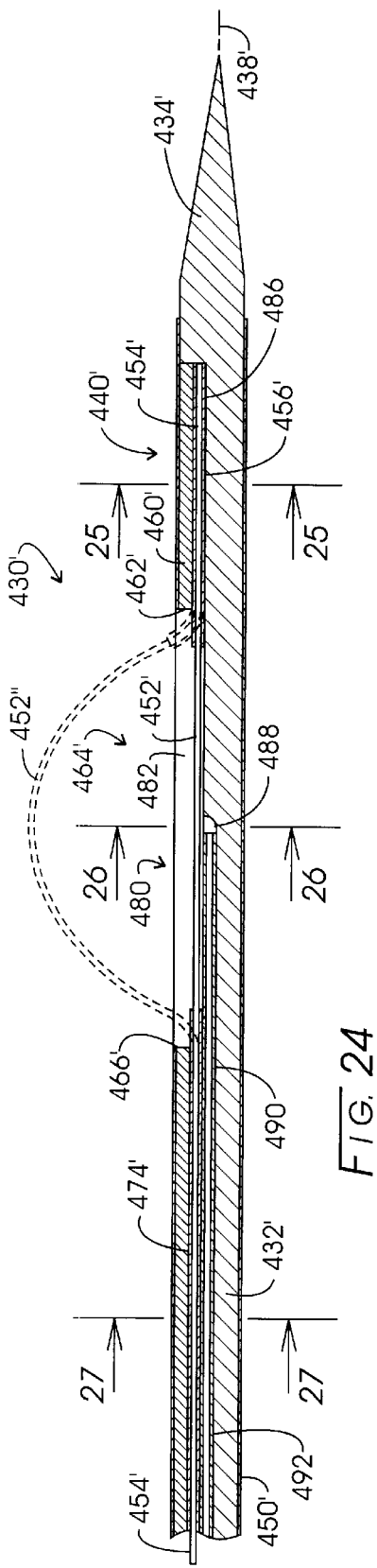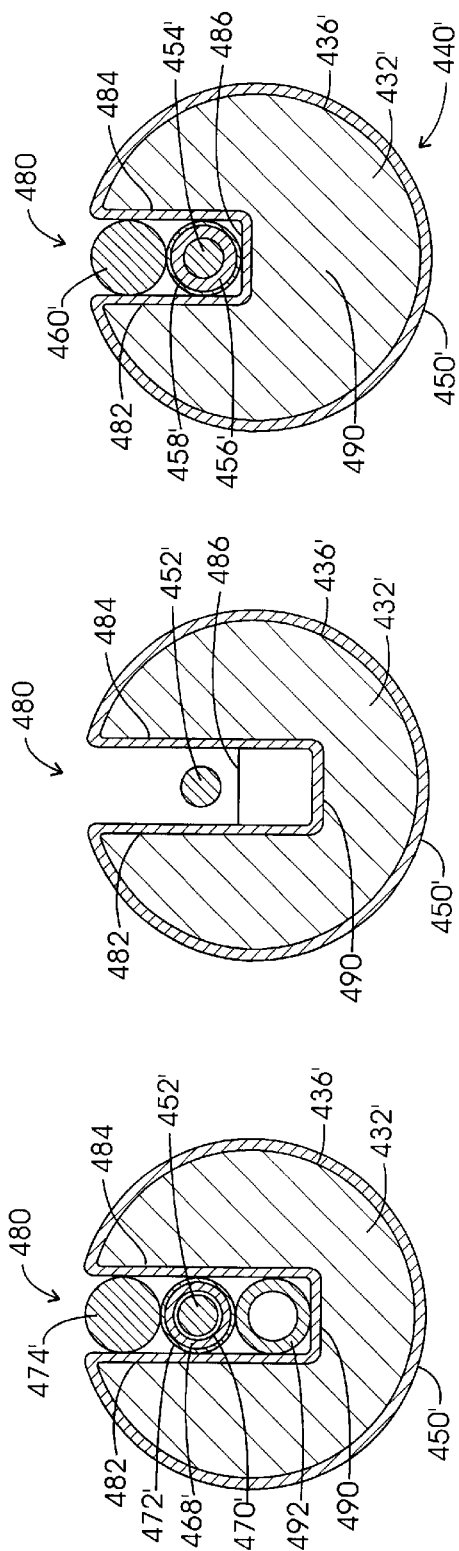

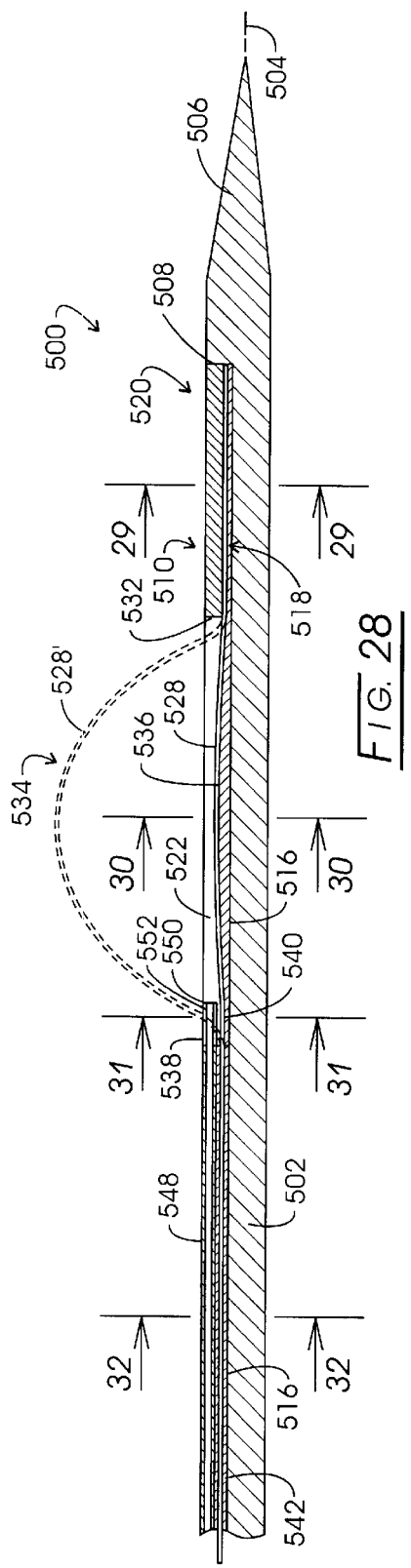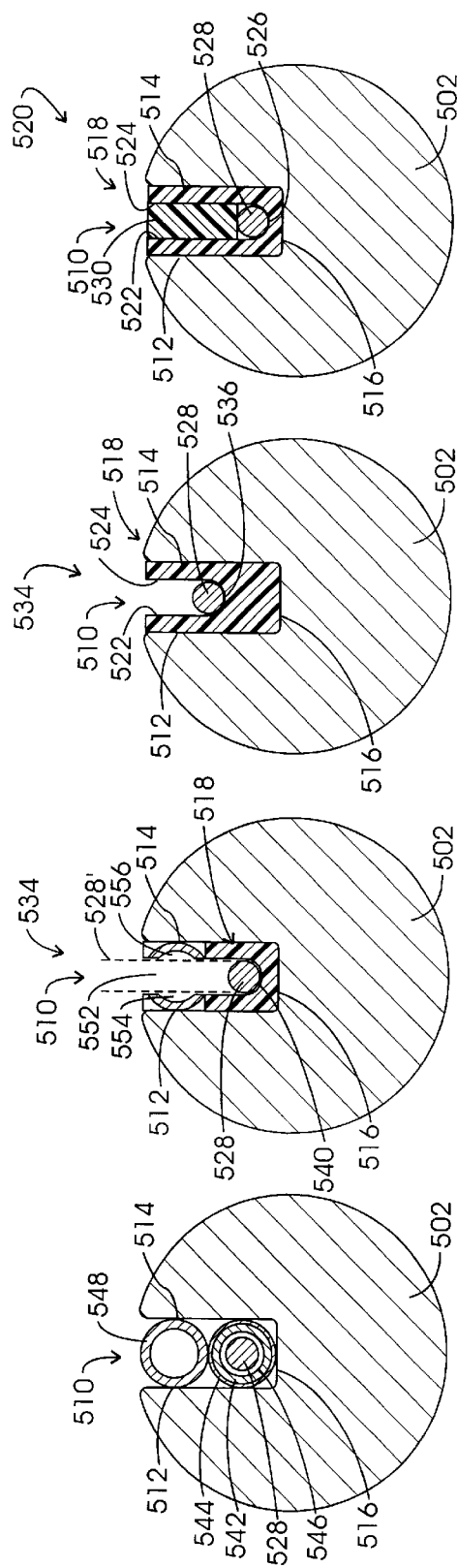

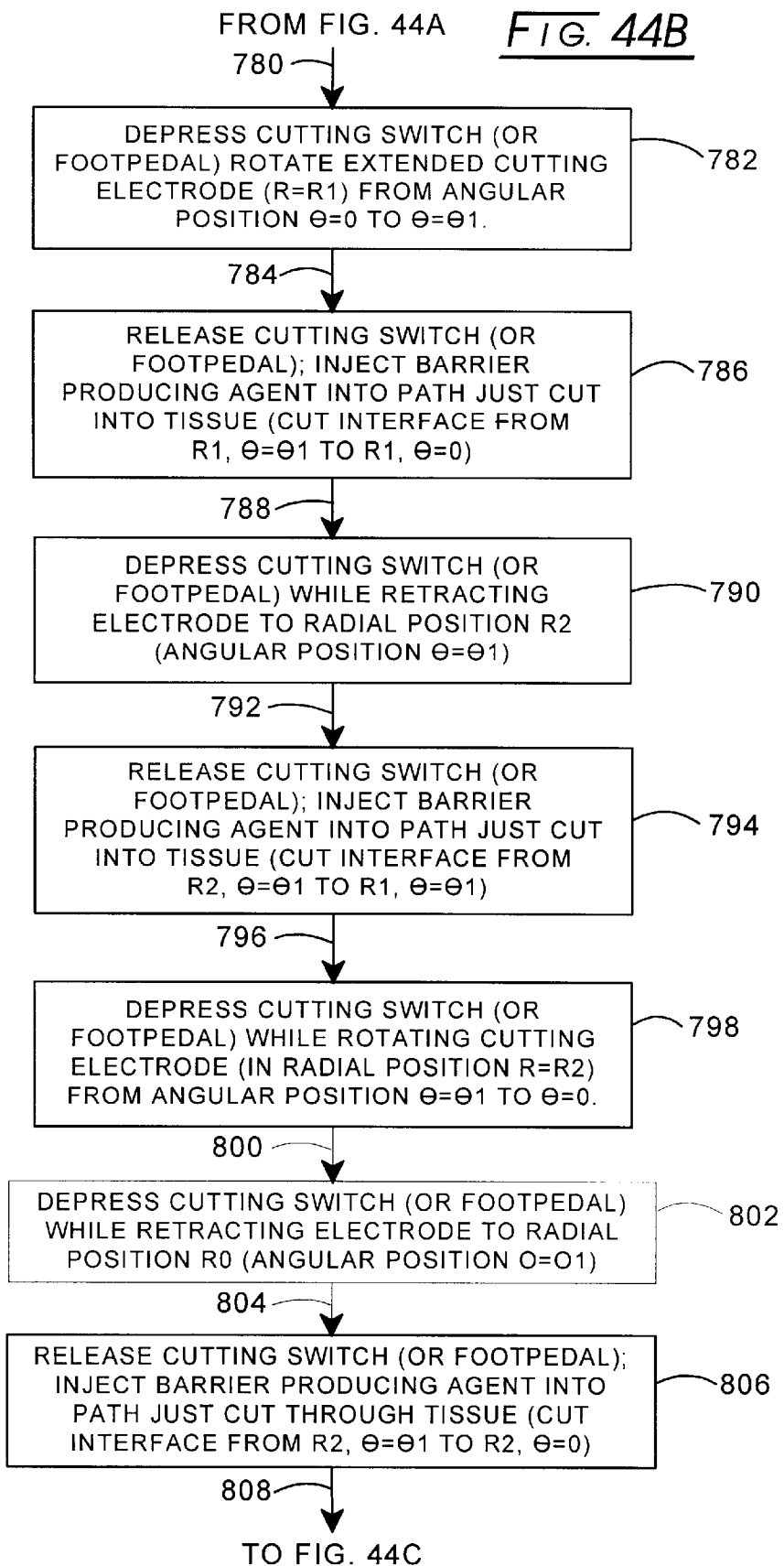

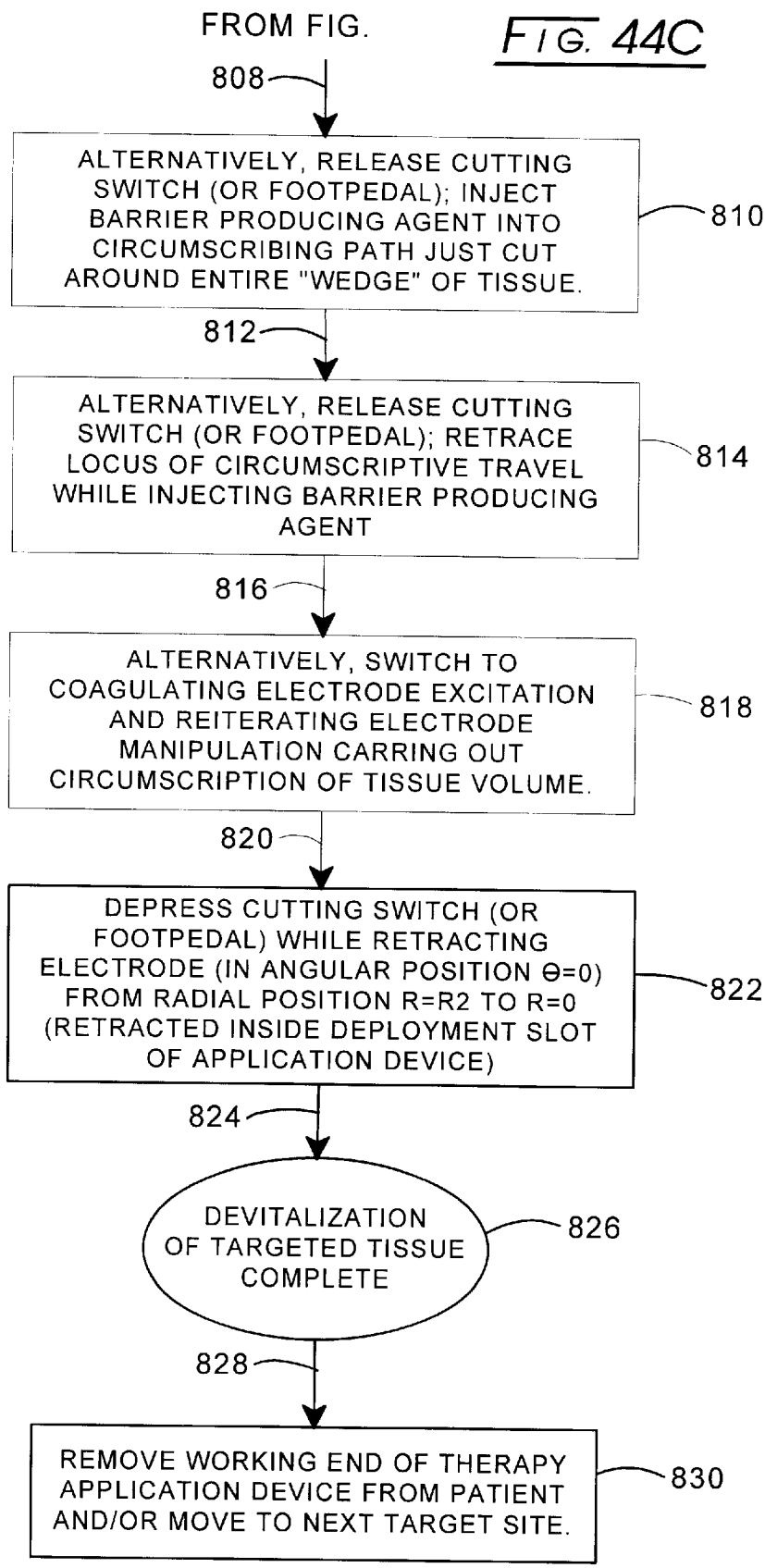

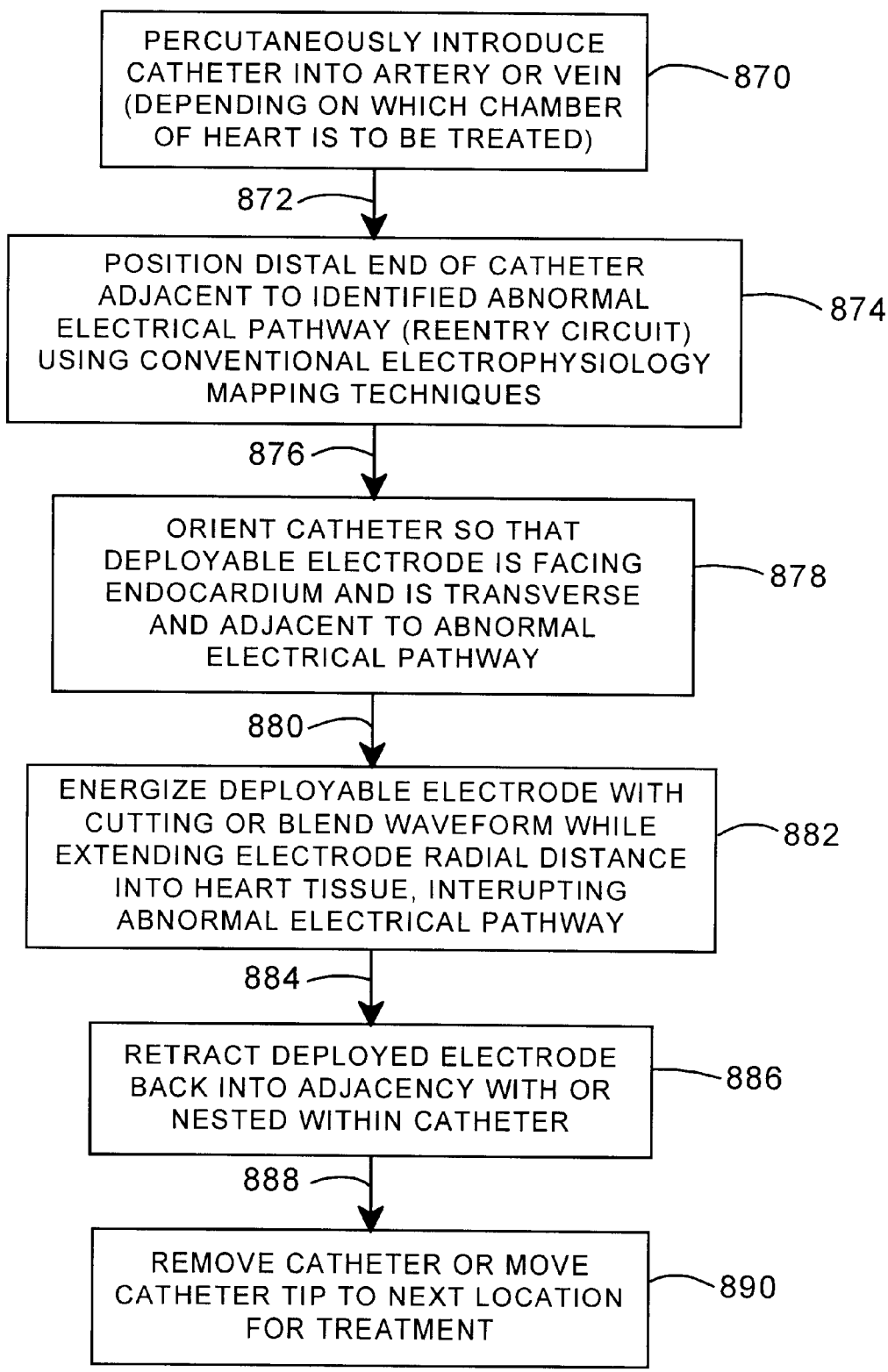

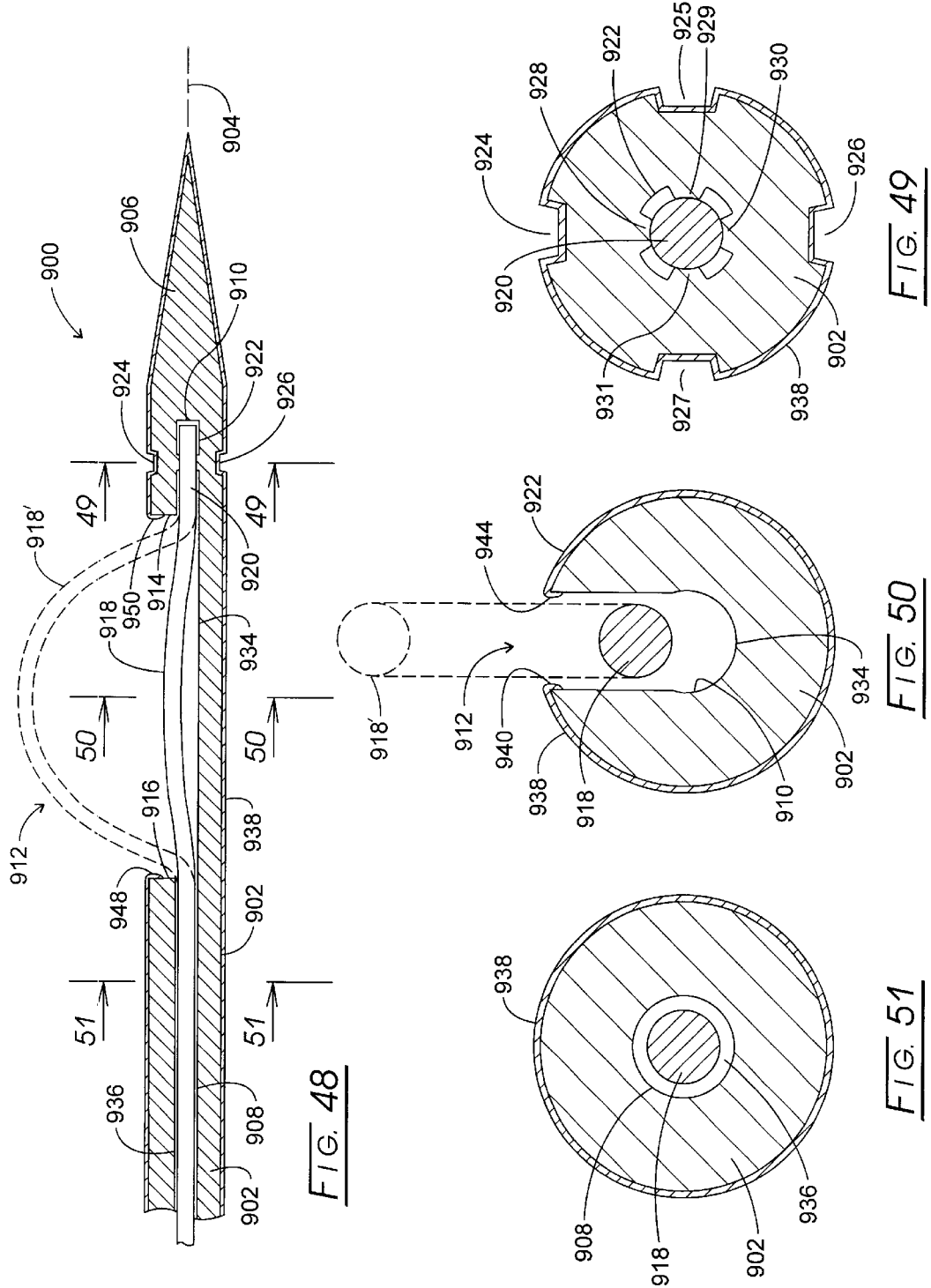

ACCURATE CUTTING ABOUT AND INTO TISSUE VOLUMES WITH ELECTROSURGICALLY DEPLOYED ELECTRODES

CROSS-REFERENCE TO RELATED APPLICATIONS

None

STATEMENT REGARDING FEDERALLY SPONSORED RESEARCH

Not applicable.

BACKGROUND OF THE INVENTION

The excision of diseased or abnormal tissue from the body traditionally has been termed an "invasive" one. In carrying out invasive surgery, medical practitioners generally have resorted to the use of sharpened edge tools and, for about six decades, additionally, forms of electrosurgery. In the latter regard, a somewhat pioneer electrosurgical device was developed by William T. Bovie. This early device, described, for example, in U.S. Pat. No. 1,813,902 issued on Jul. 14, 1931 entitled "Electrosurgical Apparatus" and its successors have met with acceptance over the years within the surgical community to the extent that current versions are referred to as the "Bovie".

For both traditional excision approaches, injury generally occurs to surrounding or peripheral and healthy tissue. While certain of such injuries are apparent, others have been reported which are more subtle. Conventional removal of malignant tumor, as well as more simple biopsy procedures have been reported to generate "seeding" or spreading or metastasizing cancer in the body. In addition to patient discomfort and longer recovery periods, more invasive surgical procedures are reported to be accompanied by a period of immunosuppression, a condition increasing the risk of disease spread. See the following publications in this regard:

"Impaired Production of Interlukin-2 after Surgery," T. Akiyoshi, et al., Clin. Exp. Immunology, Vol. 59, pp 45–49, 1985.

"The Influence of Surgical Operations on Components of the Human Immune System," T. Lennard, et al., British J. of Surgery, Vol. 72, pp 771–776, 1985.

Less invasive alternatives to conventional surgical procedures have been and continue to be investigated, particularly as the clinical detection of tumor or tissue abnormalities has become more refined. For example, current imaging systems (mammography, ultrasonographs, MRI) may detect and locate very small tumor or tissue abnormalities sized at the level of a millimeter. Where such tumor is detected, for example, in the breast, biopsy procedures employing fine needle aspiration techniques may be utilized. Retrospective investigation, however, has determined that about 80% of such biopsied tissue is benign. Where malignancy is determined, the biopsy procedure risks the above-noted seeding or metastasization opportunities. Excision of even the smaller aberrant tissue zones typically is both traumatic to the patient and relatively cost intensive. The latter cost aspect also is present with conventional needle biopsy procedures.

Particularly where small tumors or tissue abnormalities are encountered, investigators have looked to potentially less invasive and thus less costly and less traumatic procedures. For example, if a smaller tumor can be biologically destroyed in situ so as to become ischemic or necrotic, the resultant small zone of dead tissue eventually will be physiologically eliminated by resorption.

One approach to carrying out an in situ destruction of such smaller targeted tissue zones has been to thermally affect the volume of aberrant tissue. Such an approach may involve either cooling or heating the target tissue to the point of irreversible cell death or necrosis. For the former, cooling approach, reference is made to following publication:

"Requisites for Successful Cryogenic Surgery of Cancer," H. Neel, et al., Arch. Surg., Vol. 102, pp 45–48, 1971.

The latter approach, that of inducing therapeutic hyperthermia generally is a less invasive one. A rather broad variety of technical modalities have evolved to elevate the temperature of tissue. For example, biological tissue volumes may be heated by inductive, radiant, contact or joulean based techniques. While these hyperthermic approaches exhibit potential advantage over the highly invasive surgical modalities, limitations to their use have been identified. Inductively based systems, certain of which are described in U.S. Pat. Nos. 5,251,645 and 4,679,561 perform by passing high frequency electromagnetic radiation through tissue. This is achieved by passing the radiation between two external electrodes positioned adjacent the patient's skin. A drawback of such an approach to therapeutic hyperthermia resides in the heating of a relatively large volume of tissue at elevated temperatures for extended intervals of time. Typically with this practice, tissue is heated to temperatures of 6° C. to 10° C. above normal body temperature for periods of twenty minutes or more to achieve necrosis. The systems generally do not allow the volume of tissue to be well defined, i.e., the treatment is inaccurate, resulting in either insufficient necrosis or excessive necrosis extending into surrounding healthy tissue. As a consequence, practitioners have looked to combining prolonged heating of tissue with chemotherapy or radiation therapy modalities.

Interstitial thermotherapy has become an important alternative to invasive surgical methods. In general, six thermotherapy modalities have been developed for heating or cooling tissue. They are identified as: (1) radiofrequency heating, (2) microwave heating, (3) laser heating, (4) ultrasound heating and (5) cryogenic cooling. Radiofrequency heating procedures are categorized as direct and indirect. The latter, indirect, approach involves the placement of metal wires or pellets (which may be autoregulated) in the target tissue and then externally applying an R.F. field.

The above six modalities involve either of two methods of temperature alteration in tissue, to wit, conduction and diffuse or distributed heating of targeted tissue. Conduction may be of heat from or to a device or instrument and is characterized as a slow process since thermal diffusion through tissue is a somewhat slow phenomenon. This can lead not only to longer treatment periods but uncertainty in the size and shape of the final lesion, again a problem of treatment accuracy. Such conduction-limited modalities include: indirect radiofrequency heating, laser heating, and cryogenic cooling. Conduction-limited therapeutic heating of tissue using radiant sources is described, for example, in U.S. Pat. Nos. 5,284,144; 4,872,458; and 4,737,628. Radiant sources, such as lasers, produce localized heating of tissue, but do not permit the affected volume to be predetermined, a priori. Other conduction-limited contact heating approaches have been used for inducing therapeutic hyperthermia as are described in U.S. Pat. Nos. 4,979,518; 4,860, 744; 4,658,836; and 4,520,249.

Diffuse or distributed heating of targeted tissue is distinctly different from the above-described conduction-limited method. This approach has the potential advantage that the target tissue can be heated to a desired cauterization temperature within relatively shorter interval of time. Cauterization procedures involve bringing targeted tissue to a temperature within a predetermined temperature range for a duration resulting in irreversible cell death. However, while representing a procedure exhibiting much promise, investigators have encountered obstacles in its implementation. In this regard, the volume of tissue cauterized is generally more difficult to control for systems incorporating microwave or ultrasound procedures, inasmuch as these procedures depend upon the radiation of tissue-heating energy into a volume of tissue from an emitting transducer or antennae system. The precise size of any resulting lesion depends upon the duration of treatment as well as the microwave or ultrasound responsiveness of the targeted tissue. In this regard, investigators have looked to the placement of one or more temperature sensors within the treatment field or have looked to the measurement of electrical impedance to assess the extent of the volume of cauterized tissue to determine an end point termination of the therapy. The problem of treatment accuracy again is posed. See generally, U.S. Pat. Nos. 5,122,137; 4,776,334; and 4,016,866. A direct measurement of tissue impedance is described, for example, in U.S. Pat. Nos. 5,069,223 and 4,140,109. These procedures are complex and somewhat costly. Of the diffuse or distributed heating approaches, electrosurgical techniques hold promise for both precise and predictable cauterization of targeted tissue volume, as well as a rapidity of the treatment process. Devices and technology representing this category are described, for example, in U.S. Pat. Nos. 5,728,143; 5,683,384; 5,672,173; 5,672,174; 5,599,346; 5,599,345; 5,486,161; 5,472,441; 5,458,597; 5,536,267; 5,507,743; 4,486,196; 4,121,592; and 4,016,886. See also, PCT Application WO 96/29946.

Electrosurgical instruments generally perform in either of two operational modes, monopolar or bipolar. In the monopolar mode, electric current is conducted between a relatively small active electrode and a large return electrode located a distance from the active electrode. Because in the monopolar mode, current density in tissue decreases as the square of the distance from the active electrode, it is more difficult to treat more than very minimal volumes of targeted tissue as well as to maintain the volumetric accuracy of such treatment. Notwithstanding such a surface related operational limitation, the monopolar devices are quite efficient as electrosurgical cutting tools and for the purpose of carrying out a coagulation at the surface of tissue being cut. Each approach involves a different waveform but both are surface related and involve a modicum of arcing between the instrument tip and the tissue being affected.

The bipolar mode of electrosurgical (joulean) heating involves passing current between tissue disposed between two electrodes of similar surface area. To effect cauterization of targeted tissue, this electrosurgical heating technique has been implemented with instruments which deploy pointed, flexible fine wire or needle-like electrode-functioning stylets directly into the targeted tissue. This calls for a mechanical system carrying out tissue penetration with these fine deployed stylets which necessarily will have a small surface area per unit length of the electrode. As a consequence, the permissible current flux flowing between the electrodes is significantly limited inasmuch as excessive current densities will cause desiccation of tissue immediately adjacent the electrodes which defeats the procedure. This follows, inasmuch as the desiccated tissue adjacent the electrode will then exhibit a very high electrical impedance which prevents further tissue heating and thus limits the volume of tissue which can be treated to the point of effective cauterization. For this reason, the fine needle or stylet techniques heretofore employed have been observed to require a treatment duration of ten to fifteen minutes for larger lesions. Further, a temperature monitoring of the fine electrode and even the infusion of conductive fluids is called for to reduce impedance between the electrodes and surrounding tissue. Additionally, practice with the needle extruding mechanisms have shown them to be difficult to deploy, the practitioner having less than desirable information as to the exact positioning of the fine electrode stylets. For example, these wires will deflect in the procedure of insertion into the targeted tissue in dependence upon their degree of flexibility as well as upon the varying density characteristics of abnormal tissue sought to be cauterized. Placement identification or observation procedures using conventional imaging systems is hindered because of the highly diminutive surface area of the electrodes themselves. In this regard, such imaging systems fail to "see" the electrodes. As a consequence, the targeted tissue is either under-treated or the treatment procedure extends cauterization excessively into adjacent healthy tissue, i.e., it encroaches excessively beyond the targeted tissue volume. Treatment accuracy again remains problematic. Bipolar mode electrosurgical procedures are described, for example, in U.S. Pat. Nos. 5,720,744; 5,403,311; 5,122,137; 4,920,978; 4,919,138; and 4,821,725, while fine needle electrode technologies are set forth, for example, in U.S. Pat. Nos. 5,470,309; 5,370,675; 5,421,819; 5,470,308; and 5,607,389.

Investigators also have looked to the destruction or control of tumor by the devitalization or vascular interruption of oxygen and nutrient ingress to targeted tissue volumes. Resultant cell death or necrosis again may be accompanied by its physiologically natural absorption by the body. As before, while this general approach to tumor management holds promise, the practical aspects of control over the targeted tissue volume using minimally invasive tactics has remained elusive. See generally; Denekamp et al., "Vascular Occlusion and Tumor Cell Death," Eur. J. Cancer and Clinical Oncology, Vol. 19 No. 2, pp 271–275 (1983).

As is essentially the case in all remotely guided procedures, the process for carrying out an incision for example, of a volume of targeted tissue is difficult. This difficulty is particularly in evidence where an incision is called for which does not invade the targeted tissue volume, extending only about its periphery.

Highly controlled and accurate RF electrosurgical cutting promises to enjoy a number of surgical applications beyond topics such as vascular isolation of tissue volume. For example, rather basic intravascular catheter guided monopolar electrodes have been employed as therapy for a variety of cardiac dysrhythmias. The therapy involves maneuvering of a monopolar electrode to sites of arrhythmogenic myocardium to carry out an ablation of heart muscle at discrete areas. While the therapy has demonstrated high therapeutic effectiveness, the treatment procedure is somewhat primitive, substantial volumes of tissue at the inner wall of the heart being destroyed until the aberrant conduction pathway is eliminated or blocked by the resultantly necrosed tissue. R. F. catheter ablation techniques also have been used to treat ventricular tachycardias, atrial flutter, ectopic atrial tachycardia, and sinus node reentry, albeit with lower success rates. These techniques are still evolving and, as is apparent, a technique for accurately forming a controlled linear lesion of known and minimal dimension will represent a beneficial advance in the therapy. See generally: Wood et al, Radiofrequency Catheter Ablation for the Management of Cardiac Tachyarrhythmias, Am J Med Sci 1993;306(4): 241–247.

BRIEF SUMMARY OF THE INVENTION

The present invention is directed to the system, apparatus and method for accurately cutting about and into tissue volumes with electrosurgically deployed electrodes. The electrode employed with the instrumentation is electrosurgically excited during the act of its deployment with respect to two, spaced apart support positions. By using two such positions, the instrument design takes advantage of the inherent structural integrity of the arch. To implement this approach, a thin, resilient elongate electrode is mounted within the forward end region of a support member such that its distal end is fixed to the instrument while it extends longitudinally rearwardly. Within the forward end region, the electrode extends within a deployment slot, the sides of which, in turn, extend between a forward location adjacent the instrument tip and a rearward location. The sides of the deployment slot in combination with a compression-based mounting arrangement serve as structurally supportive abutments to the arch formation developed as the electrode is outwardly deployed by urging it forwardly into a compression stabilized arch. Control over the extent of deployment is provided by the corresponding extent of the forward movement of the electrode. Thus a highly stable compressed electrode arch configuration is developed with a repeatable and reliable profile which is substantially immune from deformation which otherwise might occur during the carrying out of electrode cutting maneuvers pushing the sidewise extent of the electrode through tissue.

The accuracy and repeatability achieved with the instant system has important applicability to procedures for carrying out the circumscriptive vascular isolation of a targeted tissue volume such as a tumor. Because the arch shaped electrode is electrosurgically excited for cutting both during its deployment and retraction, a combination of those maneuvers with a relatively simple pivoting of the forward end region of the instrument permits the devascularization of such tissue to occur without the instrument touching that targeted tissue volume itself. With the system, typically a volume of targeted tissue such as tumor is isolated by a cut providing necrotic interfacing cut surfaces having a resultant circumscribing volume shape resembling a segment of an orange. A desirable repeatability of the geometric pattern cut with the system permits an iteration of the maneuvering procedure utilizing the coagulating output of the associated electrosurgical generator. Thus, the devascularization or dearterialization of the targeted tissue volume may be enhanced with beneficial elimination of any bleeding which might occur. Generally within minutes, the isolated targeted tissue volume will begin to experience cell death and over a period of time, the natural functioning of the body may resorb it.

The accurate cutting achieved also permits the very accurate positioning or deposition of a barrier within the interface defined by the circumscriptive cut carried out with the arch shaped electrodes. Such barriers will contribute to the assurance that the targeted tissue volume is fully isolated from surrounding vital or healthy tissues to an extent beneficially restricting the rate of any neovascularization in addition to the accurate positioning of barrier substances or fluids at the noted cut interface. The structurally robust mounting of the electrode configuration also permits it to draw a membranous barrier shroud through the cut interface to carry out the noted additional isolation of targeted tissue.

In the discourse to follow, the term "barrier" is referred to in the description of a variety of instrumentation embodiments. Such barrier components may be chemical agents functioning to slow down a revascularization process by increasing the depth of necrotic tissue which such neovascularization must span. Necrotising agents are selected for suitable localized administration and may include chemotherapeutic agents as well as alcohol and the like. The term "barrier" also is used in a physical sense to function to slow down revascularization through utilization of resorbable mesh or membranes, adhesives and various anti-adhesion barriers. A variety of barrier agents and devices are described in the discourse to follow.

The accuracy and stability of the electrode system also lends it utility to the electrosurgical treatment of atrial flutter. In this regard, rather than the relatively uncontrolled electrosurgical ablation procedures currently practiced, the arch shaped electrode can be incorporated at the tip of an intravascular heart catheter for positioning against the interior heart wall at a location transversely intercepting the current path of that reentry current intended to be interrupted. The electrode then is deployed while being electrosurgically excited to perform an accurate linear cut with cut tissue sides providing a necrotic tissue interface functioning to interrupt the current path in avoidance of atrial flutter. In effect, treatment is achieved with substantially reduced damage to the heart wall.

Other objects of the invention will, in part, be obvious and will, in part, appear hereinafter. The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 2 is a perspective view of the forward end region of an instrument illustrated in FIG. 1:

FIGS. 3A–3E are schematic sectional views taken through the plane 3—3 in FIG. 2 and illustrating one sequence of vascular isolation maneuvers for the instrument of FIG. 2;

FIG. 5 is a perspective view of the forward end region of the instrument shown in FIG. 1;

FIGS. 6A–6C are schematic sectional views taken through the plane 6—6 in FIG. 5 and illustrate another maneuvering arrangement of the instrument of FIG. 5;

FIG. 7 is a partial sectional view of the front end region of the instrument shown in FIG. 1 illustrating an electrode therein in a retracted orientation;

FIG. 12 is a sectional view of the front end region of the instrument of FIG. 1 illustrating an electrode in a deployed orientation;

FIG. 15 is an electrical block diagram of a control assembly employed with the system of the invention;

FIG. 16 is a pictorial view of the forward end region of an instrument according to the invention showing the presence of a surface mounted return electrode;

FIG. 17 is a partial sectional view of the forward end region of an instrument according to the invention showing a dual electrode configuration;

FIG. 20 is a sectional view of the forward end region of an embodiment of the instrument of the invention showing an electrode deployment in phantom;

FIG. 21 is a sectional view taken through the plane 21—21 in FIG. 20;

FIG. 22 is a sectional view taken through the plane 22—22 in FIG. 20;

FIG. 23 is a sectional view taken through the plane 23—23 in FIG. 20;

FIG. 24 is a sectional view of the forward end region of another embodiment of the instrument of the invention showing a deployed electrode in phantom;

FIG. 25 is a sectional view taken through the plane 25—25 in FIG. 24;

FIG. 26 is a sectional view taken through the plane 26—26 in FIG. 24;

FIG. 27 is a sectional view taken through the plane 27—27 in FIG. 24;

FIG. 28 is a sectional view of the forward end region of another embodiment of the instrument of the invention, showing a deployed electrode in phantom;

FIG. 29 is a sectional view taken through the plane 29—29 in FIG. 28;

FIG. 30 is a sectional view taken through the plane 30—30 in FIG. 28;

FIG. 31 is a sectional view taken through the plane 31—31 in FIG. 28;

FIG. 32 is a sectional view taken through the plane 32—32 in FIG. 28;

FIGS. 44A–44C combined as labeled thereon to provide a flowchart showing methodology of the invention;

FIG. 47 is a flowchart showing methodology of the invention associated with the embodiment of the FIGS. 45 and 46;

FIG. 48 is a partial sectional view of the front end region of another embodiment of the instrument of the invention;

FIG. 49 is a sectional view taken through the plane 49—49 in FIG. 48;

FIG. 50 is a sectional view taken through the plane 50—50 in FIG. 48; and

FIG. 51 is a sectional view taken through the plane 51—51 in FIG. 48.

DETAILED DESCRIPTION OF THE INVENTION

The highly accurate and controllable electrosurgical cutting feature of the invention has particular applicability to minimally invasive surgical procedures. Incisional accuracy is achieved with cutting components over which dimension is controlled during their manipulation and as a consequence of their structural stability. In the latter regard, the instruments employ the inherent structural integrity of the arch. Such two position support of fine cutting electrodes permits surgical cutting procedures to be carried out within an advantageously shorter interval of time. In one modality of its use, a small tumor, for example, having a diameter of less than about one-half cm which has been discerned for example, by mammography and/or ultrasonography, is not subject to conventional biopsy procedures. Such tumors or abnormalities, for 80% of their occurrences, will be benign. Where a biopsy procedure, for example, needle biopsy is employed, where the tumor is malignant, seeding risks are present. With the present approach, the periphery of the tumor or abnormality is accessed with a fine wire-like instrument and by employing electrosurgical cutting, the small abnormal region is vascularly isolated. In particular, the dearterialization occurring with such isolation induces complete cell death throughout the interior of the circumscribed volume within hours due to lack of oxygen and nutrients. Subsequently, over a period of time, the body may resorb the dead tissue. The diminutive instrumentation employed for this procedure is relatively inexpensive when compared with conventional biopsy procedures and is quite minimally invasive. To assure effective devascularization, a surface coagulation or preferential surface deposition of electrical heating additionally can be carried out either as a subsequent step or utilizing a "blend" waveform simultaneously accomplishing both electrosurgical cutting and surface coagulation. Another approach to assuring devascularization provides for the formation of a barrier layer at the interface of an electrosurgical cut. This layer may be in fluid or membranous form.

Figure 1:
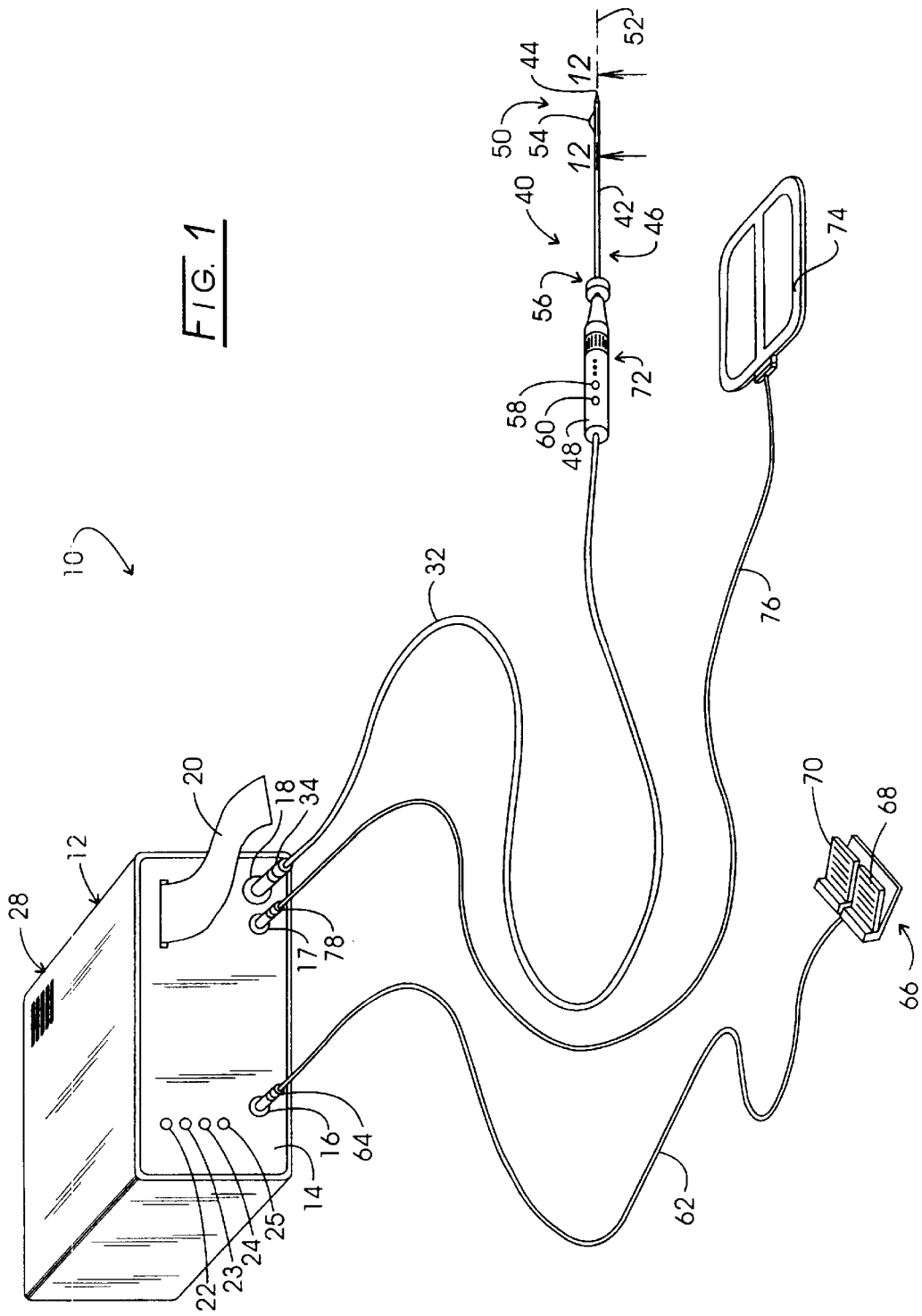
FIG. 1 is a perspective view of one embodiment of the system of the invention.

Referring to FIG. 1, one embodiment of the apparatus and system for carrying out the vascular isolation modality of the invention is represented generally at 10. System 10 includes a customized electrosurgical generator and control arrangement represented generally at 12. The assembly 12, has a forward panel 14 at the lower level of which are provided three connector receiving receptacles 16, 17 and 18. Above the latter two receptacles is a paper strip 20 extending outwardly through a slot behind which is positioned a printer assembly (not shown). Visual cueing through the media of selectively energized light emitting diodes (LED) is provided at panel 14 as represented at 22–25. Finally, rearwardly upon the generator assembly 12 is an audio grill 28 through which aural cueing signals are broadcast.

A control assembly cable 32, having a connector 34 is shown extending from an electrical connection with receptacle 18. The instrument or electrosurgical cutting apparatus of the invention is represented generally at 40. Instrument 40 is seen to include an elongate support member represented generally at 42 which extends between a tip 44 and a base or rear region 46. Base region 46, for the instant embodiment, is configured to attach to a removable handle for manual positioning of the instrument 40. In this regard, the support member 42 and associated components may be a disposable item, while the handle 48 and its associated components may be sterilizable or disinfected and reusable. Located inwardly from the tip 44 is a forward end region 50 which extends along a longitudinal axis 52 from the tip 44 and, during an insertion mode of operation, the forward end region 50 of the instrument 40 is positioned in adjacency with the peripheral extent of the tissue volume to be vascularly isolated by circumscription. In this regard, the tip 44 and support member 42 are not inserted into the target tissue volume but into normal or healthy and viable tissue immediately next to the peripheral extent of the volume of targeted abnormal tissue.

Seen extending outwardly from a deployment portion of the forward end region 50 is a thin, resilient electrode 54 having an arch shaped configuration. During the positioning into or removal of the instrument 40 from the tissue, the electrode 54 is retracted into a nested orientation within a deployment portion of forward end region 50. Actuation of electrode 54 to its deployed orientation, as well as retraction therefrom for the instant embodiment is by an actuator assembly represented generally at 56.

Handle 48 is seen to support control button-type switches 58 and 60. Such switches are used to activate electrode 54 with, for example, surgical cutting current, a coagulation dedicated current or a blend of those two currents. As an alternate or supplementary arrangement, more remote switching may be provided. In this regard, a connector assembly cable 62 is shown having a connector 64 inserted in electrical communication with the receptacle 16 of generator assembly 12. Cable 62 extends to a foot pedal-type dual switch represented generally at 66 and having foot actuated switches 68 and 70.

Returning to the handle component 48, visual cueing devices such as light emitting diodes (LED) also may be provided as represented in general at 72. Electrode 54 operates in a monopolar fashion during performance carrying out electrosurgical cutting and for coagulation purposes. To provide a return for this form of cutting, a conventional remote patient return electrode is provided as shown at 74. Electrode 74, having an extended surface area, is applied to a surface of the patient's body and is seen connected to electrosurgical generator 12 by a cable 76 extending to a connector 78 which, in turn, is operatively inserted within the receptacle 17.

Upon power-up of the electrosurgical generator assembly 12, a component of the control thereof carries out a form of electrical interrogation of the instrument 40. In this regard, the electrosurgical cutting current waveform will vary in terms of peak-to-peak voltages within a range of about 500 to 3500 volts. This variance will depend upon the principal cross-sectional dimension or shape of the wire-shaped electrode 54. In effect, the electrosurgical cutting involves a highly concentrated or localized energy deposition and associated heating of tissue to sufficient levels to effect vaporization of cellular fluid. This causes the rupture of cell walls to carry out a "cut". An optimum coagulation waveform, on the other hand, is configured not to cut but to deposit electrical energy preferentially on the surface of the tissue. While coagulation waveforms exhibit a relatively higher crest factor, they are configured with a relatively high but short pulse followed by a damped waveform. A blend performance carried out by the assembly 12 combines the sinusoidal electrosurgical cutting waveform with the coagulation waveform. In general, the size and ultimate arch apex value of the electrode 54 will vary in accordance with the targeted tissue size. For the most part, that size will be quite small, i.e., less than about 2 cm in diametric extent. Accordingly, a desirable aspect of the invention is to provide an electrical parameter based code within the instrument 40 which is interrogated by the control system associated with the generator 12. Upon the interrogation of that code component, for example, LED 22 is energized to represent that the system is ready. Then the forward end region 50 of the instrument 40 is positioned within the patient adjacent the peripheral extent or boundary of the volume of targeted tissue. By depressing either foot pedal 68 of switch 66, or actuating the switch 58 on handle 48, the electrosurgical cutting procedure is initiated. As this occurs, the control within generator 12 energizes LED 23 to indicate an "energization" status and a distinct audible tone of an initial first frequency, for example, in the range of 800 to 1000 Hz, is generated and broadcast through the grill 28. The practitioner then actuates the instrument 40 at actuator assembly 56 to cause a gradual deployment of the electrode 54 from its nested original insertion mode orientation. The practitioner then manipulates the instrument 40 including the actuator control 56 to carry out a circumscriptive vascular isolation of the targeted tissue volume by electrosurgically cutting about its periphery with a procedure of outward electrode deployment, pivoting, and electrode retraction while cutting. Accordingly, the selection of the size of electrode 54, and in effect, support portion 42 generally is predicated upon the size of the targeted tissue at hand.

Turning to FIG. 2, the forward end region 50 of instrument 40 is shown at a higher level of detail. In FIG. 2, electrode 54 is seen deployed as a thin, resilient wire which has been extended as an arch from an outwardly open deployment portion or slot 80. The slot 80 extends from a forward location 82 to a rearward location 84 and adjacent those forward and rearward locations, the electrode 54 is seen to be insulated by respective insulative flexible tubes or sleeves 86 and 88. These sleeves 86 and 88, in conjunction with the slot surface form two, spaced apart abutments for structurally supporting the electrode arch. This arch structurally develops the strength and thus, dimensional integrity necessary for a pivoting, arc-defining locus of cutting movement to which the electrode 54 is subjected. Electrode 54 is deployed from its retracted, nested position within slot 80 by urging it forwardly in compression to effect outward movement generally transversely to the longitudinal axis 52 to an extent curving it into an outwardly depending arch formation as shown. During this procedure, electrosurgical cutting current is applied to the electrode so that it, in effect "cuts" its way into a deployed orientation. This same cutting activity is continued during a manipulation of the instrument 50 and the electrode 54 by pivoting or rotation as represented at curved arrow 90 about longitudinal axis 52 and by retraction of the electrode 54 to select location to vascularly isolate the volume of targeted tissue. A full circumscription of such tissue is achieved with the continuous electrode 54 as is represented in the maneuvering diagram set forth in FIGS. 3A–3E.

Looking to FIG. 3A, a section through forward end region 50 is shown as It intersects the electrode 54 at the apex of the arch defined by it upon being fully deployed. In the figure, the electrode 54 apex location is shown with that same numeration. The figure further reveals the slot 80, as well as a section of a deflector guide component 92. Electrode 54 is shown having been deployed to an apex radius R1 and having completed an electrosurgical cut to that radial extent as represented by the cut indicator line 94. This cut line 94 will reside in healthy tissue but in adjacency with the targeted tissue volume 102 peripheral extent. To carry out a circumscription of such tissue, instrument forward end region 50 will have been oriented angularly as shown and indicated by the angular designation θ=0. The deployment of electrode 54 is such that its apex will pass over the "top" of the targeted tissue 102. Looking to FIG. 3B, the fully deployed electrode 54 continues to be energized from its angular location θ=0 and the instrument forward end region 50 is pivoted about axis 52 to describe the arc-shaped cut surface represented at cut indicator line 96, the electrode 54 now being at an angular position θ=θ1 and at the continuing outer radius, R1. At this position, the electrode 54 will have cut over the targeted tissue volume 102 and will reside in adjacency with an opposite side of it. Looking to FIG. 3C, while the forward end region 50 is at the angular orientation θ=θ1, it is retracted toward the deployment portion 80 while carrying out electrosurgical cutting as represented by the cut indicator line 98. Retraction is halted, however, before electrode 54 becomes fully nested within the slot 80. At this location, the electrode will be within healthy tissue and adjacent the last or fourth side of the targeted tissue volume 102. As represented in the figure, its location radially is identified at R2 while its angular orientation remains at θ1.

The next maneuver is represented in FIG. 3D where, while remaining at the radially distance R2, electrode 54 is rotated or pivoted at the forward end region 50 from the angular orientation θ=θ1 to the initial angular orientation θ=0, full circumscriptive vascular isolation having been accomplished with the final cut represented at cut indicator line 100. The volume represented by such an electrosurgical cutting procedure will resemble a segment of an orange. Note in the figure that electrode 54 now is poised at the cut indicator line 94 and radially positioned above the slot 80. FIG. 3E reveals the final retraction of electrode 54 into the slot 80 in preparation for removal of the instrument 40 forward end region from its position of adjacency with the targeted volume of tissue. That tissue, having been vascularly isolated, will exhibit cell death within hours and ultimately may be resorbed into the body. Advantageously, the steam (i.e, boiled cellular water) generated during the maneuver illustrated in FIGS. 3A through 3E escapes along the interface between the cylindrical surface 120 of instrument 40, effecting heating and cauterization of tissue adjacent that cylindrical surface 120, thereby further minimizing the possibility of needle-track metastasis.

The practitioner is afforded additional options in connection with the instant procedure. In this regard, the locus of cutting activity of the electrode 54 may be reiterated while carrying out a coagulation of the tissue immediately adjacent the electrosurgically defined cut, i.e., at the cut tissue interface. Alternately, the cut itself may be made with a blend mode of operation of the electrosurgical generator 12 such that a cutting activity is combined with a coagulation activity. Additionally, the instrument 40 may be configured to express a cauterizing fluid, a barrier fluid or deploy a barrier shroud at the tissue interface represented by the cut indicator lines 94, 96, 98 and 100. Such an addition to the procedure inhibits the rate of any revascularization of adjacent cut tissue surfaces. It may be observed, however, that the electrosurgical cutting approach is one developing necrotic surface characteristics which inhibit or slows such revascularization.

Figure 4:
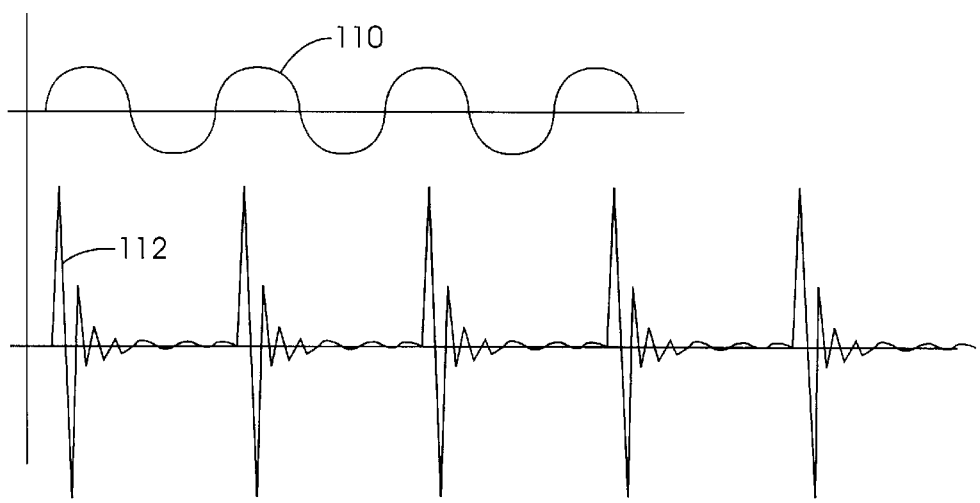
FIG. 4 is a stylized graph showing an electrosurgical cutting waveform and a coagulation waveform output of an electrosurgical generator.

Looking momentarily to FIG. 4 (below FIG. 14), a sinusoidal form of curve 110 is schematically illustrated with the purpose of describing a conventional electrosurgical cutting waveform. Because of this continuous waveform, a sustained arc is developed causing the above-noted intense localized heating and cell rupture at the point of impingement of the arc. This develops a cutting effect. Often, the good cutting achieved with waveforms as at 110 is accompanied by some bleeding in conventional electrosurgical approaches. The generators as at 12 then are provided with a coagulation mode of operation which is represented in the figure at 112. Note that this is a highly damped waveform with high peak-to-peak voltage excursions for short intervals. This waveform is not a cutting system but provides a preferential surface deposition of electrical heating to cause localized coagulation. The noted blend operation combines the outputs represented at 110 and 112.

A substantial application of the instant system is involved with tumor or abnormal tissue encountered in the breast. For the present system, where such tumor is quite small, for example, less than about 1 cm in diameter and more often, having a diametric extent of only a few millimeters, then an abbreviation of the procedural manipulation represented in 3A–3E becomes available to the surgeon. Looking to FIG. 5, the forward end region 50 of the instrument 40 is represented in the same manner as shown in FIG. 2 but with a section noted at 6—6. The manipulation of the instrument forward end region 50 for this abbreviated procedure is represented in conjunction with FIGS. 6A–6C. Looking to FIG. 6A, following the positioning of forward end region 50 into adjacency with one side of the targeted tissue volume 104, an angular orientation represented at θ=0, the electrode 54 is deployed to form an arch while being excited with electrosurgical cutting current. The resulting cut indicator line through healthy tissue but in adjacency with the targeted tissue volume 104 is represented at 114 extending to the radial distance R1 representing the radius at the apex of the arch configuration of the electrode 54. Next, as represented in FIG. 6B, the forward end region 50 is rotated about longitudinal axis 52 through the angular orientation θ=θ1 to describe a cutting surface locus represented at cut indicator line 116 which extends over or about a top side of the targeted tissue 104 peripheral extent. At the completion of that maneuver, the angular position θ=θ1 is reached. FIG. 6C shows that following the completion of the cutting of surface 116, electrode 54 is fully retracted while being excited for electrosurgical cutting as represented by cut indicator line 118. Retraction is into a fully nested orientation within the deployment portion or slot 80. However, that cylindrical surface 120 of the forward end region 50 will have severed the very small amount of tissue in adjacency therewith, particularly, with the rotation of the region 50. In general, this will be sufficient for evoking vascular isolation and consequent cell death. Of course, a necrotizing fluid, barrier fluid or sheath also may be employed with this abbreviated procedure. Following the retraction of electrode 54 to its nested orientation within deployment portion or slot 80, the forward end region 50 is removed from its position of adjacency with the targeted tissue.

Referring to FIG. 7 (above FIG. 12), a sectional view of the forward end region 50 of instrument 40 is revealed. In the figure, the tip 44 is shown to be configured having an annular shoulder 122 which is inserted within the forward end of the tubular support member or cannula 42. Tip 44 is seen to be configured as a trocar for purposes of penetration (percutaneous) through the patient's tissue. Positioned immediately rearwardly of the tip 44 is a cylindrical, electrically insulative electrode engagement block 124 having a rearwardly facing cylindrical opening therein 126 which adhesively receives both the electrode 54 and associated electrically insulative sleeve 86.

Figure 8:
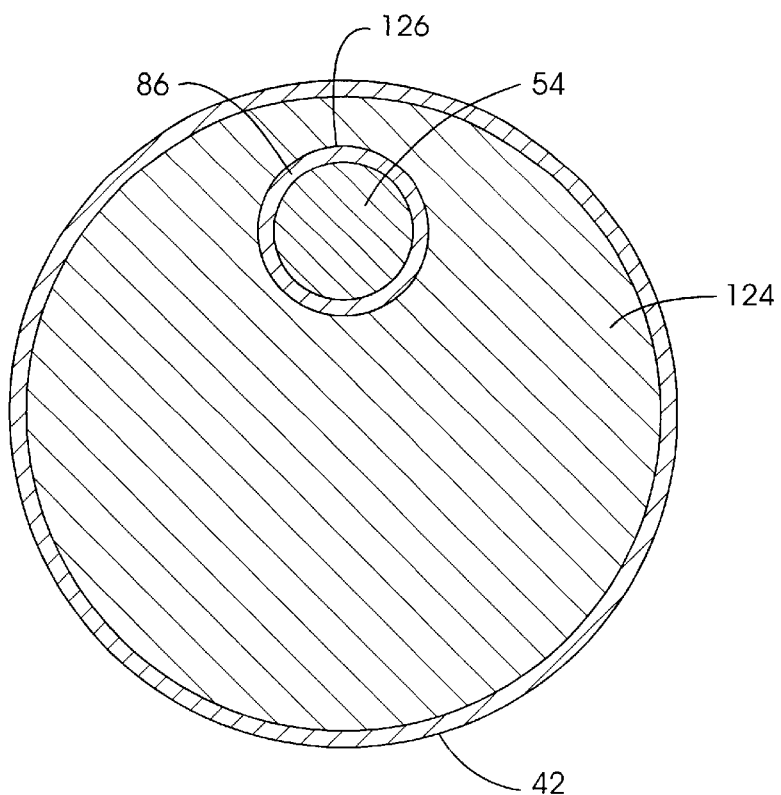
FIG. 8 is a sectional view taken through the plane 8—8 in FIG. 7.

Referring additionally to FIG. 8, a sectional view reveals the profile of the above-noted electrode engagement block 124 along with the opening 126 formed therein. Additionally, a sectional view of electrode 54 and insulative sleeve 86 is revealed.

Returning to FIG. 7, the electrode 54 is depicted in its retracted or nested orientation as is utilized during an insertion mode wherein instrument 40 is moved into adjacency with the volume of targeted tissue. This orientation also is employed in a removal mode wherein the instrument 40 is removed following a vascular isolation procedure. The figure further reveals the generally cylindrical deflector guide component 92 which functions to support electrode 54, as well as to provide an outward bias thereof at the commencement of its deployment. Shown extending within the guide component 92 is a tubular shaped fluid conduit 128 which has a fluid outlet 130 located within the deployment portion or slot 80. Outlet 130 is located such that a barrier fluid delivered from conduit 128 may be expressed therefrom and into contact with adjacently disposed electrosurgically cut tissue surfaces.

Figure 9:
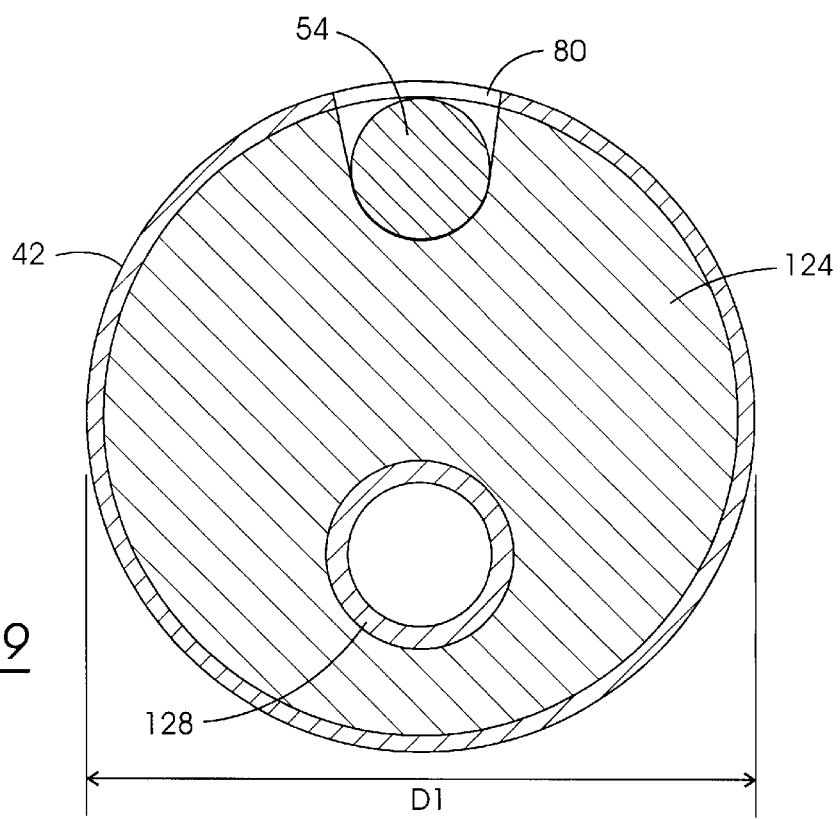
FIG. 9 is a sectional view taken through the plane 9—9 in FIG. 7.

Looking additionally to FIG. 9, a sectional view of the support member 42 at the position of deflector guide component 92 is revealed. It may be observed that the deployment portion or slot 80 at component 92 is configured as an inwardly rounded truncated trapezoidal elongate notch formed within component 124. FIG. 9 also reveals a cross section of the barrier fluid delivery channel 128. The support member 42 is shown as having an outer diameter, $D_1$. Returning to FIG. 7, electrode 54 is seen to extend rearwardly, whereupon it is slidably engaged by electrically insulative sleeve 88 which, in turn, is fixed within a cylindrical cavity 132. Cavity 132 extends rearwardly from the outer face 134 of a cylindrical, electrically insulative electrode guide and conduit support 136. Guide 136 is configured having a channel or lumen 138 through which the electrode 154 may slide. Being fixed within the interior 140 of support 42, the guide 136 additionally is formed having a cylindrical channel 142 for supporting the fluid conduit 128.

Figure 10:
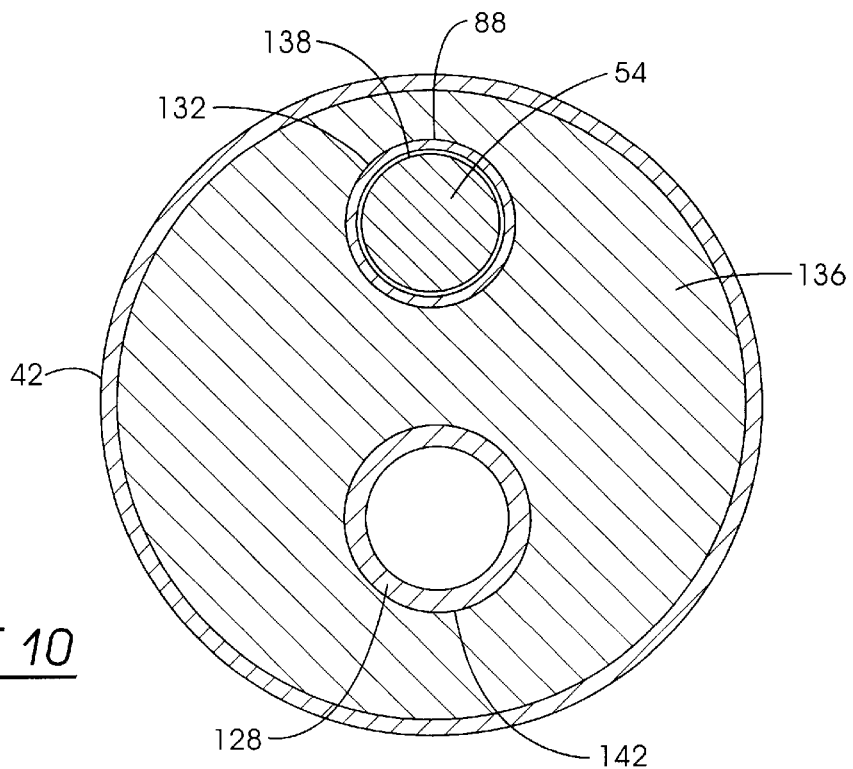
FIG. 10 is a sectional view taken through the plane 10—10 in FIG. 7.

Looking momentarily to FIG. 10, a sectional view of the above features adjacent face 134 of electrode guide 136 is provided. In the figure, it may be seen that the flexible insulative sleeve 88 is fixed within the cylindrical cavity 132 and that the electrode 54 is slidable within sleeve 88 as well as within the channel or lumen 138. The figure also reveals that the channel 142 is in supporting relationship with the conduit 128.

Figure 11:
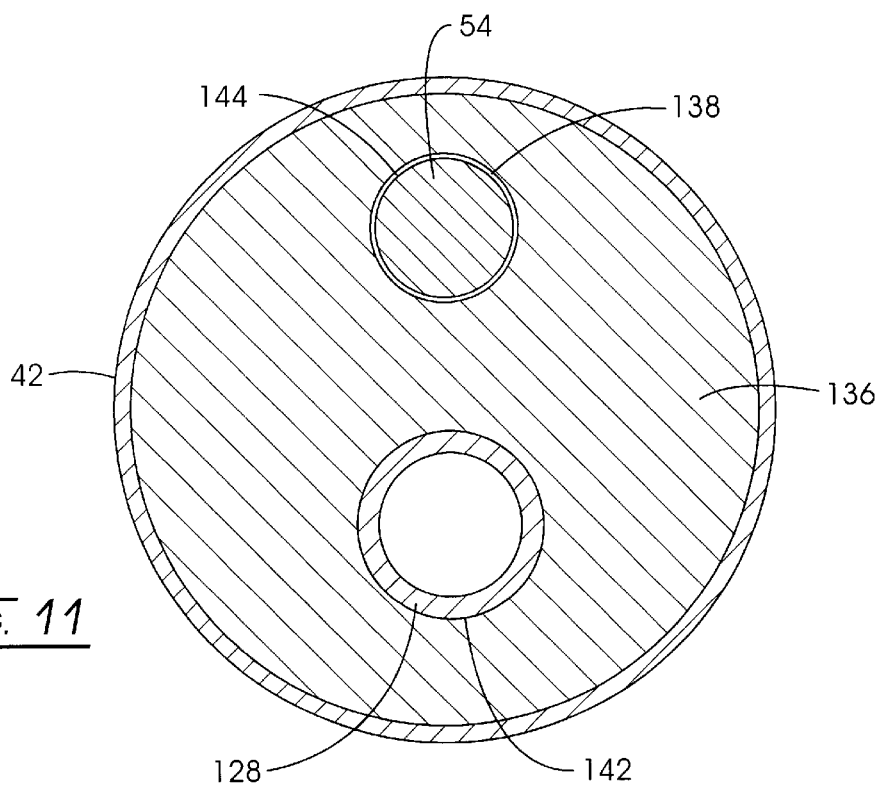
FIG. 11 is a sectional view taken through the plane 11—11 in FIG. 7.

Looking to FIG. 11, a sectional view taken just rearwardly of the section represented at FIG. 10 is portrayed. In this figure, the channel or lumen 138 extending through the electrode guide 136 is revealed. Slidability of electrode 54 through the channel 138 is evidenced by the annular gap 144 extending therebetween. The figure also shows the earlier noted support of the fluid conduit 128 by channel 142.

Looking to FIGS. 7 and 12, the operation of the electrode deployment system is illustrated. In general, the electrode 54 may be constructed of an electrically conductive material such as tungsten, molybdenum, niobium, columbium, tantalum, vanadium, titanium, nickel, cobalt, iron, platinum, zirconium, copper, alloys containing one or more of the above-listed metals, stainless steel, or electrically conductive polymers or plastic. Electrode 52 is deployed by utilizing an actuator assembly to mechanically urge it forwardly in compression against its forward connection as at 128 in block 124. As this compressive movement occurs, electrode 54 is constrained from transverse movement at all locations except at the electrode deployment portion or slot as at 80. Thus, the electrode 54 will tend to distort outwardly to form an arch-like structure, in effect moving outwardly transversely to the longitudinal axis 52. To assure that the transverse movement is outwardly, for the instant embodiment, the deflector guide component 92 provides a preliminary outward deflection or bias upon the electrode 54. Looking to FIG. 12, electrode 54 is shown in phantom at its insertion and removal mode nested orientation, and having been moved to an outward arch defining positioning as represented at 54'. The insulating function of insulative sleeves 86 and 88 becomes apparent from the figure. The extent of outward deployment is dependent upon the corresponding extent of forward movement of the electrode component 54. In this regard, the electrode 54 is actuated to move forwardly an "arch defining distance". For most applications of the instant system, this will be a distance representing a maximum deployment of the apex of the arch, as represented in conjunction with the radius R1 discussed above. It may be observed that an important structural integrity of the deployed electrode 54' is achieved with the present instrument design. A wire arch in compression has been formed between two laterally supportive abutments adjacent the spaced apart forward location 82 and rearward location 84. The side surfaces of slot 80 achieve such lateral support. Thus enhanced lateral pressure on the deployed electrode 54' may be imposed by the practitioner during the rotational or pivotal maneuver described in conjunction with FIGS. 3B, 3D, and 6B without distorting the arch shape. This feature beneficially shortens the length of time required for the cutting procedure and enhances the predictability of the volume circumscribed. FIG. 12 also reveals symbolically, the expression of barrier fluid from the fluid outlet 130 as represented at 146. Such a barrier supplements any barrier effect afforded by the layer of thermal necrosis induced as a result of the electrosurgical cutting process. Thus the rate of neovascularation is further retarded. Barrier fluids may be provided as tissue sealants or glues and/or necrotizing agents. In this regard, fluids such as ethyl alcohol, ferric hyaluronate gel or N, O-carboxymethyl chitosan gel or solution may be utilized.

Figure 13:
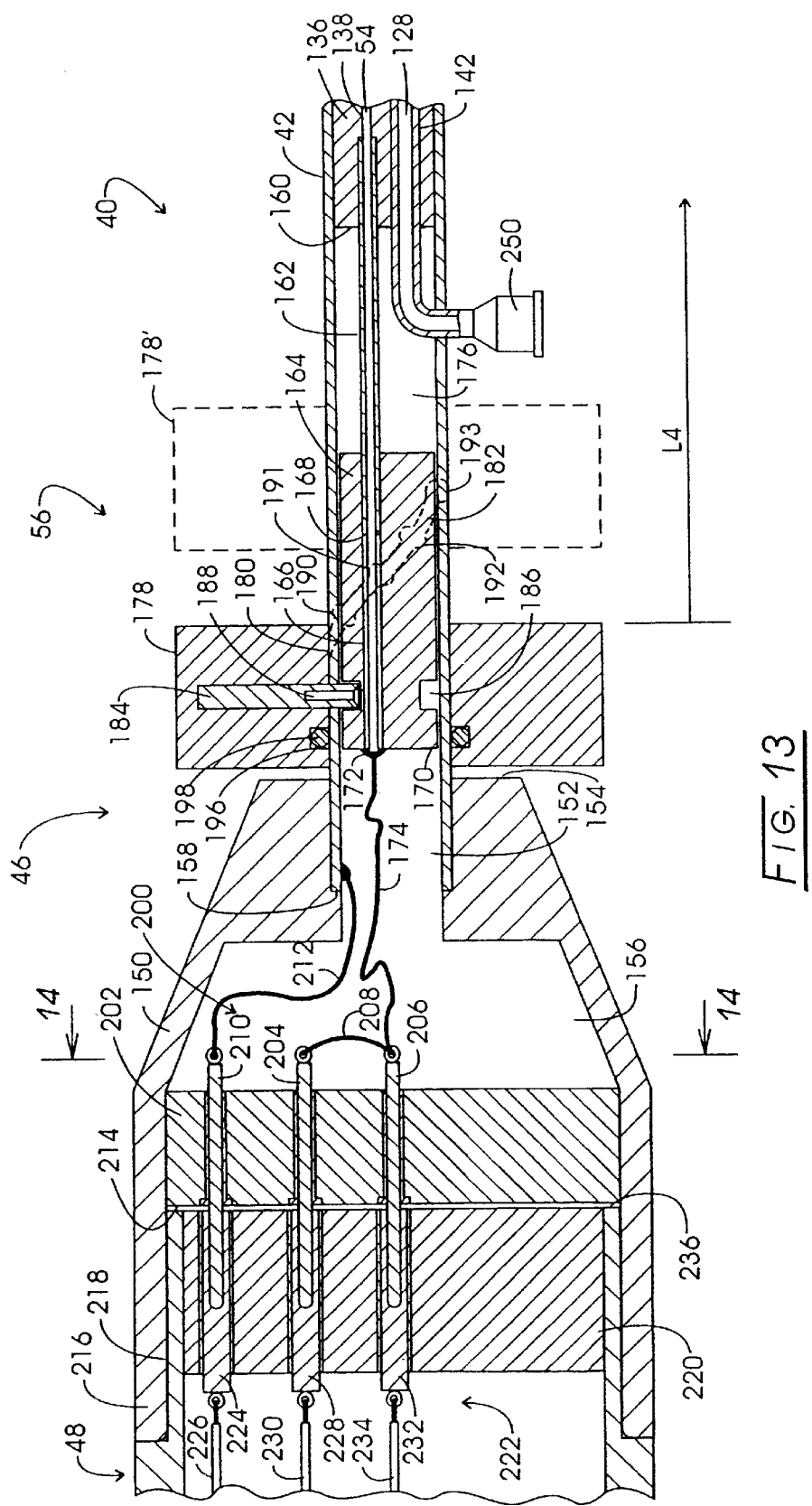
FIG. 13 is a partial sectional view of the base region of the instrument shown in FIG. 1.

Referring to FIG. 13, base or rear region 46 of the instrument 40 is revealed in sectional detail as it is coupled with the support member 42. Looking to the figure, support member 42 is seen to be connected with the cylindrical forward housing 150 at a centrally disposed cylindrical opening 152. Cylindrical opening 152 extends from a circular forward face 154 to an interior cavity 156. The rearward end of support member 42 is seen to abut against a shoulder 158 formed within the opening 152. Stationary electrode guide 136 is seen to extend to the base region 46, having a rearward face 160. Shown extending through the electrode guide 136 is the earlier described channel or lumen 138 within which electrode 54 is slidably disposed. Stationary guide 138 functions to slidably retain electrode 54 and restrain it for longitudinal movement only.

Mounted into the rearward face 160 of electrode guide 136 is a tubular, rigid insulative support sleeve 162. Slidably retaining electrode 54, the sleeve 162 extends in cantilever fashion rearwardly into slidable insertion within an electrode drive block 164. In this regard, a channel or lumen 166 within the block 164 slidably receives sleeve 162. Note that sleeve 162 is seen to end or terminate at 168. However, electrode 54 extends beyond the termination point 168 within channel 166 to the rear face 170 of electrode drive block 164. Block 164 is formed of an insulative material and electrode 54 is seen to be attached to the block at its rear face 170 as seen at union 172. Attachment may be by an electrically conductive adhesive or solder. Also electrically coupled to electrode 54 at the union 172 is a flexible electrical lead 174. Lead 174 is configured in a loosely extended fashion to provide "slack" to permit its forward translation upon the actuation of the electrode system.

Electrode drive block 164 is slidably mounted within the rearward cavity 176 of support member 42 and its position is controlled by the practitioner. In this regard, advancement or retraction of the drive block 164 is carried out by rotating a cylindrical control knob 178 in one direction or another to carry out deployment or retraction of electrode 54. Knob 178 is formed having a cylindrical bearing surface 180 which is slidably positioned over the outer surface of support member 42. At the location of this mounting, a helical slot 182 extends through and winds about support member 42. Extending through this slot 182 is a slot tracking pin 184 which is mounted radially within the knob 178. The inward end of tracking pin 184 slidably engages a rectangular annular groove 186 formed rearwardly within the electrode drive block 164. Spring mounted for outward bias within the slot tracking pin 184 is an expansion or detent member 188. With the arrangement shown, practitioner rotation of knob 178 will cause translational movement to occur with respect to both knob 178 and block 164 either in a forwardly actuating direction or a retraction direction. This occurs as the pin 184 tracks within helical slot 182. The resultant movement of block 164 drives electrode 54 forwardly or rearwardly. A maximum forward movement of knob 178 is represented in phantom at 178'. In effect, this translational movement amounts to the earlier-described "arch defining distance". To facilitate the positioning of knob 178 at intermediate or incremental locations along the track of the helical slot 182, grooves as at 190–193 are formed within the slot 182. These grooves 190–193 are releasably engagable by the detent member 188. Further stability of positioning may be provided by locating an annular slot as at 196 within the knob 178 extending outwardly from the cylindrical bearing surface 180. Within that slot there is positioned an O-ring 198. The frictional engagement of the O-ring 198 with the outer surface of support member 42 will enhance the stability of positioning of knob 178 and, in consequence, the positioning of electrode 54.

As discussed above, during the deployment, physical movement and retraction of electrode 54 an electrosurgical cutting defined current and voltage may be applied to it from lead 174. Additionally, during an iteration of that procedure, a coagulating voltage and current waveform may be applied from that lead. Also, an earlier noted "blend" of these two waveforms may be applied from that lead.

The leads within cavity 156 extend to an array of connector pins 200 which extend from their mounting within a connector mounting block 202. Three of these connector pins of the array 200 are seen in FIG. 13. In this regard, pin 204 supplies electrosurgically cutting defined current and voltage or the noted "blend" output. Correspondingly, pin 206 provides a current and voltage intended for coagulation. Note that connector 204 is electrically coupled with connector 206 by a jumper 208. Pin 206 additionally is coupled via earlier described line 174 to electrode 54. Thus, with appropriate control logic evoked from the control features of the electrosurgical generator assembly 12, connector pin 206 is open circuited during electrosurgical cutting performance with current delivery emanating from connector pin 204. Conversely, connector pin 204 is open circuited during coagulation voltage and current delivery from pin 206. An optional connector pin within the array 200 is shown at 210. As shown by a flexible lead 212 which is electrically connected to the support member 42, this connection may be used to apply electrosurgical return to the support member 42 either at the location shown or more forwardly, for example, at a discrete return or additional electrode adjacent the forward end region 50.

Handle 48 is removably coupled to the assembly including housing 150 and connector pin block 202 and extends rearwardly from the rearward face 214 of block 202. With the opposite sides of the connector pin array 200 extending through face 214 and with housing 160 extending as an open right cylinder at wall portion 216, a male socket arrangement is evoked. Thus, the instrument 40 can be plugged into the mating female socket of handle 48 for connection to the generator and control assembly 12 via cable 32 (FIG. 1). Accordingly, the hand manipulable handle 48 may be provided for use with any of the variety of instruments 40. The handle component 48 is necked down at 218 to be insertable within the cylindrical receptive cavity defined by wall portion 216. Necked down portion 218 is connected with a cylindrical receptacle support block 220 which contains an array of electrical pin receptors shown at 222. These receptors correspond with the connector pins of array 200. Of the pin receptors shown, pin receptor 224 provides connection with pin 210 and functions to couple electrical return from lead 226. Pin receptor 228 functions to provide monopolar electrosurgical cutting current and voltage or a "blend" output and is seen connected with input lead 230. Finally, pin receptor 232 conveys coagulating current and voltage from input lead 234. Pin receptors of the array 222 extend forwardly to the forward face 236 of pin receptacle support block 220 to provide for connection with the corresponding connector pins of array 200.

Figure 14:
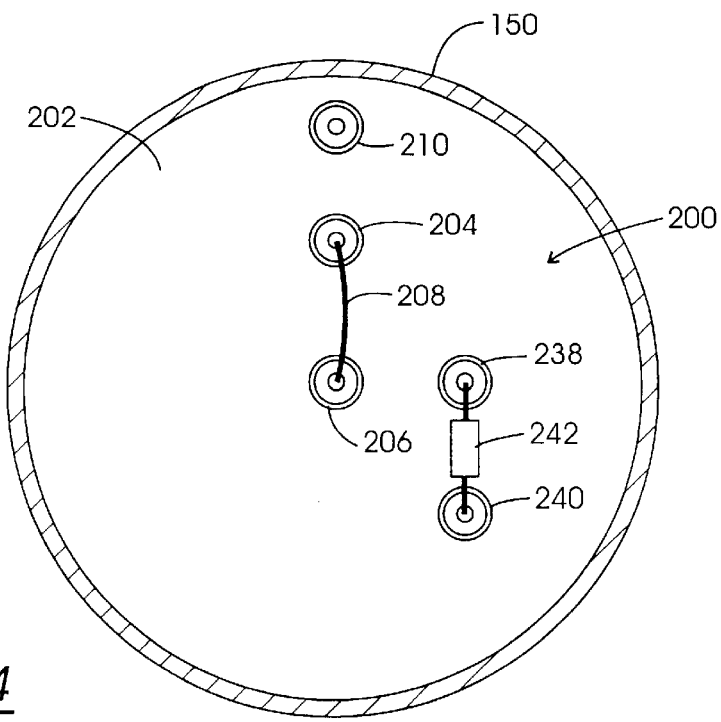
FIG. 14 is a sectional view taken through the plane 14—14 in FIG. 13.

To provide a form of automatic adjustment of the electrosurgical generator control with respect to the type of electrode deployed and electrical parameters desired, the connector pins at array 200 may be employed for coding purposes. Such additional control functions are shown in FIG. 14 in conjunction with the earlier described pin connectors of array 200. In that figure, connector pins 238 and 240 are provided in circuit connection with an electrical coding element 242. Element 242 may be, for example, a resistor, capacitor or inductor which is interrogated from the control system at generator and control arrangement 12 to identify voltage and/or current settings and limits for electrosurgical tissue cutting procedures, particularly corresponding with the functional physical characteristics of the electrode involved as at 54.

Returning momentarily to FIG. 13, barrier fluid conveying conduit 128 is seen to extend into cavity 176 and protrude through the wall of support member 42. As it protrudes therefrom, it is connected to a fitment 250, for example, of a variety suited for connection with a conventional hypodermic syringe which will carry barrier fluid. Thus, the syringe represents a form of fluid reservoir wherein the fluid can be manually pressurized for conveyance along conduit 128 and expression at the fluid outlet 130 (FIG. 12). Fluid delivery conduit 128 may be formed, for example, of stainless steel or silicone. The figure also, in cooperation with FIG. 12 identifies a dimension, $L_4$ representing a length of the entire support portion.

Referring to FIG. 15, a block schematic representation of the surgical generator and associated control assembly of the system 10 is portrayed. In general, this latter feature of the system functions to decode the code carrying electrical parameters within the instrument 40. Then, responding to switch actuation from the practitioner, the generator function supplies a monopolar radiofrequency (RF) electrosurgical cutting current to the electrode 54 of instrument 40. As is discussed in connection with FIGS. 3A–3E and 6A–6C, this cutting activity ensues both during deployment of electrode 54, manipulation thereof, for example, by pivoting and during a retraction of it in order to vascularly isolate the targeted tissue. The cutting manipulative procedure with electrode 54 may be reiterated in conjunction with the application of a coagulative current and voltage and, optionally, the cutting current and coagulating current may be combined.

Looking to the figure, a radiofrequency (RF) cutting current and "blend" output electrosurgical generator function is represented at block 252, while a radiofrequency (RF) coagulation current electrosurgical generator is represented at block 254. Earlier described connector receiving receptacle 16 reappears schematically in conjunction with cable 62 and connector 64 extending from the foot pedal switch 66. Similarly, connector receiving receptacle 17 reappears in connection with connector 78 and cable 76 which extends to the remote patient return 74 (FIG. 1). Cable 32 extending from the handle portion 48, as coupled with the instrument 40, reappears in connection with the multi-pin connector 34 and multi-pin connector receiving receptacle represented generally at 18.

Inputs and outputs associated with the connector 34 are shown in connection with a terminal block 256. The inputs and outputs at terminal block 256 are those associated with the connector pins described in connection with FIG. 14. Accordingly, each of the connector locations at terminal block 256 is identified by the numerical identification of the connector pins set forth in FIG. 14 but in primed fashion. Additionally, the connector block 256 includes generalized representations for interface functions contained on the handle component 48 itself. In this regard, terminal 258 is electrically associated with switch 58 shown in FIG. 1, which signals the control system to commence electrosurgical cutting operation or "blend" performance in similar fashion as switch 68 of foot pedal switch 66. Terminal 259 is operationally designated with respect to switch 60 at handle 48 and provides for the generation of a coagulation current defined output. Terminal 260 is designated for the purpose of energizing one LED at array 72 upon handle 48 which corresponds with the "energized" output at LED 23 of generator assembly 12. The terminals 258–260 are associated with a control logic circuit 262 via respective arrows 264–266. In similar fashion, the outputs of switches 68 and 70 of the foot pedal switch assembly 66 are introduced to the control logic circuit 262 via arrow 268.

Upon being powered-up via a power-on switch (not shown), control logic circuit 262 carries out a sequence of procedures in anticipation of the switch actuations to be performed by the practitioner. As represented by respective arrows 270 and 272, the control logic circuit, inter alia, carries out control over the activation of the RF electrosurgical cutting/blend generator 252 and the RF electrosurgical coagulation generator 254. However, as a condition precedent to the outputting of the initially utilized electrosurgical cutting current from generator 252, the control logic circuit 262 responds to the selection signal input of a decoding circuit as represented at arrow 274 and block 276. Decoding circuit 276, in turn, is seen responding via leads 278 and 280 to the decoding electrical parameter condition developed via terminals 238' and 240'. This represents an interrogation of coding element 242 as described in connection with FIG. 14. Following carrying out of a performance configuration of the cutting electrosurgical generator 252 with respect to the input from decoding circuit 276, control circuit 262 activates the display function represented at block 282 as represented by arrow 284. Display 282 provides an aural cueing as described earlier as well as an activation of the LED at 22 representing a "system ready" condition. LED 25 is illuminated during the above-noted decoding procedure. Logic circuit 262 then, as represented at arrow 286, applies a control signal to a solid state switching network represented at block 288. This provides for the closure of switch functions symbolically represented at SI and S2 which couple respective output and return lines 290 and 292 with respective lines 294 and 296 extending to the primary input of an isolation transformer 298. Transformer 298 is employed to isolate the patient from the radiofrequency generator and control system 12, as well as to isolate the RF cutting source 252 from the coagulation source 254. The output from the secondary winding of transformer 298 is provided at lines 300 and 302 25 and is directed to the input of a high pass filter represented at block 304. Filter 304 further reduces the amplitude of lower frequency signals, for example, frequencies below about 20 kHz which can otherwise lead to unwanted stimulation of nerves and/or muscle tissues within the patients' body. For example, interference is possible with natural or imposed pacing signals within the heart. The return component of the circuit, upon exiting high pass filter 304, is coupled, as represented at line 306 with the remote patient return as at 74 (FIG. 1) via receptacle 17. Correspondingly, the output from high pass filter 304 is directed, as represented at line 308 to terminal 204' and thence via cable 32 to connector pin 204 for conduction via jumper 208 and lead 174 to electrode 54 (FIG. 13). As this current and voltage waveform is applied, the practitioner will turn the control knob 178 and provide for the deployment of electrode 54 as described in connection with FIGS. 3A–3E and 6A–6C. As discussed in conjunction with FIG. 13, in connection with connector pin 210, as an alternative, the return may be developed from a return electrode supported at support member 42. This electrical association is represented at dashed line 310.

Upon completing a circumscriptive cutting procedure as discussed in conjunction with FIGS. 3A–3E and 6A–6C, the practitioner then releases the switch 58 or 68 which had been depressed to carry out that function. Then, for the reiterative coagulation procedure, either of switches 60 or 70 are closed to cause the coagulation mode of operation. With such closure, control logic circuit 262 responds by activating the display function 282 to provide an aural clue as earlier described, as well as to illuminate the LED 24 as seen in FIG. 1 and an appropriate LED at the handle 48. RF coagulation electrosurgical generator 254 then is activated with the generation of a signal, as represented at arrow 286 and block 288, closing switches symbolically represented as S3 and S4. Such closure couples lines 312 and 314 with corresponding lines 316 and 318 which are directed to the primary winding of an isolation transformer 320. Transformer 320 provides the isolation features earlier described in connection with transformer 298. The return component of the secondary output of isolation transformer 320 is coupled via line 322 to the electrosurgical return function at line 306 extending, in turn, to connector 17. As before, as an alternative, an on instrument return can be utilized as represented at dashed line 310. The second output from the secondary of isolation transformer 320 is provided at line 324 which extends to the input of a high pass filter 326 which serves the same function as filter 304. From the filtering function 326, voltage and current are provided at line 328 which, in turn, extends to terminal 206'. As illustrated in connection with FIG. 13, terminal 206' is electrically associated via cable 32 and associated lead 234, receptor pin 232, pin 206 and lead 174 extending to electrode 54.

Support member 42 may be formed from a variety of materials, particularly depending upon its implementation. In this regard, it may be rigid as shown in the embodiments thus far described. Additionally, the electrosurgical cutting approach may be employed with a flexible support such as a catheter. Such flexible components may be delivered through a guide tube or may be steerable and employed with devices similar to flexible intravascular and endoscopic systems. Materials which may employed in forming in the support member may be, for example, metals such as stainless steel, elastomeric materials or inorganic materials such as ceramic, glass/ceramic or glass, unfilled plastic or filled plastic or fiber-reinforced composites such as a pultrusion, marketed by Polygon Company of Walkerton, Ind. For purposes of accurately positioning it with respect to targeted tissue volume, the forward end region or working end 50 may incorporate a coating, covering or component which enhances its image contrast. For example, coverings or components may be used as radiography markers, in which case, a platinum band may be positioned about the surface of the component. Additionally, an ultrasound contrast agent such as a coating of hollow microspheres may be positioned at that region. While the most prevalent use of the instrument 40 will be in conjunction with substantially small targeted tissue volumes, the size of targeted tissue may vary substantially and the dimension of certain components of instrument 40 may fall with a range of values. In the foregoing figures, these variable dimensions have been graphically identified as $L_1$–$L_5$, $D_1$ and $D_2$. The dimensions $L_x$ are described in connection 10 with FIG. 12 and, more particularly, with respect to $L_4$ in conjunction with FIGS. 12 and 13, the latter figure showing the terminus of that dimension at the retracted orientation of the actuator assembly 56. The ranges for the above geometric parameters are set forth in the following tabulation (all dimensions being in inches):

|  | Size Range | Preferred | Most Preferred |
|---|---|---|---|
| $D_1$ | 0.020–0.50 | 0.030–0.25 | 0.040–0.20 |
| $D_2$ (cutting electrode) | 0.005–0.050 | 0.008–0.040 | 0.010–0.02 |
| $L_1$ | 0.15 to 5.5 | 0.30 to 4.5 | 0.40 to 3.5 |
| $L_2$ | 0.05 to 1.50 | 0.080–0.75 | 0.10–0.6 |
| $L_3$ | 0.10 to 4.0 | 0.20 to 3.2 | 0.30 to 2.5 |
| $L_4$ | 1.2 to 12.0 |  |  |
| $L_5$ | 0.10 to 5.0 | 0.20 to 4.0 | 0.30 to 3.0 |

In the course of carrying out the procedure represented in FIGS. 3A–3E and 6A–6C, during electrosurgical cutting, the temperature imposed at the tissue confronting the electrode 54 will be well above 100° C. and the cutting effect, as noted above, causes a destruction of cells, inasmuch as water molecules contained within most tissues commence to vaporize at that temperature. Due to the large increase in volume during this phase transition, gas bubbles are formed inducing mechanical ruptures and thermal decomposition of tissue fragments. Gratuitously, this cutting action is quite local, thus, the term "cutting" is appropriate to describe it. The large vaporization heat of water (2253 kJ/kg) is advantageous, since the vapor generated carries away excess heat and helps prevent any further increase in the temperature of the adjacent tissue. Fluids in the thus formed "cuts" generated by the electrode 54 will enhance the electrical connection carried subsequently for purposes of surface coagulation.

As discussed above in connection with FIGS. 13 and 15, remote returns as described at 74 in FIG. 1 can be replaced with a surface electrode generally located at the forward end region of the instrument and, more particularly, where it can provide a return contact with the tissue of the patient. Looking to FIG. 16, such an instrument adaptation is represented generally at 340. As before, the instrument 340 includes a support member forward end region 342 which extends to a trocar shaped tip 344. A slot-shaped deployment portion 346 is seen to extend between a forward location 348 and a rearward location 350. Shown deployed between the abutment defining locations is a thin resilient electrode 352 which is supported by the slot-shaped deployment portion 346 in conjunction with electrically insulative sleeves 354 and 356. Insulatively mounted upon the surface of the forward end region 342 of the support member is a surface electrode 358. Electrode 358, as noted, functions in replacement of the remote electrode 74 (FIG. 1).

Referring to FIG. 17, an embodiment of the instrument of the invention employing two electrodes is represented in general at 360. The forward end region 362 of the support member 364 of instrument 360 is revealed in the figure. Region 362 extends to a tip 366 which is configured having an annular shoulder 368 which is inserted within the forward end of the tubular support member or cannula 364. Tip 366 is seen to be configured as a trocar for purposes of penetration (percutaneous) through the patients' tissue. Positioned immediately rearwardly of the tip 366 is a cylindrical, electrically insulative electrode engagement block 370 having two rearwardly facing cylindrical openings therein, 372 and 374. Opening 374 receives and adhesively secures the distal end of an inner electrode 376, as well as a forwardly disposed inner electrode sleeve 378. Electrode 376 is seen to extend through and is abutably supported from an elongate deployment slot 380. Slot 380 as before, extends parallel to the longitudinal axis 382 of the forward end region 362 from a forward location 384 to a rearward location 386. Inner electrode 376 is shown in its outwardly deployed, arch forming orientation extending into slidable engagement with an electrically insulative sleeve 388 which, in turn, is fixed within a cylindrical cavity 390. Cavity 390 extends rearwardly within a cylindrical, electrically insulative electrode guide and conduit support 392. In particular, the electrode 376 slidably extends within an elongate cylindrical cavity 394 which, in turn, extends to the base region of the instrument in the manner described in connection with FIG. 13. An upper electrode 396 is positioned within the deployment slot 380 radially above inner electrode 376. In this regard, electrode 396 is adhesively engaged within cylindrical cavity 372 in conjunction with insulative sleeve 398. Electrode 396 is shown in its deployed arch forming profile as extending in slidable relationship through flexible electrically insulative sleeve 400. Sleeve 400 is supported by the sides of a cavity 402 formed in the electrode guide and conduit support 392. Cavity 402 extends as a cylindrical cavity 404 to the base region of instrument 360.

Located within the deployment portion 380 and forming a component of the slot is a deflector guide component 406 which, as before, functions to support the electrodes 376 and 396 intermediate the forward location 384 and rearward location 386. The guide 406 slightly outwardly biases the electrodes 376 and 396 to facilitate their outward deployment as they are compressibly urged forwardly to create the arch profile. Electrodes 376 and 396 are illustrated in phantom in their retracted, nested orientation at 376' and 396'. As before, barrier fluid may be expressed from the deployment slot 380 by virtue of a barrier fluid conduit 408 extending through the guide 406 to an outlet port 410. The channel 408 is configured in the manner of channel 128 as described in FIG. 13 as it extends to the base region of instrument 360.

Figure 18:
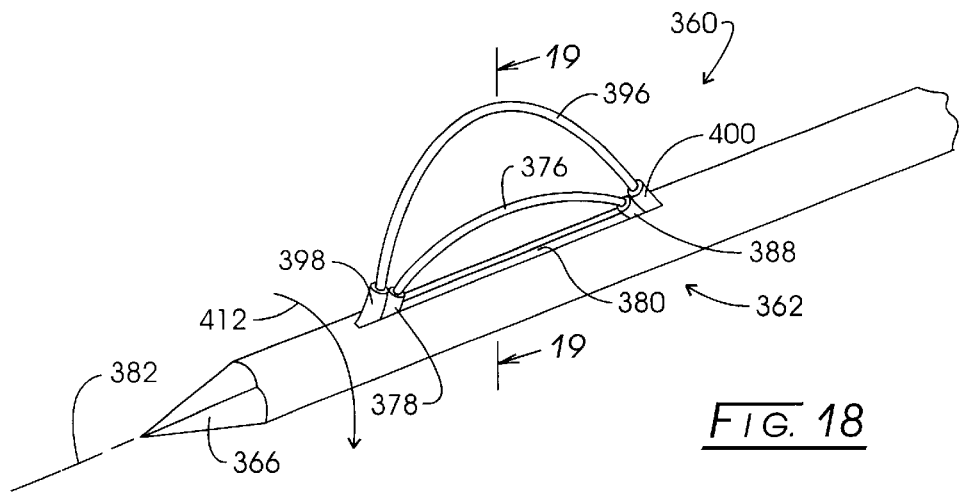
FIG. 18 is a pictorial representation of the forward end region of the instrument of FIG. 17.

As is apparent from FIG. 17, the apex dimension or height of the arch defined by electrode 376 is smaller than the corresponding apex height of the arch profile of electrode 396. Looking to FIG. 18, forward the instrument 360 at its forward end region 362 again is depicted pictorially in conjunction with longitudinal axis 382 and an arrow 412 representing a pivoting or rotation of the forward end region 362 about axis 382. With the dual electrode arrangement shown, the procedure for carrying out vascular isolation of a targeted tissue volume can be improved in terms of the time required for requisite maneuvers. Each of the electrodes 376 and 396 retain the inherent structural integrity of the arch formation of the invention to additionally improve upon this time element for the procedure involved. As in the previous embodiments, during this procedure, electrosurgical cutting current is applied to the outer electrode 396 and for at least one cut to the inner electrode 376 so that a full circumscription of the targeted tissue volume is achieved. The procedure is represented in the maneuvering diagram set forth in FIGS. 19A–19C.

Figure 19A:
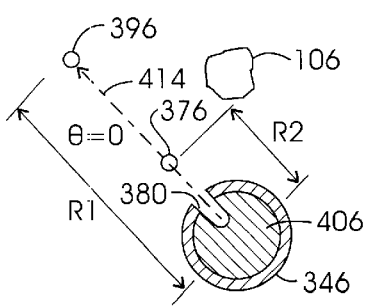
FIGS. 19A–19C are schematic sectional views taken through the plane 19—19 in FIG. 18, showing maneuvering procedures carried out with the instrument of FIG. 18.
Figure 19B:
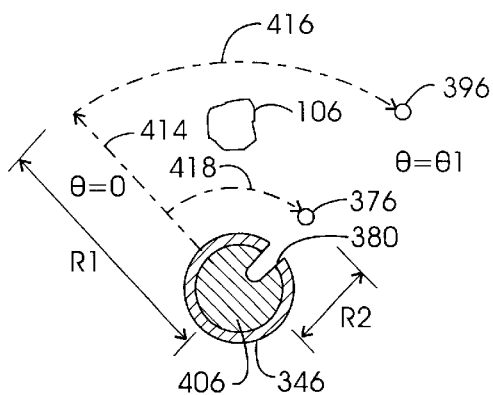
Figure 19C:
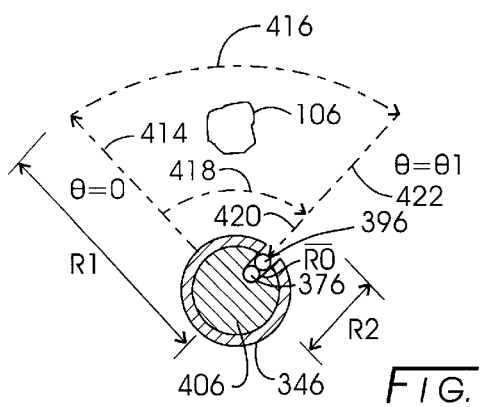

Looking to FIGS. 19A–19C, a section through forward end region 362 is shown as it intersects the electrodes 376 and 396 at the apexes of the arches defined by them when fully deployed. In the figures, the electrode 376 and electrode 396 apex locations are shown with that same numeration. The figures further reveal the deployment slot 380, as well as a section of the deflector guide component 406 and support member 362. In FIG. 19A, electrode 396 is shown having been deployed to an apex radius R1 and having completed an electrosurgical cut to that radial extent as represented by the cut indicator line 414. This cut indicator line 414 will reside in healthy tissue but in adjacency with the targeted tissue volume 106 peripheral extent. To carry out a circumscription of such tissue, instrument forward end region 362 will have been oriented angularly as shown and indicated by the angular designation θ=0. The deployment of electrode 396 is such that it will pass over the "top" of the targeted tissue 106 peripheral extent. Additionally, electrode 376 will have deployed within the cut tissue interface represented by the cut indicator line 414 to a radial position represented at R2. This position is located such that, upon pivoting of the electrode 376, it will pass "under" the peripheral extent of targeted tissue 106. Looking to FIG. 19B, the fully deployed electrodes 376 and 396 continue to be energized and the forward end region 362 is pivoted as represented by arrow 412 (FIG. 18) to the angular position θ=θ1. Electrode 396 will remain at the radial distance R1 and electrode 376 will remain at the radial distance or deployment $R_2$. However, electrode 396 will have developed an arc shaped cut across the "top" of targeted tissue volume 106 as represented by cut indicator line 416. Simultaneously, electrode 376 will have carried out an electrosurgical cut represented by arc shaped cut indicator line 418. Referring to FIG. 19C, the final maneuver is carried out by energizing both electrodes 396 and 376 while at the radial angular orientation θ=θ1 and retracting them into the nested orientation shown. This will generate the cut indicator lines 420 and 422.

Referring to FIG. 20, an embodiment of the invention establishing a minimally invasive instrument having a relatively small outer diameter, for example, about 0.125 inch is revealed. The forward end region of the instrument is shown at 430 forming part of a solid, as opposed to cannular support member 432. The material forming support member 432 will be selected in accordance with its intended utilization and may be either flexible or rigid. A rigid arrangement is shown in the instant figure. The forward end region 430 extends to a trocar-shaped tip 434. As represented additionally in FIGS. 21–23, the support member 432 and its forward end region 430 are unitary or integrally formed and have a cylindrical outer periphery disposed about a longitudinal axis 438. Extending in parallel with that axis 438 from a securement region 440 adjacent tip 434 toward the base of the instrument is an elongate outwardly open slot 442. As seen in FIGS. 21–23, the slot 442 has oppositely disposed sides 444 and 446 which extend a slot depth to a slot bottom 448. The outer periphery of the entire structure, with the exception of tip 434, thus far described is covered with an electrically insulative coating 450. Located adjacent bottom surface 448 of the slot 442 is a thin, resilient elongate electrode 452 having a distal end 454 which extends within the securement region 440. Looking to FIGS. 20 and 21, distal end 454 is seen to be positioned within a rigid stainless steel tube 456, the outer periphery of which is electrically insulated, for example, with two layers of a shrink wrap which covers the forward end of the tube adjacent the tip 434. That covering is shown at 458 in FIG. 21. Covering 458 may be dispensed with where, as represented in FIG. 21, the slot 442 is fully electrically insulated at its surface. Electrode 452 is bonded adhesively within the tube 456 and the tube 456, in turn, is retained in position adhesively with a forward retainer component 460 positioned within slot 442 above the tube 456 within the securement region 440. Tube 456, as well as the securement region 440, extend to a forward location seen in FIG. 20 at 462. As seen additionally in FIG. 22, electrode 452 continues from forward location 462 to extend through a deployment slot region shown generally at 464 to a rearward location 466 terminating region 464. From rearward location 466 to the base of the instrument, as in the above-described embodiments, the electrode 452 slidably extends through a rigid supporting channel herein implemented as a stainless steel tube or channel tube 468. As seen in FIG. 23, an annular gap is present between the outer surface of electrode 452 and the channel tube 468. Additionally, the channel tube 468 is seen to be enclosed within an electrically insulative shrink wrap 472 (FIG. 23). Where a unitary coating as illustrated at 450 is provided for the instrument, then the shrink wraps as at 472 in FIG. 23 and 458 in FIG. 21 may be dispensed with. However, in securement region 440, the outer distal tip of the electrode 452 must be insulated from tip 434. However, where such shrink wrap arrangements are provided, insulation within the deployment slot region 464 preferably will be provided by a thin membranous sheet formed, for example, of an aromatic polyimide marketed under the trademark "Kapton". The channel tube 468 is retained within the slot 442 by a rearward retainer component 474. This rearward retainer component 474, as well as forward retainer component 460 additionally may be retained within the slot 442 by a shrink wrap covering positioned about the periphery 436. Retention of the components 460 and 474 may be with such a shrink wrap approach (not shown) or by an application of a medical grade adhesive. As before, the electrode 452 is deployed by urging it forwardly in compression to effect outward movement generally transversely to the longitudinal axis 438 into an outwardly depending arch formation represented in phantom at 452' in FIG. 20. As before, the arch formation 452' extends from supporting abutments generated by the sides of the slot 442 adjacent forward location 462 and rearward location 466. The electrode 452 is retracted into its nested or insertion and removal mode orientation by urging it rearwardly for movement toward the slot 442.

FIGS. 24–27 reveal an embodiment corresponding with FIGS. 20–23 but incorporating a barrier fluid delivery channel in conjunction with slot 442. Accordingly, where the components of this next embodiment reappear they are identified by the same numeration but in primed fashion. In FIG. 24, the forward end region of 430' is shown as a component of support member 432' and extends to a tip 434'. Support member 432' is cylindrical and disposed about a longitudinal axis 438'. The cylindrical outer periphery of the instrument is shown in FIGS. 25–27 at 436'. Extending within the solid cylindrical support member 432' is an elongate slot represented generally at 480. As before, slot 480 extends along the longitudinal axis 438' from a position in adjacency with tip 434' toward the base region. The slot is configured having oppositely disposed slot sides 482 and 484 (FIGS. 25–27). As shown in FIGS. 24 and 25, within the securement region 440 and extending to about the midpoint of the deployment slot region 464', the slot bottom 486 is configured having a depth corresponding with that shown in FIGS. 21–23. However, as represented in FIGS. 24 and 26, that depth extends within the deployment slot region 464' only to an output location seen in FIG. 24 at 488. Rearwardly of the location 488, the slot depth has a greater dimensional extent as represented by the slot bottom 490 seen in FIGS. 24, 26 and 27. In the present embodiment, adjacent the slot bottom 490 is a barrier fluid delivery channel implemented as a stainless steel tube 492. As before, the slot 480 and support member outer cylindrical periphery 436' is provided with an electrically insulative surface or coating 450'. However, this coating may be implemented by thin membranes or shrink wrap as discussed in connection with FIGS. 20–23. The conduit 492 extends from a remote fluid input at the base region as described in conjunction with FIG. 13 and terminating at the output location 488. Note at FIG. 24 that that output is curved outwardly to promote fluid expression from the deployment slot region 464'.

The electrode 452' distal end 454', as before, is seen to extend within a rigid tube 456' which may be covered with an electrically insulative shrink wrap 458' as seen in FIG. 25. The electrode distal end 454' is adhesively retained within the tube 456' within securement region 440'. Tube 456', in turn, may be adhesively retained within region 440' and further retained by a forward retainer component 460' positioned within the slot 480 and extending, with tube 456' to the forward location 462' (FIG. 24). In similar fashion electrode 452' is slidably retained within a channel 468' herein implemented as a stainless steel tube. This slidability is evidenced in FIG. 27 by a gap 470'. As before, tube 468' may be covered with an electrically insulative shrink wrap as at 472', particularly when the exterior electrically insulative coating 450' is not provided along the sides and bottom of slot 480. As before, the assemblage of tubes 492 and 468' may be retained within the slot 480 by a rearward retainer component 474'.

Electrode 452' is deployed by urging it forwardly in compression to form the buttressed arch formation extending between forward location 462' and rearward location 466' as shown in phantom at 452" in FIG. 24. Retraction is carried out by urging the electrode 452' rearwardly to convert the arch formation at 452" into a nesting orientation as shown at 452'.

Referring to FIGS. 28–32, one preferred arrangement for the instrument embodiment of FIGS. 20–27 is revealed. In the figure, the forward end region 500 of the cylindrical support member 502 is revealed to again have a solid structuring, the generally cylindrical shape of the region 500 being disposed about a longitudinal axis 504. Forward end region 500 extends to a pointed tip 506. Extending from an end surface 508 in parallel with the longitudinal axis 504 rearwardly toward the base region is an elongate slot represented generally at 510 of a rectangular cross section. Looking in particular to FIGS. 29–32, slot 510 is seen to be configured having a slot width defined between oppositely disposed slot sides 512 and 514. Sides 512 and 514 extend to a slot bottom 516 of uniform depth which may extend, in turn, to the base region of the instrument. Fixed within the slot 510 is a retention insert represented generally at 518 (FIGS. 28–31) which may be provided as a unitary injection molded, electrically insulative polymeric component. The forward portion of the retention insert 518 establishes a securement region represented in FIG. 28 at 520. Looking additionally to FIG. 29, the retention insert 518 is seen to be formed having an outwardly opening electrode receiving channel with oppositely disposed internal side surfaces 522 and 524 which extend an initial channel depth to an arcuate channel bottom 526. Adhesively secured at this bottom surface 526 is an elongate, thin, resilient electrically conductive electrode 528 which is so retained at region 520 as not to have an electrical association with the material of the forward region 500 of support member 502. Positioning at the bottom surface 526 further is assured by an adhesively retained forward retainer component 530 of rectangular cross-section which extends from the end surface 508 to a forward location 532 (FIG. 28). Retention insert 518 extends rearwardly from forward location 532 within a channel deployment region 534. Here the channel depth extending to the channel bottom surface 526 diminishes to form a double taper profile seen at 528 exhibiting a depth of least dimension at the center region 534 at 536. From position 536, the tapering profile returns to the initial depth represented at 526 in FIG. 29 at rearward location 538. Location 538 represents the rearward terminus of channel deployment region 534. The channel depth at this location corresponds with the channel depth 526 and the corresponding bottom surface at that location is seen in FIGS. 28 and 31 at 540.

FIGS. 28 and 32 reveal that the electrode 528 is slidably mounted within a rigid, tubular metallic channel 542 having a peripherally disposed electrically insulative coating or layer which may be implemented as a polymeric shrink wrap and is shown in FIG. 32 at 544. Electrode 528 is slidable within the channel 542 as is represented by the annular gap 546 additionally seen in FIG. 32. FIGS. 28 and 32 further reveal that the slot 510 supports a rigid tubular barrier fluid duct or delivery channel 548 which additionally is adhesively fixed to channel 542. Fluid delivery channel 548 extends from a fluid input at the base region, as described in connection with FIG. 13, to a fluid output seen in FIGS. 28 at 550. Note that the forward edge of fluid output 550 extends beyond the rearward location 538. FIG. 31 reveals that the sidewalls of the channel-shaped retention insert 518 additionally have been tapered inwardly such that the cylindrical wall of annular cross section 512 of the channel 548 extends over the outward surfaces of the channel sides. This extension is of relatively short distance and is for the purpose of assuring that barrier fluid enters the channel deployment region 534 and is not blocked by electrode 528 when it is deployed into an arch formation represented in phantom at 528' in both FIGS. 28 and 31. To permit this deployment while assuring the expression of barrier fluid into the deployment region 534, the tubular fluid delivery channel 512 is slotted to both receive and support electrode 528 as it deploys from rearward location 538. FIG. 31 reveals that the outward opening slot 552 has a width corresponding with the outer diameter of electrode 528 so as to provide structural support to it and further provide oppositely disposed chord-shaped channel outlet regions 554 and 556 as seen in FIG. 31.

As in the earlier embodiments, electrode 528 is deployed by urging it forwardly in compression to effect its outward movement transversely to longitudinal axis 504 to an extent curving it into an outwardly depending arch formation as shown in phantom at 528' in FIGS. 28 and 31.

As noted above, by virtue of a somewhat nercrotized surface of the tissue at the interface of an electrosurgical cut carried out with the instrument of the invention, a discrete and defined corridor for reception of barrier or necrotizing fluid is evoked. Thus, the positioning of the barrier or necrotizing fluid within this interface is of substantial accuracy to provide more assurance of a complete but restricted coverage of the tissue interface to beneficially retard any rate of neovascularization across the interface. Accuracy of locating this barrier or necrotizing fluid at the cut interface can be enhanced by associating the expression of barrier or necrotizing fluid with the location of the cutting electrode. In one embodiment of the invention, the electrode is formed having an interior fluid transfer cavity and one or a plurality of fluid outlets which are formed within the electrode at the deployment region.

Figure 33:
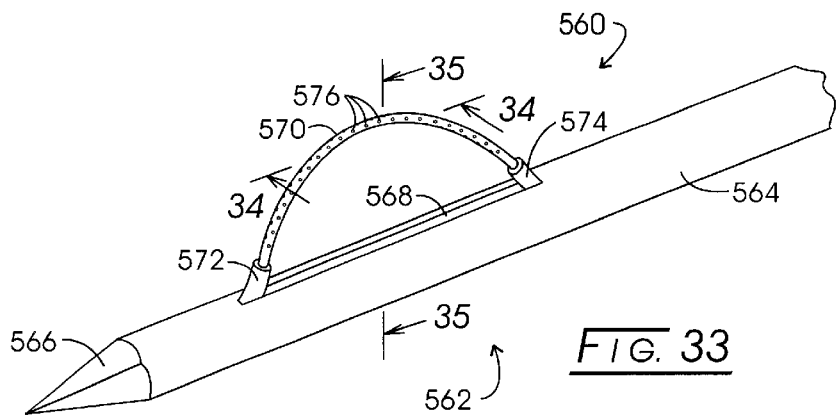
FIG. 33 is a perspective view of the forward end region of another embodiment of the instrument according to the invention.
Figure 34:
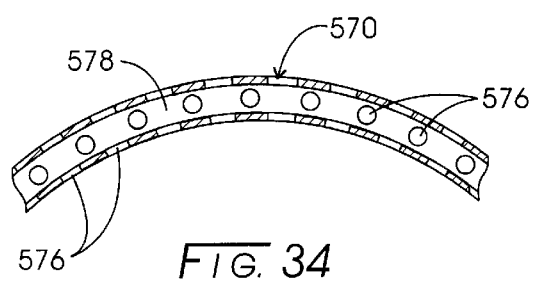
FIG. 34 is a partial sectional view taken through the plane 34—34 in FIG. 33.

Referring to FIG. 33, an embodiment of the instrument of the invention employing an electrode having an internal fluid transfer cavity is represented in general at 560. The forward end region 562 of a support member 564 of instrument 560 is shown in the figure. Region 564 extends to a trocar-shaped tip 566, rearwardly from which is located a slot-shaped deployment portion 568. A thin, resilient electrode 570 is shown deployed into an arch formation from the slot-shaped deployment portion 568. To buttress and electrically isolate the electrode 570 from the support member 564, electrode 570 is covered with a flexible electrically insulative sheath 572 at a forward end region and is slidably inserted within a corresponding sheath 574 at a rearward location. Seen disposed in radial quadrature about the electrode 570 is an array of fluid outlets, certain of which are revealed at 576. Looking to FIG. 34, the electrode 570 is seen to be formed having an interior fluid transfer cavity 578 and the array of fluid outlets or apertures are again represented at 576. In the arrangement shown, the array is represented as four linear arrays at the top, bottom and two sides of the electrode, the side array outlets being displaced from the vertically disposed arrays as shown in the figure. Fluid transfer cavity 578 is in fluid transfer communication with a barrier fluid delivery conduit as described, for example, in connection with FIGS. 7, 12 and 13. The number of outlets 576 employed will depend upon a number of hydraulic related factors and may be varied. Of interest, when employed as an array, the compressive force required to deploy electrodes as at 570 diminishes.

Figure 35A:
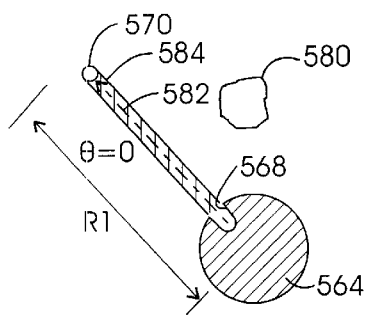
FIGS. 35A–35E are partial and schematic sectional views taken through the plane 35—35 in FIG. 33 and showing a sequence of operational maneuvers which may be carried out with the instrument of FIG. 33.

FIGS. 35A–35E illustrate procedures for maneuvering the instrument 560 to carry out a vascular isolation of a targeted tissue volume of given peripheral extent. As before, these figures are representative of a section taken through the apex of the arch formation of electrode 570 as revealed in connection with FIGS. 33 at section 35—35. The sectional maneuvering diagrams are illustrated in connection with a symbolic tissue volume 580. In each of the figures, the appropriate section of electrode 570 is represented in conjunction with deployment portion slot 568 and the forward end region 562 of support member 564. In FIG. 35A, the forward end region 562 of instrument 560 has been positioned within healthy, viable tissue in adjacency with the peripheral extent of the targeted tissue volume 580. The deployment slot 568 has been angularly oriented at a position designated $\theta=0$ wherein a portion of the surface of the forward end region 562 is in adjacency with what may be termed the "bottom" of the tissue volume 580. Slot 568 is angularly oriented to deploy electrode 570 into an adjacency with what may be termed one side of tissue volume 580. Accordingly, the electrode 570 is electrosurgically activated into a cutting mode and is deployed to the orientation represented by radius R1. An electrosurgical cut is shown having been made as represented by the dashed cut indicator line 582. At this electrode position, electrosurgical excitation of the electrode 570 is interrupted and barrier or necrotizing fluid is expressed from the fluid outlet 576 to, in effect, fill the tissue interface developed by the cut represented at 582. This filling is represented by the filled interface outline 584.

Figure 35B:
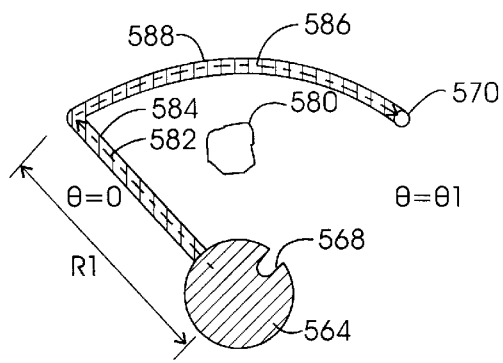

Electrode 570 then is excited again and the forward end region 562 of the instrument 560 is pivoted to the angular orientation $\theta=\theta 1$ as represented at FIG. 35B. Electrode 570 remains at the radial distance R1 and will have created an arcuate cut represented by cut indicator line 586. At the position shown in the figure, electrosurgical excitation of the electrode 570 is interrupted and barrier or necrotizing fluid is caused to flow from the outlets 576 to fill the interface represented by joining tissue at the cut 586. This filling is represented by the filled interface outline 588.

Figure 35C:
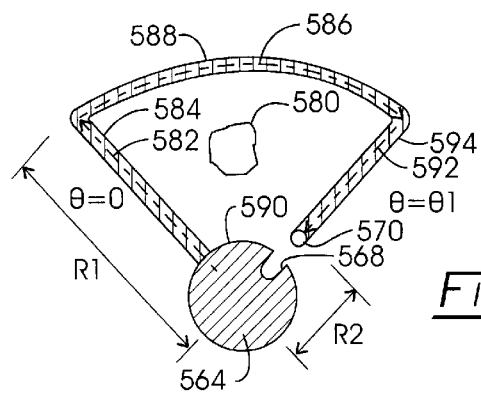

Referring to FIG. 35C, a next maneuver may be to electrosurgically excite electrode 570 while the forward end region 562 is at the angular orientation $\theta=\theta 1$ and simultaneously retract it toward deployment slot 568 as represented by the cut indicator line 592. Such retraction may be terminated at a position above slot 588. At this location, now designated radial distance R2, electrosurgical excitation of the electrode 570 may be interrupted and the interface developed by the cut 592 may be filled with barrier or necrotizing fluid as represented by the filled interface outline 594. Either of two optional maneuvers may be carried out at this position in the procedure.

Figure 35D:
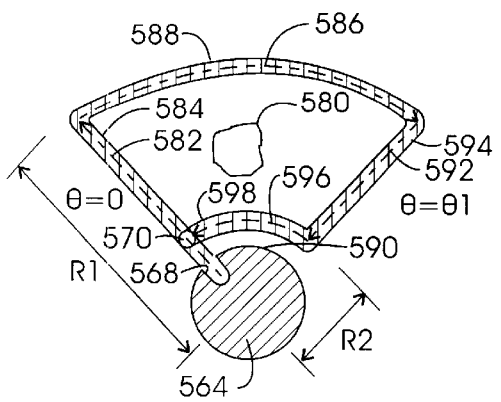

One such optional maneuver, as represented in FIG. 35D, may be elected for relatively larger volumes of targeted tissue. In that figure, the next maneuver is to rotate the forward end region 562 from the angular orientation θ=θ1 beneath targeted tissue 580 to the orientation θ=0. The rotation thus brings the electrode into intersection with cut indicator line 584 as represented by dashed cut indicator line 596. At position 570, electrosurgical excitation of the electrode 570 may be interrupted to the extent that it is terminated for the procedure and the cut tissue interface that is back-filled with barrier or necrotizing fluid is represented by the filled interface outline 598. Electrode 570 then is retracted fully within the deployment slot 568.

Figure 35E:
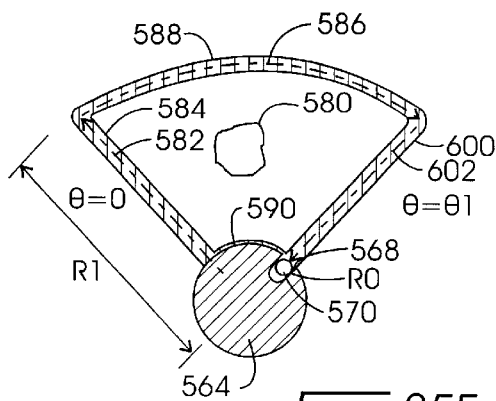

Another option for the practitioner is represented in connection with FIG. 35E. This procedure typically will involve the vascular isolation of smaller targeted tissue volumes 580. In the figure, following the completion of the cut represented at cut indicator line 586 and the filling of the resultant cut interface as represented at 588, the electrode 570 is retracted to a position within the deployment portion slot 568, for example to the position shown where the electrode is aligned with the support member surface 590. This cut maneuver is represented by dashed cut indicator line 600. From the noted position of electrode 570, the tissue interface developed by the cut 600 is back-filled with barrier or necrotizing fluid as represented by the filled interface outline 602. The procedure for filling interface 600 also can be carried out from fully retracted orientation of the electrode 570 within the deployment slot 568.

By virtue of the insertion of the forward end region 562 of support member 564 into adjacency with the "lower" side of the targeted tissue volume 580, a mechanical cut will be in evidence about its "bottom" side at cylindrical surface 590. The act of filling the cut 600 with barrier fluid also will tend to fill the interface between surface 590 and tissue. Such filling also may occur with the filling represented at 584 carried out in connection with the initial cutting step of the procedure.

Figure 36:
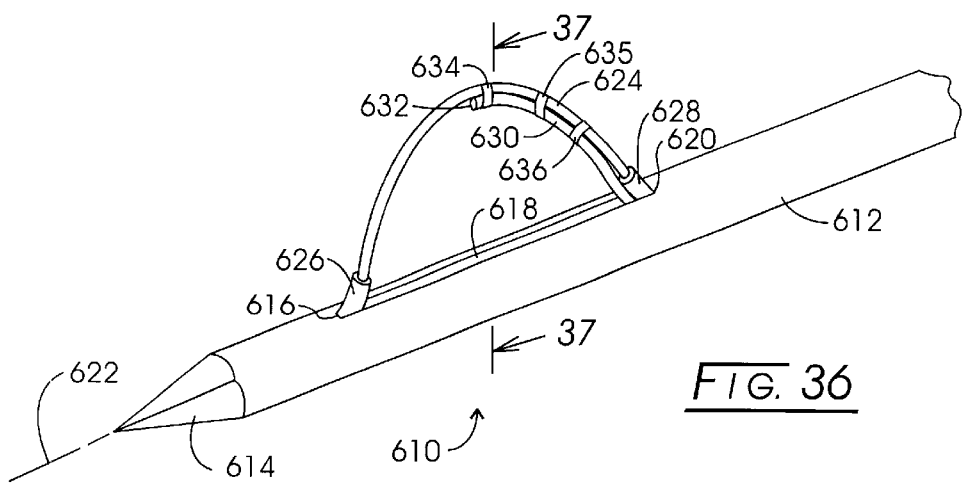
FIG. 36 is a perspective view of the forward end region of another embodiment of the instrument of the invention.

Referring to FIG. 36, another instrument adaptation for expressing barrier or necrotizing fluid within the electrosurgically cut tissue interface developed with the system of the invention is revealed. In the figure, the forward end region 610 of a support member 612 is seen extending to a tip 614. Adjacent tip 614, commencing with a forward location 616, is a slot shaped deployment portion 618 which extends to a rearward location 620. The support member 612 is symmetrically disposed about a longitudinal axis 622 and, as before, slidably supports a thin, resilient electrode 624 having a distal end fixed to the support member 612 adjacent the tip 614 and which is electrically insulated from the member 612 by an electrically insulative sleeve 626. Electrode 624 extends slidably through an electrically insulative sleeve 628 seen extending through the deployment slot 618 adjacent rearward location 620. In the fashion described above, the electrode 624 is compressively urged into an arch formation when deployed from an insertion mode of operation of the instrument. Alternately, the electrode 624 is retracted by urging it rearwardly from the vicinity of the base region of the instrument. For the barrier fluid disbursement embodiment of the figure, a barrier fluid delivery conduit is provided which is slidably mounted within a fluid delivery channel within support member 612. The flexible output portion of that electrically insulative conduit is shown extending to a barrier fluid outlet 632 located at about the midpoint of the deployment portion 618. Conduit portion 630 is coupled to the underside of the electrode 624 by a sequence of electrically insulative and heat resistant thin straps 634–636. With the arrangement shown, the conduit component 630 may be deployed by urging it forwardly simultaneously with the compressive deployment of electrode 624. Alternately, the conduit component 630 may be made of a flexible material permitting it to stretch to the orientation shown. The later approach becomes feasible where the instruments are designed for smaller tissue volume and the longitudinal extent of translation of electrode 624 is quite limited in extent. Guidance and support is supplied to the tubular component 630 during deployment, as well as during retraction by the side surfaces of the slot 618. With the arrangement, the outlet 632 will be positioned essentially at the midpoint of a given electrosurgical cut to facilitate dispersing barrier fluid within the electrosurgical cut interface evolved at the termination of a cut maneuver. Some flexure may be provided at the strap 634–636 to permit the flexible tubular component 630 to pivot about the underside of electrode 624 to therefore allow it to "follow" the electrode as it carries out a transverse pivotal or retracting maneuver. However, during retraction, the side surfaces of the deployment slot 618 will cause the tubular component 630 to reassume the electrode underside orientation shown in FIG. 36 as it approaches a fully nested orientation. A material suited for forming the straps 634–636 may, for example, be the earlier described "Kapton" material.

Figure 37:
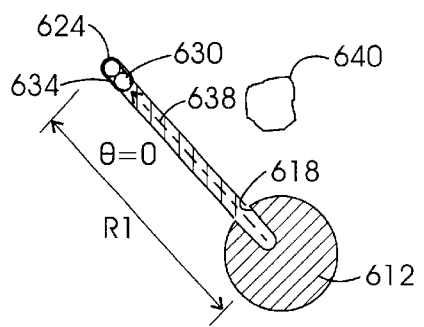
FIG. 37 is a schematic sectional views taken through the plane 37—37 shown in FIG. 36.

The maneuvering of forward end region 610 as well as electrode 624 and associated tubular component 630 will emulate the maneuvering described above in connection with FIGS. 35A–35E. An initial such maneuver is represented in FIG. 37 where the electrode 624 is seen to have been deployed at a radial angle θ=0 and has produced an electrosurgical cut represented by the dashed cut indicator line 638. In this regard, the electrode 624 has radially deployed a distance indicated as $R_1$ about one side of a targeted tissue volume represented at 640. Tubular component 630 has, "followed" electrode 624 to this arch apex orientation. As noted, the procedure then continues as described in connection with FIG. 35.

Figure 38:
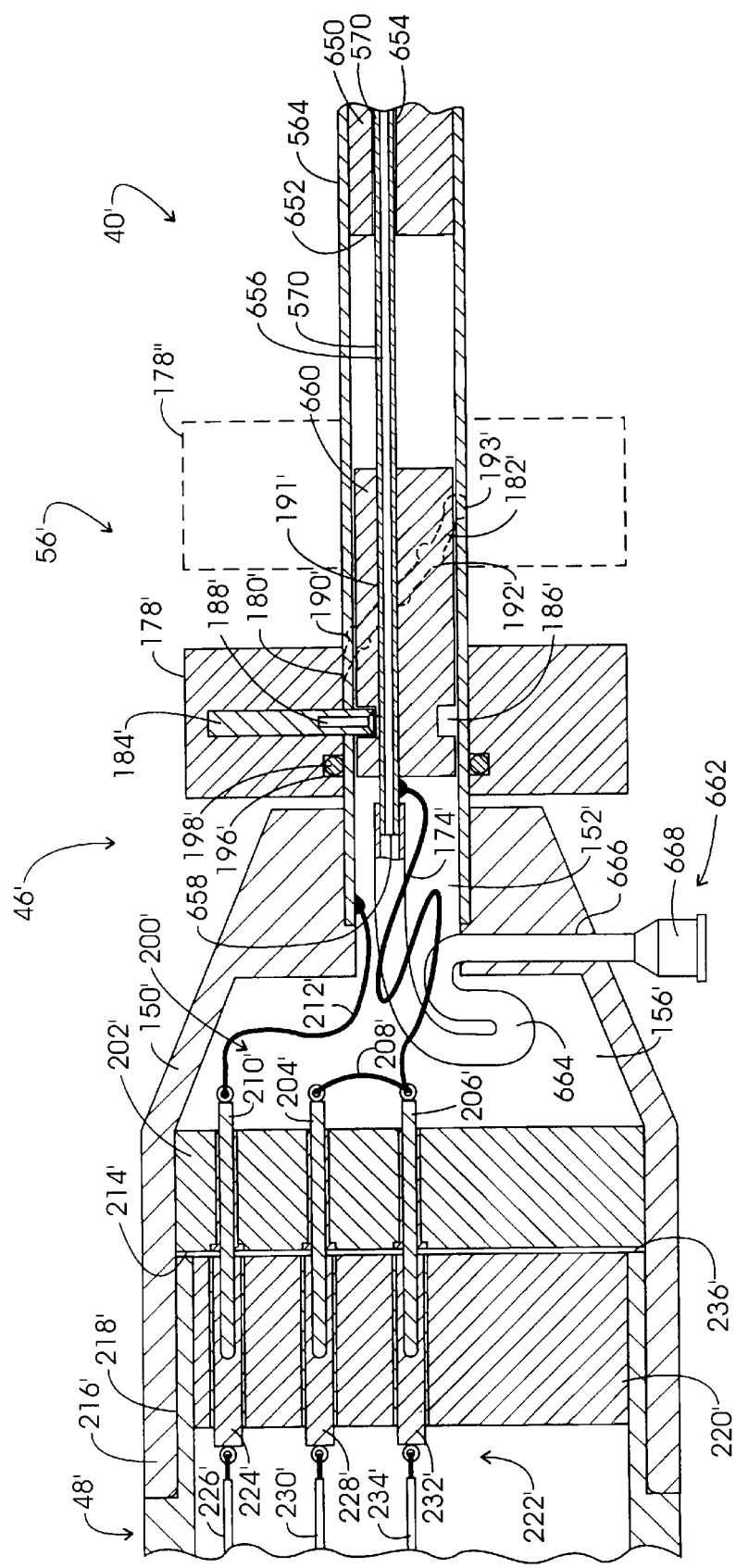
FIG. 38 is a partial sectional view of a base region of another embodiment of the instrument of the invention.

Some modification of the base region earlier described at 46 of the instrument of the invention is called for to accommodate for the barrier or necrotizing fluid delivery embodiments of FIGS. 33 and 36. These modifications are illustrated respectively in connection with FIGS. 38 and 39–40. Where features of this base region remain in common with those identified in FIG. 13, they are identified in the instant figures with the same numeration but in primed fashion. Looking to FIGS. 38, instrument 40' is shown incorporating support member 564 which, at base region 46' is coupled to a removable handle 48'. An actuator assembly is represented generally at 56'. For this embodiment, however, the electrode guide and conduit support, now identified at 650, extends to a rearward face 652 and is fixed within the interior of support member 564. Electrode 570 (from FIG. 33) slidably extends from the forward end region along a support channel 654, in essence, from the rearward face 652 into cylindrical opening 152'. As described above, the electrode 570 is formed having an interior fluid transfer cavity 656 extending rearwardly to an electrode fluid input 658 within cylindrical opening 152'. Electrode 570 is fixed to and extends through electrode drive block 660 and supports that drive block against rotation. Accordingly, with the rotational actuation of the cylindrical control knob 178', electrode drive block 660 will be driven forwardly to, in turn, drive the electrode 570 forwardly an arch defining distance.

To supply barrier fluid to the electrode fluid input 658 and, thus, its interior fluid transfer cavity 656, a barrier fluid delivery assembly represented generally at 662 is provided. Assembly 662 includes a flexible tube 664 which extends through a channel 666 formed within forward base housing 150'. One end of the tube 664 is attached to the fluid input 668 and an amount of "slack" of the tube is folded or wound within the chamber 156' to accommodate for the noted movement of block 660. Tube 664 terminates in a fitment 668 configured for attachment with a reservoir of barrier fluid as, for example, will be provided as a fluid filled hypodermic syringe.

Figure 39:
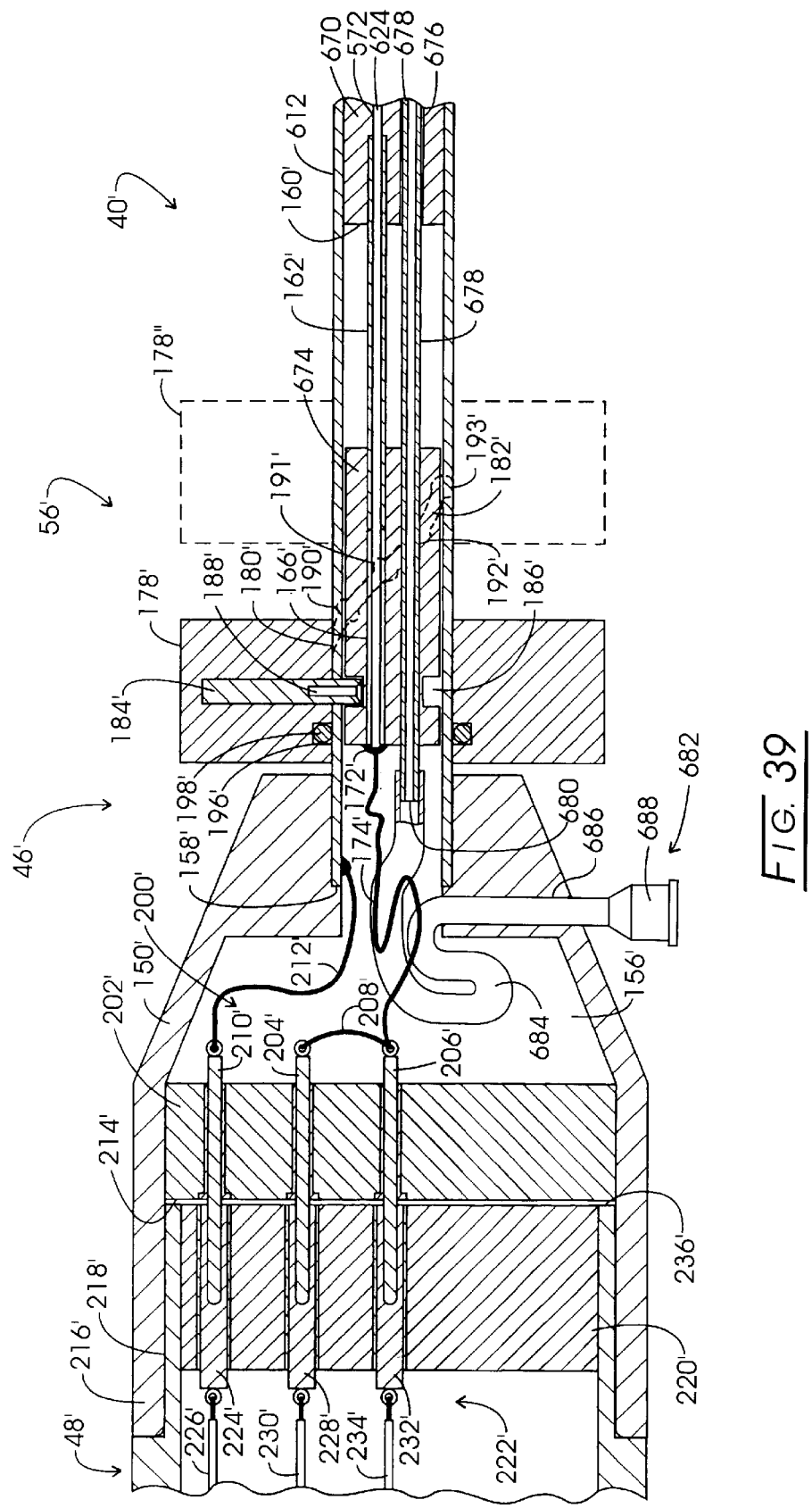
FIG. 39 is a partial sectional view of the base region of another embodiment of an instrument according to the invention.
Figure 40:
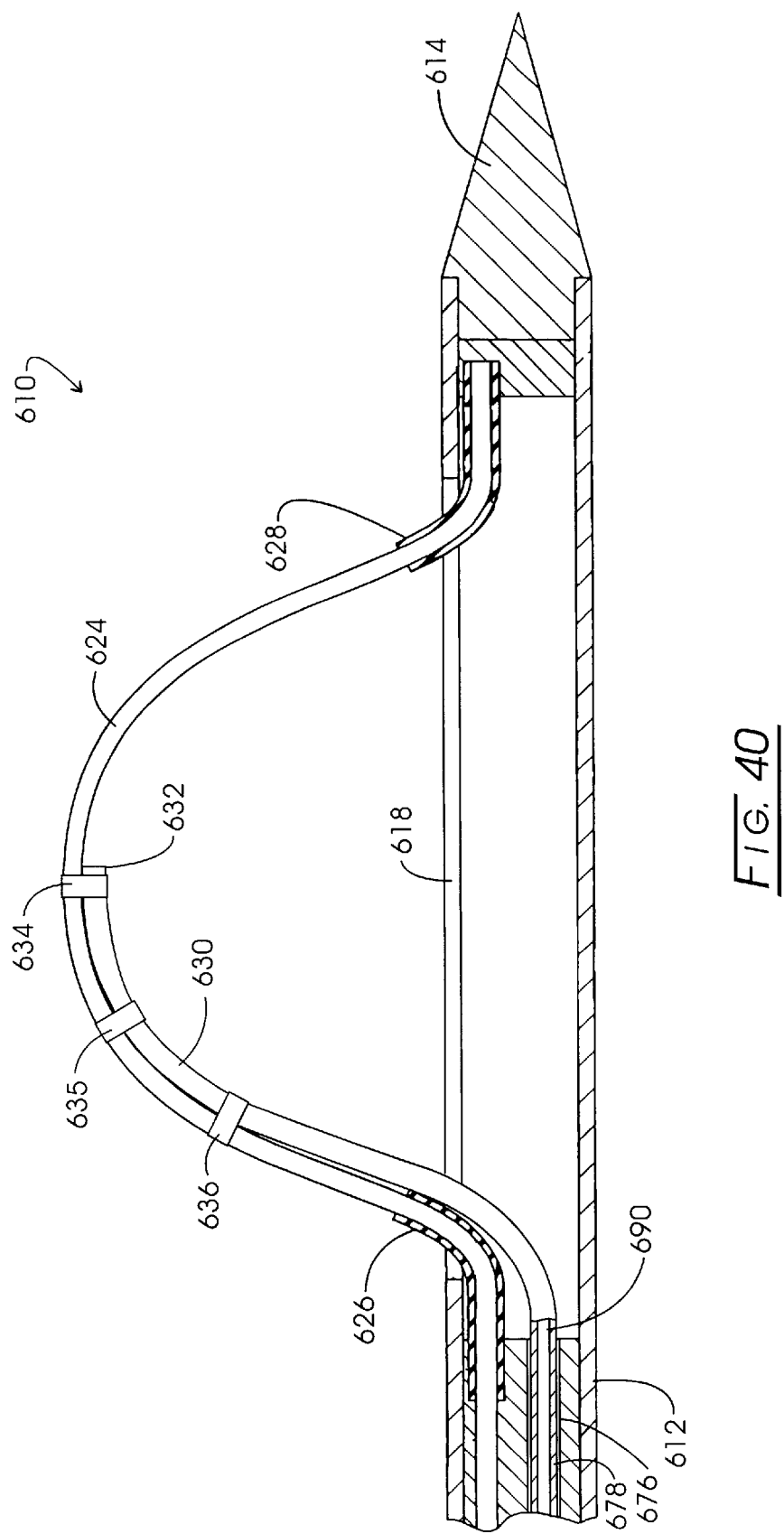
FIG. 40 is a partial sectional view of the forward end region of the instrument shown in FIG. 36.

The base region 46' for the barrier fluid delivery embodiment of FIG. 36 is represented in FIGS. 39 and 40. In FIG. 39, the base end region 46' is shown to include the rearward portion of the support member 612 as it extends to the forward base housing 150'. The electrode guide and conduit support, now as represented at 670, is slidably extending within a channel 572. Channel 572 extends, in turn, to the forward end region 610 (FIG. 36). As in the embodiment of FIG. 13, a rigid sleeve 162' is coupled with the channel 572 and extends in slidable, supporting relationship with an electrode drive block 674 slidably mounted within the interior of support member 612. Electrode 624 is fixed to the drive block 674 at lead connector and adhesion position 172'. Thus, as in the embodiment of FIG. 13, actuation of the knob 178' moves the electrode forwardly in compression, as well as rearwardly. Support 670 also includes a fluid delivery channel 676 within which is slidably located a fluid delivery conduit 678. Conduit 678 extends through and is fixed to drive block 674 and exits from its rear face to a conduit fluid input 680.

Barrier fluid is introduced into the conduit fluid input 680 of delivery conduit 678 from a barrier fluid delivery assembly represented generally at 682. As before, the assembly 682 includes a flexible delivery tube, for example, formed of silicone which is shown at 684 extending through a fluid delivery channel 686 into cavity 156' and connection with fluid input 680. Tube 684 is provided having an extended length or "slack" permitting it to accommodate for the forward movement of drive block 674. A fitment 688 is attached to the opposite end of tube the 684 which is included for connection with a fluid barrier reservoir such as a hypodermic syringe.

Forward end region 610 is shown in FIG. 40. In this regard, the flexible outward portion or tube is shown as a discrete component 630 attached to the fluid outlet 690. With the arrangement, the outlet 690 moves forwardly with the fluid delivery conduit 678 simultaneously with the movement of electrode 624. This deploying movement enhances the flexibility of the flexible tube 630 with respect to its suspension straps 634–636 allowing it to "follow" the electrode 624. The sides of the slot deployment portion 618, in particular, support and realign the tube 630 beneath the electrode 624 during a retraction procedure as well as during deployment.

Figure 41:
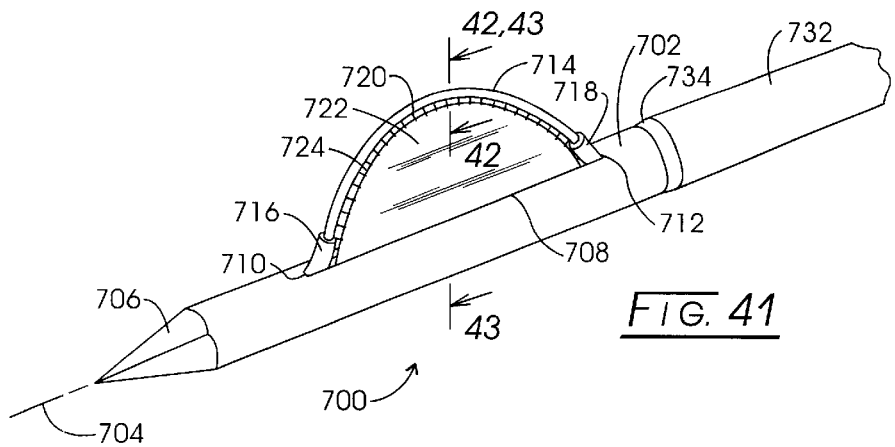
FIG. 41 is a perspective view of the forward end region of another embodiment of an instrument according to the invention.
Figure 42:
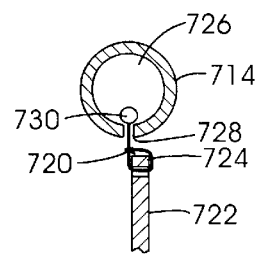
FIG. 42 is a sectional view taken through the plane 42—42 shown in FIG. 41.

The barrier function for retarding neovascularization may be implemented with a thin or membranous flexible film or shroud having an outwardly deployed edge which is pulled behind the deployed arch-shaped electrode. Referring to FIG. 41, the forward end region 700 of a support member 702 is depicted incorporating this embodiment. The forward region 700 of support member 702 is cylindrical and is symmetrically disposed about a longitudinal axis 704 extending to a trocar shaped tip 706. A slot shaped deployment region is shown at 708 extending between a forward location 710 and a rearward location 712. Thin, resilient electrode 714 is shown in its arch-shaped deployed formation extending from fixed association with an electrically insulative sleeve 716 protruding at forward location 710 and is shown in slidable relationship with a flexible electrically insulative sleeve 718 adjacent rearward location 712. Suspended by an array 720 of suture-like, anatomically resorbable connectors attached to the underside of electrode 714 is a thin, flexible, membranous and anatomically resorbable barrier shroud 722. The outer edge 724 of the shroud 722 is retained in adjacency with the underside of electrode 714 with an arrangement revealed in FIG. 42. Looking to that figure, electrode 714 is seen to have an internally disposed cavity 726 and an lower disposed elongate slot 728. An electrically insulative connector rod 730 is attached to one end of each of the connectors of the array 720, the opposite end of which is threaded through the shroud 722 adjacent its outer edge 724. The shroud 722 may be formed of a resorbable material similar to those used in the manufacturer of resorbable sutures such as lactide/glycolide family of polymers. The internally disposed portion of the shroud 722 may be wound, for example, upon a freely rotating mandrel (not shown). Following a procedure wherein the shroud 722 has, in effect, circumscribed the targeted tissue, the electrode 714 will have been retracted and a cylindrical severing member 732 having an annular shaped cutting edge 734 is slid toward and across forward location 710 to sever the shroud 722 at a location in adjacency with the surface of support member 702 along the deployment slot 708.

Figure 43A:
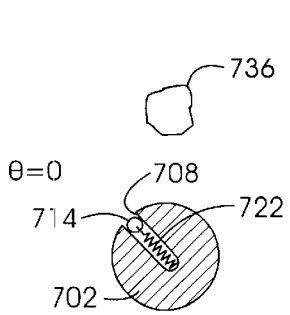
FIGS. 43A–43D are partial sectional views taken through the plane 43—43 shown in FIG. 41 and schematically representing a sequence of operational maneuvers.
Figure 43B:
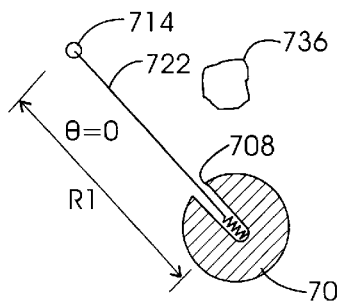
Figure 43C:
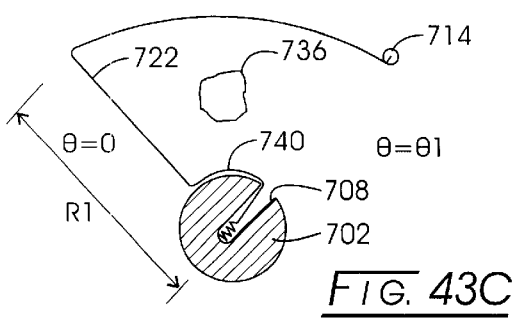
Figure 43D:
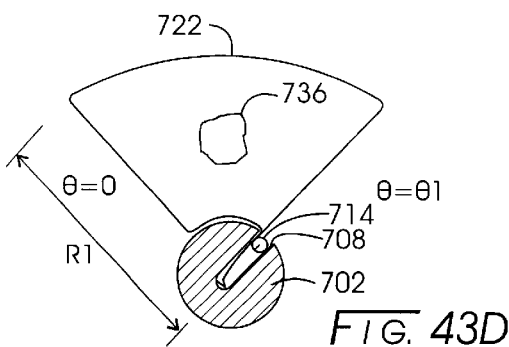

Referring to FIGS. 43A–43D, the preferred maneuvering arrangement for the instrument of FIG. 41 is sequentially portrayed. As before, the figures represent a sectional view of forward end region 700 taken through the apex of the arch formation evoked with the electrode 714. In FIG. 43A, the instrument is in an insertion mode, the forward end region 700 having been inserted within viable tissue in adjacency with targeted tissue represented symbolically at 736. The angular orientation of the forward end region 700 is designated as $\theta=0$. Looking to FIG. 43B, the electrode 714 is electrosurgically excited into a cutting mode and is deployed into an arch formation having an arch apex radius shown as R1, the membranous shroud 722 having been withdrawn from its stored location within support member 702 behind electrode 714. This evokes a cutting locus along one side of targeted tissue volume 736 to a radial extent R1 wherein the electrode 714 may be pivoted with the forward end region 700 of the support member 702 over the top of the targeted tissue volume 736. Looking to FIG. 43C, the electrode remains deployed at radius R1 as the forward end region 700 of support member 702 is pivoted to the position $\theta=\theta 1$, while the electrode 714 is electrosurgically excited to carry out an arcuate cut pulling the shroud 722 from its stored location within the deployment slot 708. Note that the shroud 722 has been drawn across a cylindrical cut surface 740 of the support member 702 as this pivoting activity is carried out from angular orientation $\theta=0$ to $\theta=\theta 1$. Thus, the shroud 722 is positioned over a tissue cut surface which has not been electrosurgically parted. As represented in FIG. 43D, the electrode 714 then is electrosurgically excited and retracted into the deployment slot 708, again pulling the shroud 722 behind it along its locus of cut. Subsequent to the steps represented in this FIGS. 43D, the severing member 732 is urged forwardly to sever the shroud 722 from connection with the support member 702.

In the event that it is desired to carry out an electrosurgical cut below the targeted tissue 736, then the initial maneuver will be to deploy the electrode 714 to the earlier described radius R2 (FIGS. 19B, 19C) and carry out a circumscription maneuver as a pivoting one from θ=0 to θ=θ1.

As is apparent from the discourse above, the expression of barrier fluid or necrotizing agent into the tissue interface developed from electrosurgical cutting may be achieved with a variety of instrument modalities ranging from simply expressing the fluid from the vicinity of the deployment slot following a circumscriptive isolation of targeted tissue to the expression of the fluid in the course of the locus of movement of the electrode about the developing interface. It should be borne to mind that two additional or supplemental approaches have been discussed above. In this regard, one such approach is to employ a "blend" electrosurgical output which carries out both cutting and coagulation at the cut tissue interface. A similar result can be obtained by reiterating the entire circumscription procedure utilizing the coagulating output of the electrosurgical generator for exciting the electrode.

Figure 44A:
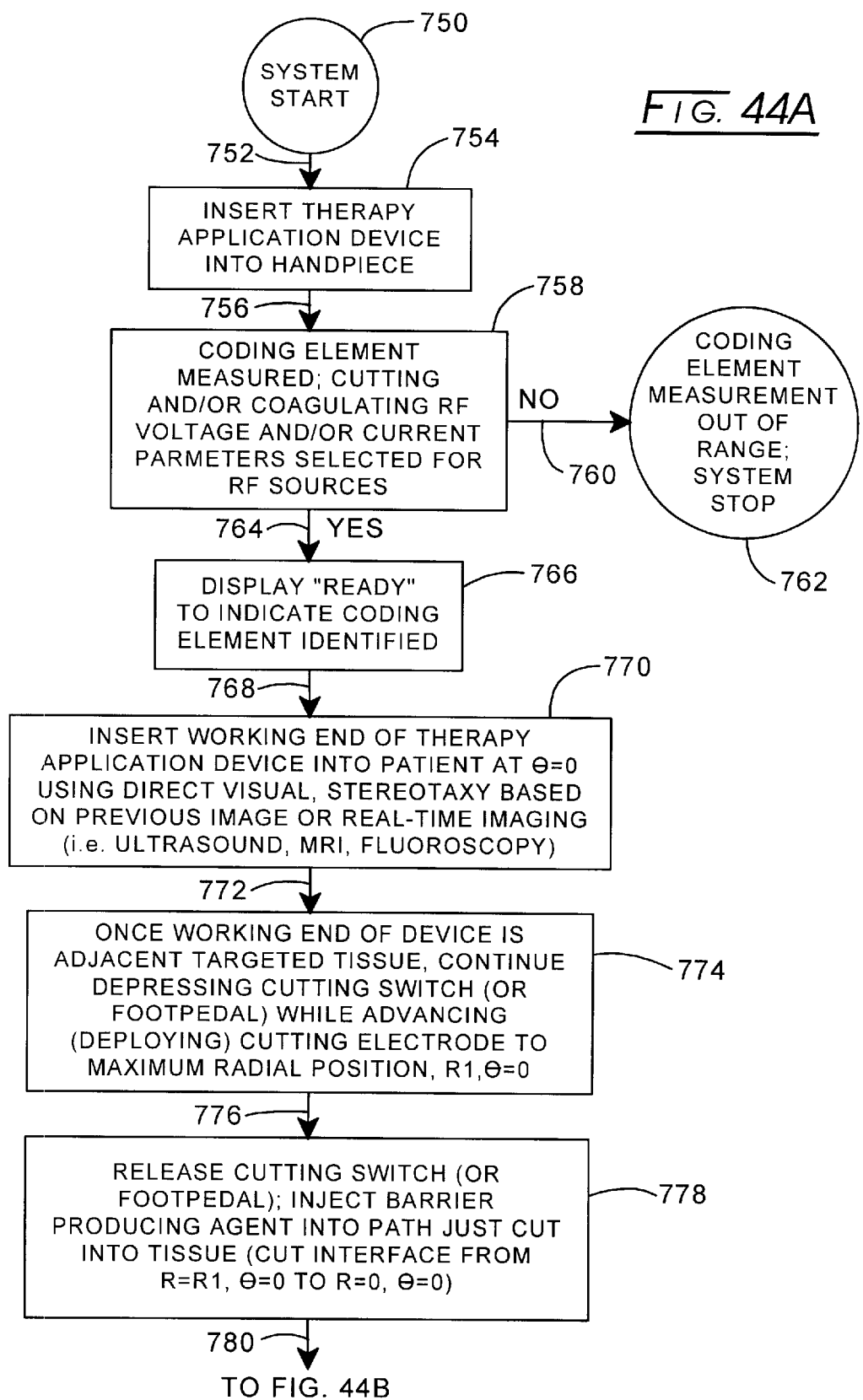

Referring to FIG. 44A, a flowchart looking to the barrier fluid introduction methodology is set forth. In the figure, the system is shown to start-up, as represented at mode 750, whereupon as is represented at arrow 752 and block 754, the instrument 40, which may be disposable, is inserted within the handle 48. It should be pointed out that the forward end region portion as well as eventually the entire instrument 40 may be employed with a variety of manipulative devices including, for instance, robotically performing instrumentation as well as catheters.

When handle and instrument are coupled together, as represented at arrow 756 and block 758, the control assembly of the system interrogates the coding elements within instrument 40 to automatically select proper electrode excitation parameters. Where that interrogation shows an out-of-range condition or like aberration, then as represented at arrow 760 and node 762, the system stops pending correction. Where appropriate parameter selection has been accomplished, then as represented at arrow 764 and block 756, visual and aural cues are given to the operator that the system is ready. Cueing has been made available, for example, in conjunction with LEDs 22–25 at console 12 as well as LED array 72 and further through aural arrangement extending from speaker grill 28. (FIG. 1). The procedure then continues as represented at arrow 768 and block 770 wherein the working end or forward end region of the instrument is inserted into the patient into adjacency with one side of the targeted tissue volume peripheral extent at an angular orientation represented as θ=0. Then, as represented at arrow 772 and block 774, the electrode is deployed while being electrosurgically excited. This creates the first cut interface wherein the apex region of the arch created by electrode deployment is located to be pivotal over the "top" of the peripheral extent of the targeted tissue volume. As represented at arrow 776 and block 778, for one barrier fluid positioning approach, the electrosurgical excitation of the electrode is interrupted and barrier fluid is injected within the tissue interface established by that preceding cutting activity. Fluid injection may be from the vicinity of the electrode itself as discussed in conjunction with FIGS. 33–37 or from the region of the deployment slot, as discussed in conjunction with FIGS. 7 through 13, 16, 24 through 27, and 28 through 32.

The procedure continues as represented at arrow 780 which reappears in FIG. 44B extending to block 782 providing, in turn, for the reexcitation of the electrode and rotating of the forward region such that the apex of the electrode passes over the peripheral extent (top) of the targeted tissue volume to a location such that it may circumscribe the opposite side of the tissue volume upon retractive manipulation.

This procedure then continues as represented at arrow 784 and block 786 which provide for the interruption of electrode excitation and the introduction of barrier fluid or agent into the tissue interface representing the next proceeding cut. As noted, this can be carried out from a conduit having an outlet adjacent the electrode itself or from the deployment region of the support member. The methodology continues, as represented at arrow 788, to the maneuver represented at block 790 wherein electrosurgical excitation of the electrode again ensues and the electrode is retracted to the earlier-described radial position R2, a location just above the surface of the support member as described, for instance, in connection with FIG. 35C.

As described in connection with arrow 792 and block 794, excitation of the electrode then may be stopped and barrier fluid injected into the tissue cut interface just previously formed. Alternately, the interface so formed may be filled with barrier fluid from a location at the deployment portion or slot. This completes a full circumscription of the targeted tissue volume, an orange segment shaped volume being circumscribed electrosurgically about the tissue volume both across its top and bottom peripheries.

The program then continues as represented at arrow 796 and block 798 wherein electrosurgical excitation of the electrode is reinstated and the forward end region is pivoted to its original rotational orientation.

An alternative step then may be undertaken, particularly where targeted tissue of relatively smaller volume is under circumscriptive vascular isolation treatment. In this regard, the electrosurgical cut represented at block 798 is dismissed and the electrode is retracted into its fully nested orientation. There will have existed a tissue severance of the tissue volume occasioned by the forward end region surface of the support member, for instance as described at 590 in FIG. 35C. While a surface necrosis of the tissue at the resultant cut interface will not have occurred, its surface extent is quite small and the next succeeding step additionally may position barrier fluid within that interface.

This alternative approach is represented at dashed arrow 800 and dashed block 802 which provides an alternate procedure supplanting the steps represented at block 790, 794 and 798. At block 802, a procedure is provided for exciting the electrode while retracting it to its nested orientation radially represented herein at R0, a location permitting the expression of barrier fluid and subsequent removal of the forward end region from adjacency with the targeted tissue.

The program then may proceed either from block 802 or from block 798 as represented at arrow 804 to the step represented at block 806. At this point in the procedure, the electrosurgical excitation of the electrode is terminated and barrier producing agent is injected into the path which was just cut. With respect to the procedure block 802, fluid injection is made into the cut interface created by the support member at the forward end region. The procedure then continues as represented at arrow 808 which reappears in FIG. 44C. Arrow 808 extends to block 810 which provides for an alternative method wherein barrier fluid is injected into the entire circumscriptive tissue cut interface following the circumscriptive cutting procedure. As represented by dashed arrow and dashed block 814, another alternative step may be undertaken. With this latter procedure, an embodiment wherein barrier fluid is expressed in adjacency with the electrode is provided and the electrode deployment, pivoting and retraction maneuvers are reiterated while barrier fluid is expressed from the vicinity of the electrode.

A further alternative is represented in conjunction with dashed arrow 816 and dashed block 818. The procedure described at block 818 is one wherein an electrosurgical coagulating maneuver is carried out as repeated maneuver wherein circumscription of the targeted tissue volume occurs. Such circumscription is performed with the electrode in conjunction with its deployment, pivoting and retraction maneuvers described above in combination with a coagulation output evolved from the electrosurgical generator 12 (FIG. 1).

The program then continues as represented at dashed arrow 820 leading to block 822 which again describes the termination of the electrode manipulation activity wherein it is retracted into its nested orientation radially designated at R=0.

Arrow 824 and node 826, provide that the devitalizaton of the targeted tissue volume has been completed. Then, as represented at arrow 828 and block 830, the forward end region or working end of the instrument is removed from the patient, to terminate the procedure. Alternatively, it may be applied at a different anatomical location for a next procedure.

As discussed above, the instrumentation of the present invention has application in a variety of electrosurgical procedural modalities in consequence of the stability of the electrode arch formation and the accuracy of any resultant electrosurgical cut carried out. One such application is concerned with cardiac dysrhythmias induced by reentry circuits. A reentry circuit, in the parlance of electrical systems, is a relatively narrow and extensive channel of tissue along which abherrent current, in the nature of a short circuit path passes. Induction of the tachycardia in the past has been carried out with a intravascular catheter carrying positioning electrodes which are used to manipulate a catheter tip into adjacency with a targeted interior wall of the heart. Electrosurgically ablating current is delivered to a monopolar electrosurgically ablating performance at the tip of the catheter for an interval of about five to ten seconds to achieve a desired electrophysiologic effect. Such tissue ablation is relatively expansive in extent. Where the desired effect is not achieved in a given attempt, then the catheter is repositioned and the procedure reiterated at different locations along the myocardium. Generally, this electrosurgical activity occurs for twenty to sixty seconds to produce a maximal lesion. The procedure is generally successful and carries out the formation of an impedance based interruption of the reentry circuit by evoking an electrosurgically developed impedance to current flow. The present embodiment of the invention avoids the use of an ablation form treatment modality in favor of the accuracy of the deployed arch-forming electrode.

Figure 45:
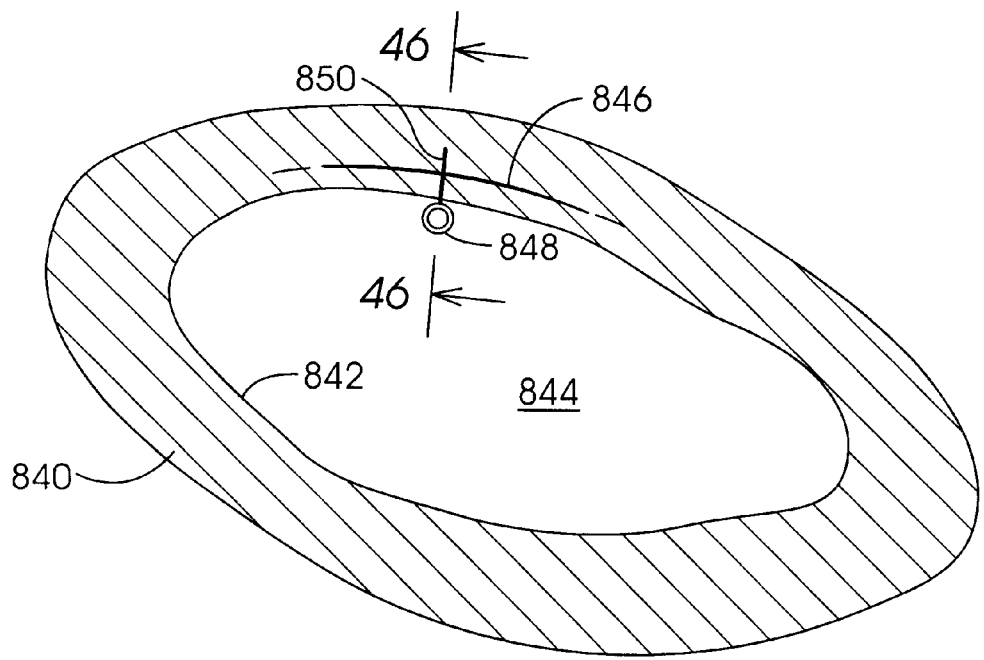
FIG. 45 is a schematic sectional view of a chamber of a heart showing the positioning of a forward end region of another embodiment of an instrument according to the invention.

Referring to FIG. 45, a schematic section of a heart wall is shown at 840 having an endocardial interior heart wall surface 842. Wall surface 842 will surmount a heart chamber represented at 844 such as the right or left ventricle. The figure shows the path of a reentry circuit 846. In carrying out the treatment modality of the invention, an intravascular catheter 852 (FIG. 46) is configured to incorporate a tip having a modified forward end region 854 of the instrument of the invention. This will include a noted deployment region slot 848 and thin resilient electrode 850 which is deployable in compression by manipulation from the base region of the catheter into an arch formation while being electrosurgically excited to carry out an electrosurgical cut defined by the thin electrode between its forward and rearward locations. Catheter 852, with its modified tip, is percutaneously inserted into the patient and intravascularily guided to the position within the chamber 844. The deployment region slot portion of the tip of the instrument is shown at 848 having deployed an electrode 850 into an arch formation while being electrosurgically excited to provide a cut with an impedance defining tissue interface. Looking additionally to FIG. 46, the reentry circuit 846 is seen to be, as discussed above, a relatively narrow or discrete path for current flow, while the electrode 850 of catheter 852 is seen to be deployed in an arch formation electrosurgically having cut through the myocardium 842 and past the location of the circuit path 846. The catheter 852 will have guided its forward end region 854 into adjacency with the heart interior wall surface 842 such that the deployment slot or portion 848 extends across or embraces the region of path 846. This positioning of the catheter 852 and forward end region 854 is carried out by two positioning surface electrodes as are conventionally employed with this procedure and are shown at spaced apart locations 856 and 858. Such positioning is carried out by remotely observing alterations in electrical parameters such as impedance variation, occasioned by of the reentry circuit 846. With the present invention, however, it is necessary to position the deployment slot portion 848 into appropriate adjacency with the heart wall surface 842. This is achieved by providing surface electrodes 860 and 862 at the forward end region 854 which are of limited circumferential extent and aligned with the deployment slot portion 848 and which may respond in similar manner as electrodes 856 and 858, but only when the slot 848 is adequately adjacent the wall 842. Transverse transection of heart wall 840 then is carried out. The degree of transverse orientation of the slot and electrode 850 is dependent simply upon the requirement for interrupting reentry circuit path 846 an amount effective to gain normal heart functionation. This interruption, for example, achieved through an impedance formation within the reentry circuit path by the generation of an necrotic tissue interface. The procedure may be performed using a conventional electrosurgical cutting excitation of electrode 850 or with a "blend" cutting activity.

Figure 46:
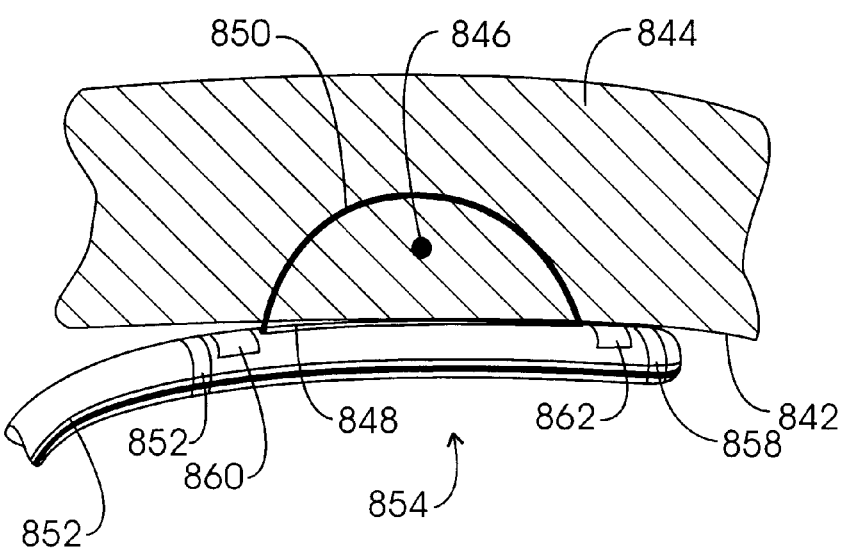
FIG. 46 is a partial sectional view taken through the plane 46—46 in FIG. 45.

Referring to FIG. 47, a flowchart describing the procedure for utilizing the embodiment of FIGS. 45 and 46 is set forth. In the figure, the procedure commences as represented at block 870. The modified intravascular catheter is introduced into an artery or vein depending upon which chamber of the heart which is involved with the reentry circuit. Then, as represented at arrow 872 and block 874 the distal or forward end region of the catheter is positioned adjacent the abnormal electrical pathway or reentry circuit. As represented at arrow 876 and block 878, it is necessary to orient the catheter so that the deploying electrode is facing the interior heart wall and is generally transverse to the circuit path 846. In the latter regard, it is necessary to interrupt the path and establish a form of tissue interface developed impedance to the flow of current along the path. As noted above, this may be carried out in conjunction with surface electrodes 860 and 862 (FIG. 46). As represented at arrow 880 and block 882, as the electrode is deployed, it is electrosurgically excited either with a cutting or blend output waveform and deployment continues as the condition of the reentry circuit 846 is monitored. When interruption of that circuit is achieved, either with a single or with multiple positioning of the forward end region 854, then, as represented at arrow 884 and block 886 the electrode 850 is retracted into a nested orientation within the deployment slot 848. Then, as represented at arrow 888 and block 890, the catheter is removed or moved to the next location.

The instrument architecture described above has been one wherein the thin, resilient electrically conductive electrode has been mounted in electrical isolation from the support member. For example, in FIG. 7, electrode 54 is seen to be electrically insulated by sleeves as at 86 and 88 and extends through an electrically insulative guide and conduit support 136. In a preferred arrangement, however, the components supporting the electrode are in electrical contact with it and thus, they are at the same potential during intervals of electrode excitation. The support member itself, however, is covered with a thin but effective layer of insulation such that it is safely electrically isolated from the patient. Accordingly, arcing phenomena between components is avoided.

Referring to FIG. 48, the forward end region of an instrument incorporating this preferred architecture is represented generally at 900. Region 900 incorporates an electrically conductive cylindrical support member 902 which may, for example, be formed of stainless steel. This member 902 is symmetrically disposed about an axis 904 and is seen to extend to an integrally formed or pointed trocar-type tip 906. Extending through the support member 902 is an elongate bore 908 which terminates in an end surface 910. As in the earlier embodiments, support member 902 incorporates a slot-shaped deployment portion 912 extending along the axis 904 from a forward location 914 to a rearward location 916. Extending within the bore 908 is an elongate thin, resilient and electrically conductive electrode 918, the distal end 920 of which is fixed within a securement region 922 of bore 908. In this regard, the distal tip of the electrode 918 preferably is fixed in abutting relationship with the end surface 910. In a preferred arrangement, the fixing of the distal end 920 is carried out with a quadrature based crimping procedure. Looking to FIG. 49, four compressive crimp indentations are represented at 924–927 developing respective compressive attachments 928–931.

As in the earlier embodiment, the electrode 918 is deployed from the deployment portion 912 by being compressively urged forwardly to assume an arch formation represented, for example, at 918' in phantom. Looking additionally to FIG. 50, the electrode 918 within the deployment portion 916 is seen to be slightly bent outwardly within the slot-shaped deployment portion 912. In this regard, note that the electrode, in general, extends above the bottom surface 934 of the bore 908 as it extends along the slot-shaped deployment portion 912. Electrode 918 additionally is seen to extend rearwardly from the rearward location 916 within the bore 908. This slidable relationship is represented in FIG. 51 by the annular gap 936.

An electrically insulating layer is disposed on the exterior surfaces of the support member 902 as is represented at 938. Note that the layer 938 covers the tip region 906 and extends over the edges of slot-shaped deployment region 912. This extension of the coating is shown in FIG. 50 at 940 extending over deployment slot side surface 942 and at 944 extending over the deployment slot side surface 946. Similarly, FIG. 48 reveals that the insulative coating extends over rearward location 916 as at 948 and over forward location 914 as at 950. A suitable electrically insulating material is a vapor-phase-polymerized conformal coating marketed under the trade designation "Parylene". Coatings are available from Parylene Coating Surface Companies such as Specialty Coating Systems, of Indianapolis, Ind. The insulative material 938 will have a thickness from about 0.0002 inch to 0.020 inch and preferably in a range of about 0.0005 inch to 0.003 inch.

Since certain changes may be made in the above-described apparatus, method and system without departing from the scope of the invention herein involved, it is intended that all matter contained in the description thereof or shown in the accompanying drawings shall be interpreted as illustrative and not in a limiting sense.

What is claimed is:

1. A method for carrying out the circumscriptive isolation of targeted tissue exhibiting a given peripheral extent and surmounted by viable tissue, comprising the steps of:

(a) providing an electrosurgical generator assembly having an electrosurgical return, controllable to generate a first output for carrying out electrosurgical cutting of tissue;

(b) providing an instrument electrically coupled with said electrosurgical generator assembly, having a support member extending between a tip and a base region, having a forward end region extending along a longitudinal axis movable with respect to said targeted tissue, and having an electrode at said forward end region actuable for deployment from a retracted orientation to deployed orientations and from said deployed orientations toward a retracted orientation;

(c) positioning said instrument forward end region within said viable tissue in adjacency with said targeted tissue peripheral extent with said electrode in a said retracted orientation;

actuating said instrument to deploy said electrode in adjacency with said targeted tissue peripheral extent and thence along and in adjacency with said targeted tissue peripheral extent and retracting said electrode toward a retracted orientation to describe a tissue isolating locus of movement within said viable tissue about said targeted tissue peripheral extent; and (e) simultaneously with said step (d) controlling said electrosurgical generator assembly to apply said first output to said electrode in electrical association with said electrosurgical return to establish an electrosurgical cut along said locus of movement of said electrode effective to provide a substantial vascular isolation of said targeted tissue from said viable tissue.

2. The method of claim 1 in which:

said step (a) provides a said electrosurgical generator assembly as being controllable to generate a second output for carrying out the coagulation of tissue;

including the steps of:

(f) reiterating said step (d); and (g) simultaneously with said step (f) controlling said electrosurgical generator assembly to apply said second output to said electrode in electrical association with said return to provide electrosurgical coagulation along said electrosurgical cut derived in said step (e).

3. The method of claim 2 in which:

said step (b) provides said instrument as having a said electrode which is thin, resilient and forming an arch shaped profile extending outwardly from two spaced apart locations when deployed from a said retracted orientation; and said step (d) comprises the actuating steps of:

(d1) urging said electrode outwardly to effect formation of said arch shaped profile and the location thereof adjacent one side of said targeted tissue peripheral extent, (d2) thence said actuation is further carried out by effecting pivotal rotation of said electrode along a said locus circumscribing a continuous portion of said targeted tissue peripheral extent.

4. The method of claim 1 in which:

said step (a) provides a said electrosurgical generator assembly as being controllable to generate a second output for carrying out the coagulation of tissue and is further controllable to provide a blend output alternately generating said first output and said second output in accordance with a predetermined duty cycle; and said step (e) is carried out by controlling said electrosurgical generator assembly to apply said blend output to said electrode in electrical association with electrosurgical return to establish a said electrosurgical cut with adjacent coagulated cut surfaces.

5. The method of claim 1 in which:

said step (b) provides said instrument with a fluid delivery channel extending from a fluid input in the vicinity of said base region to a fluid output at said forward end region and providing a supply of barrier fluid effective to retard the rate of neovascularization in fluid transfer communication with said fluid input; and including the step of:
(f) expressing said barrier fluid from said fluid output for dispersion within said electrosurgical cut.

6. The method of claim 1 in which:

said step (b) provides said instrument as having a said electrode which is thin and resilient, having a distal end connected with said support member at a connection location adjacent said tip and extending therefrom an arch defining distance; and said step (d) comprises the actuating steps of:
(d1) urging said electrode forwardly toward said tip in compression to effect its deployment from an initial angular orientation of said forward end region as an outward movement in adjacency with one side of said peripheral extent of said targeted tissue, said outward movement being to an extent curving said electrode into an outwardly depending arch formation having an arch apex of circumscription height extensible over said targeted tissue when said forward end region is pivoted.
(d2) pivoting said forward end region to a second angular position to, in turn, pivot said electrode over said targeted tissue peripheral extent to a next side thereof opposite said one side,
(d3) effecting retraction of said electrode by urging it rearwardly toward said base region to effect its retracting movement to a retracted orientation below said targeted tissue peripheral extent to effect said electrosurgical cut along three contiguous regions of said targeted tissue peripheral extent.

7. A method for the treatment of an atrial flutter reentry circuit at a heart wall comprising the steps of:

(a) providing a control system including an electrosurgical generator actuable to derive an electrosurgical cutting output and a mapping system controllable for response to an electrical parameter to locate the path of said reentry circuit;

(b) providing an intravascular catheter electrically coupled with said control system, extending from a base region to a tip, having a forward end region adjacent said tip including a deployment slot longitudinally disposed between a forward location adjacent said tip and a rearward location, having a thin, resilient electrode at said forward end region having a distal end fixed to said catheter, extending within said deployment slot during insertion and removal modes and extending within said catheter beyond said rearward location an arch defining distance;

(c) percutaneously introducing said catheter into the vascular system to locate said forward end region within the heart;

(d) controlling said mapping system to locate the current flow position of said reentry circuit with respect to a heart wall;

(e) positioning said deployment slot adjacent said heart wall at said current flow position in a longitudinal orientation effective for deriving a current interrupting impedance;

(f) urging said electrode forwardly toward said tip in compression to effect its deployment outwardly from said deployment slot into an arch formation having an arch apex determined by said arch defining distance;

(g) simultaneously with said step (f), actuating said electrosurgical generator to apply said cutting output to said electrode; and (h) retracting said electrode into said deployment slot by urging it rearwardly.

8. The method of claim 7 in which said steps (d) through (h) are reiterated until said re-entry circuit is beneficially interrupted by the impedance of necrotic tissue formed by said electrode.

9. The method of claim 7 in which:

said step (b) includes the provision of at least one surface electrode at said forward end region aligned with said deployment slot and electrically coupled with said mapping system; and said step (e) is carried out by controlling said mapping system to determine when said surface electrode is in electrically discernable contact with said heart wall.

10. The method of claim 7 in which said step (e) is carried out by positioning said deployment slot wherein its longitudinal extent is generally transversely oriented with respect to said path of said reentry circuit.

11. A method for carrying out the necrosis of a volume of targeted tissue exhibiting a given peripheral extent and surmounted by viable tissue, comprising the steps of:

(a) providing an electrosurgical generator assembly having an electrosurgical return, controllable to generate a first output for carrying out electrosurgical cutting of tissue;

(b) providing an instrument electrically coupled with said electrosurgical generator assembly, having a support member extending between a tip and a base region, having a forward end region extending along a longitudinal axis movable with respect to said targeted tissue, and having an electrode at said forward end region with a distal end fixed to said support member actuable for deployment from a retracted orientation to deployed orientations and from said deployed orientations toward a retracted orientation;

said instrument being provided as having a said electrode which is thin and resilient, having a distal end connected with said support member at a connection location adjacent said tip and extending therefrom an arch defining distance;

(c) positioning said instrument forward end region within said viable tissue in adjacency with said targeted tissue peripheral extent with said electrode in a said retracted orientation;

(d) actuating said instrument to deploy said electrode in adjacency with said targeted tissue peripheral extent and thence along and in adjacency with said targeted tissue peripheral extent by pivoting said forward end region and retracting said electrode toward said retracted orientation to describe a locus of movement about said targeted tissue peripheral extent;

said step (d) comprising the actuating steps of:
  (d1) urging said electrode forwardly toward said tip in compression to effect its deployment from an initial angular orientation of said forward end region as an outward movement in adjacency with one side of said peripheral extent of said targeted tissue, said outward movement being to an extent curving said electrode into an outwardly depending arch formation having an arch apex of circumscription height extensible over said targeted tissue when said forward end region is pivoted,
  (d2) pivoting said forward end region to a second angular position to, in turn, pivot said electrode over said targeted tissue peripheral extent to a next side thereof opposite said one side,
  (d3) effecting retraction of said electrode by urging it rearwardly toward said base region to effect its retracting movement to a retracted orientation below said targeted tissue peripheral extent to effect said electrosurgical cut along three contiguous regions of said targeted tissue peripheral extent,
  (d4) pivoting said forward end region between said second and initial angular orientations to, in turn, pivot said electrode, said locus of movement circumscribing said targeted tissue along four contiguous regions; and (e) simultaneously with said step (d) controlling said electrosurgical generator assembly to apply said first output to said electrode in electrical association with said electrosurgical return to establish an electrosurgical cut along said locus of movement of said electrode effective to provide a substantial vascular isolation of said targeted tissue from said viable tissue.

12. The method of claim 11 in which:
said step (d) includes the step of: (d4) subsequent to said step (d3), pivoting said forward end region from said second to said initial angular orientation to, in turn, pivot said electrode, said locus of movement circumscribing said targeted tissue along four contiguous regions; and
including the step (f2) of expressing said barrier fluid from said fluid output subsequent to said step (d4).

13. A method for carrying out the necrosis of a volume of targeted tissue exhibiting a given peripheral extent and surmounted by viable tissue, comprising the steps of:
(a) providing an electrosurgical generator assembly having an electrosurgical return, controllable to generate a first output for carrying out electrosurgical cutting of tissue;
(b) providing an instrument electrically coupled with said electrosurgical generator assembly, having a support member extending between a tip and a base region, having a forward end region extending along a longitudinal axis movable with respect to said targeted tissue, and having an electrode at said forward end region with a distal end fixed to said support member actuable for deployment from a retracted orientation to deployed orientations and from said deployed orientations toward a retracted orientation,
said instrument being provided as having a said electrode which is thin and resilient, having a distal end connected with said support member at a connection location adjacent said tip and extending therefrom an arch defining distance;
said instrument being further provided with a fluid delivery channel extending from a fluid input in the vicinity of said base region to a fluid output at said forward end region and providing a supply of barrier fluid effective to retard the rate of neovascularization in fluid transfer communication with said fluid input;
(c) positioning said instrument forward end region within said viable tissue in adjacency with said targeted tissue peripheral extent with said electrode in a said retracted orientation;
(d) actuating said instrument to deploy said electrode in adjacency with said targeted tissue peripheral extent and thence along and in adjacency with said targeted tissue peripheral extent by pivoting said forward end region and retracting said electrode toward said retracted orientation to describe a locus of movement about said targeted tissue peripheral extent;

said step (d) comprising the actuating steps of:
  (d1) urging said electrode forwardly toward said tip in compression to effect its deployment from an initial angular orientation of said forward end region as an outward movement in adjacency with one side of said peripheral extent of said targeted tissue, said outward movement being to an extent curving said electrode into an outwardly depending arch formation having an arch apex of circumscription height extensible over said targeted tissue when said forward end region is pivoted,
  (d2) pivoting said forward end region to a second angular position to, in turn, pivot said electrode over said targeted tissue peripheral extent to a next side thereof opposite said one side,
  (d3) effecting retraction of said electrode by urging it rearwardly toward said base region to effect its retracting movement to a retracted orientation below said targeted tissue peripheral extent to effect said electrosurgical cut along three contiguous regions of said targeted tissue peripheral extent;

(e) simultaneously with said step (d) controlling said electrosurgical generator assembly to apply said first output to said electrode in electrical association with said electrosurgical return to establish an electrosurgical cut along said locus of movement of said electrode effective to provide a substantial vascular isolation of said targeted tissue from said viable tissue;

said step (e) including the steps of:
  (e1) upon completion of said step (d1), interrupting said first output and expressing said barrier fluid within said electrosurgical cut;
  (e2) upon completion of said step (d2), interrupting said first output and expressing said barrier fluid within said electrosurgical cut; and
  (e3) upon completion of said step (d3), interrupting said first output and expressing said barrier fluid within said electrosurgical cut.

14. The method of claim 13 or 12 in which said step (b) provides said instrument as having a said electrode with an interior fluid transfer cavity having a cavity fluid input in fluid transfer communication with said fluid delivery channel and said fluid output is formed within said electrode in fluid transfer communication with said cavity.

15. A method for carrying out the necrosis of a volume of targeted tissue exhibiting a given peripheral extent and surmounted by viable tissue, comprising the steps of:

(a) providing an electrosurgical generator assembly having an electrosurgical return, controllable to generate a first output for carrying out electrosurgical cutting of tissue;

(b) providing an instrument electrically coupled with said electrosurgical generator assembly, having a support member extending between a tip and a base region, having a forward end region extending along a longitudinal axis movable with respect to said targeted tissue, and having an electrode at said forward end region with a distal end fixed to said support member actuable for deployment from a retracted orientation to deployed orientations and from said deployed orientations toward a retracted orientation, said instrument being provided as having a said electrode which is thin and resilient, having a distal end connected with said support member at a connection location adjacent said tip and extending therefrom an arch defining distance;

said instrument deployment portion including an outwardly opening slot extending along said longitudinal axis, and including a membranous flexible anatomically resorbable barrier shroud having an outer edge coupled with said electrode, extending within said deployment portion during said insertion mode and deployable by said electrode;

(c) positioning said instrument forward end region within said viable tissue in adjacency with said targeted tissue peripheral extent with said electrode in a said retracted orientation;

(d) actuating said instrument to deploy said electrode in adjacency with said targeted tissue peripheral extent and thence along and in adjacency with said targeted tissue peripheral extent by pivoting said forward end region and retracting said electrode toward said retracted orientation to describe a locus of movement about said targeted tissue peripheral extent;

said step (d) comprising the actuating steps of:

(d1) urging said electrode forwardly toward said tip in compression to effect its deployment from an initial angular orientation of said forward end region as an outward movement in adjacency with one side of said peripheral extent of said targeted tissue, said outward movement being to an extent curving said electrode into an outwardly depending arch formation having an arch apex of circumscription height extensible over said targeted tissue when said forward end region is pivoted, (d2) pivoting said forward end region to a second angular position to, in turn, pivot said electrode over said targeted tissue peripheral extent to a next side thereof opposite said one side, (d3) effecting retraction of said electrode by urging it rearwardly toward said base region to effect its retracting movement to a retracted orientation below said targeted tissue peripheral extent to effect said electrosurgical cut along three contiguous regions of said targeted tissue peripheral extent;

said steps (d1) through (d3) including the deployment of said barrier shroud behind said electrode to effect its positioning within said surgical cut along said three contiguous regions; and (e) simultaneously with said step (d) controlling said electrosurgical generator assembly to apply said first output to said electrode in electrical association with said electrosurgical return to establish an electrosurgical cut along said locus of movement of said electrode effective to provide a substantial vascular isolation of said targeted tissue from said viable tissue.

16. A method for carrying out the necrosis of a volume of targeted tissue exhibiting a given peripheral extent and surmounted by viable tissue, comprising the steps of:

(a) providing an electrosurgical generator assembly having an electrosurgical return, controllable to generate a first output for carrying out electrosurgical cutting of tissue;

said electrosurgical generator assembly being provided as being controllable to generate a second output for carrying out the coagulation of tissue;

(b) providing an instrument electrically coupled with said electrosurgical generator assembly, having a support member extending between a tip and a base region, having a forward end region extending along a longitudinal axis movable with respect to said targeted tissue, and having an electrode at said forward end region with a distal end fixed to said support member actuable for deployment from a retracted orientation to deployed orientations and from said deployed orientations toward a retracted orientation, said instrument deployment portion being provided to include an outwardly opening slot extending along said longitudinal axis, said electrode is thin and resilient, having a distal end connected with said support member at a connection location adjacent said tip and extending therefrom an arch defining distance, and including a membranous flexible anatomically resorbable barrier shroud having an outer edge coupled with said electrode, extending within said deployment portion during said insertion mode and deployable by said electrode;

(c) positioning said instrument forward end region within said viable tissue in adjacency with said targeted tissue peripheral extent with said electrode in a said retracted orientation;

(d) actuating said instrument to deploy said electrode in adjacency with said targeted tissue peripheral extent and thence along and in adjacency with said targeted tissue peripheral extent by pivoting said forward end region and retracting said electrode toward said retracted orientation to describe a locus of movement about said targeted tissue peripheral extent;

said step (d) comprising the steps of:

(d1) urging said electrode forwardly toward said tip in compression to effect its deployment from an initial angular orientation of said forward end region, said deployment being an outward, arch defining movement to a first deployed electrode location situated beneath and directed toward adjacency with a first side of said targeted volume of tissue, said deployment commencing the deployment of said barrier shroud;

(d2) pivoting said forward end region about said longitudinal axis to pivotally move said electrode to a second deployed location wherein said electrode is situated beneath and directed toward adjacency with a second side of said targeted volume of tissue opposite said first side, said deployment drawing said barrier shroud outer edge toward said second deployed location;

(d3) urging said electrode further forwardly toward said tip in compression to deploy it outwardly to a third deployed location defining an arch formation having an arch apex of height for pivotal movement over and adjacent to said target volume of tissue, said deployment drawing said barrier shroud outer edge toward said third deployed location;

(d4) pivoting said forward end region about said longitudinal axis to said initial angular orientation to pivotally move said electrode to a fourth deployed location wherein said electrode is situated in aligned adjacency within said first side of said targeted volume of tissue, said electrode movement drawing said barrier shroud outer edge toward said fourth deployed location;

(d5) retracting said electrode by urging it rearwardly to effect its retracting movement into said first deployed electrode location, said retracting movement drawing said barrier shroud outer edge toward said first deployed electrode location;

(f) reiterating said step (d);

(g) simultaneously with said step (f) controlling said electrosurgical generator assembly to apply said second output to said electrode in electrical association with said return to provide electrosurgical coagulation along said electrosurgical cut derived in said step (e); and (h) severing said shroud from said electrode at a location adjacent said forward edge.

17. Apparatus for electrosurgically cutting a targeted region of tissue, utilizing the output, including a return, of an electrosurgical generator, comprising:

a support member extending between a tip and a base region, having a forward end region extending along a longitudinal axis from said tip and positionable in an insertion mode into adjacency with said targeted region of tissue, and having a deployment portion at said forward end region adjacent said tip;

said support member forward end region being substantially cylindrical and said deployment portion including an outwardly open slot extending along said longitudinal axis from a securement region adjacent said tip to a forward location, thence along a deployment slot region to a rearward location, having a slot width defined between oppositely disposed slot sides extending a slot depth to a slot bottom, including an electrically insulative surface located at said slot sides and bottom, said support member forward end region slot depth exhibiting a first dimensional extent from said securement region to an output location, and exhibiting a second dimensional extent greater than said first dimensional extent therefrom rearwardly toward said base region, said support member including a barrier fluid delivery channel having a fluid input in the vicinity of said base region and extending within said slot beneath said electrode to said output location, a thin, resilient electrode extending within said deployment portion during said insertion mode and deployable to move outwardly from two spaced apart support locations to define an electrode cutting portion and retractable to move toward said deployment portion;

said electrode having a distal end positioned within said slot securement region and extending an arch defining distance beyond said rearward location;

an actuator and electrical circuit assembly extending along said support member from said base region, mechanically connected with said electrode for effecting said deployment and retraction thereof, and having a terminal assembly electrically connectable with said generator for coupling a first said applied output to said electrode providing, in operative association with said return, electrosurgical cutting of said tissue by said electrode along said cutting portion when deployed;

including a forward retainer component positioned over said electrode within said slot securement region and retaining it within said slot, and a rearward retainer component positioned within said slot over said electrode, said electrode being slidably mounted there beneath; and said actuator assembly being configured to deploy said electrode by urging it forwardly in compression to effect outward movement thereof generally transversely to said longitudinal axis to an extent curving it into an outwardly depending arch formation, and effecting retraction of said electrode by urging it rearwardly to effect inward movement thereof toward said slot.

18. Apparatus for electrosurgically cutting a targeted region of tissue, utilizing the output, including a return, of an electrosurgical generator, comprising:

a support member extending between a tip and a base region, having a forward end region extending along a longitudinal axis from said tip and positionable in an insertion mode into adjacency with said targeted region of tissue, and having a deployment portion at said forward end region adjacent said tip;

said support member forward end region being substantially cylindrical and said deployment portion including an outwardly open slot extending along said longitudinal axis from a securement region adjacent said tip to a forward location, having oppositely disposed slot sides extending a slot depth to a slot bottom, and said forward end region having an electrically insulative, generally channel-shaped retention insert fixed within said slot, having an outwardly opening electrode receiving channel with oppositely disposed internal side surfaces extending a channel depth to a channel bottom, having a securement region extending at a first channel depth from said slot securement end to a forward location, thence extending along a channel deployment region having a second depth, thence having a rearward location with a channel depth corresponding with said first channel depth;

said support member including a barrier fluid delivery channel having a fluid input in the vicinity of said base region and extending within said slot above said electrode to a fluid outlet extending from said rearward location within said retention insert channel deployment region, said fluid outlet having a channel width and a channel slot defining oppositely disposed channel outlet regions;

a thin, resilient electrode extending within said deployment portion during said insertion mode and deployable to move outwardly from two spaced apart support locations to define an electrode cutting portion and retractable to move toward said deployment portion;

said electrode having a distal end fixed with said retention insert securement region at said channel bottom and extending therefrom along said channel deployment region and beyond said rearward location an arch defining distance;

an actuator and electrical circuit assembly extending along said support member from said base region, mechanically connected with said electrode for effecting said deployment and retraction thereof, and having a terminal assembly electrically connectable with said generator for coupling a first said applied output to said electrode providing, in operative association with said return, electrosurgical cutting of said tissue by said electrode along said cutting portion when deployed;

said actuator assembly being configured to deploy said electrode by urging it forwardly in compression to effect outward movement thereof generally transversely to said longitudinal axis to an extent curving it into an outwardly depending arch formation, and effecting retraction of said electrode by urging it rearwardly to effect inward movement thereof toward said slot; and said actuator assembly being configured to effect movement of said electrode adjacent said rearward location into said channel slot during said outward movement.

* * * * *